US005844003A

United States Patent [19]
Tatton et al.

[11] Patent Number: 5,844,003
[45] Date of Patent: Dec. 1, 1998

[54] USE OF DEPRENYL COMPOUNDS TO MAINTAIN, PREVENT LOSS, OR RECOVER NERVE CELL FUNCTION

[75] Inventors: William G. Tatton, Halifax; Carol E. Greenwood, Toronto, both of Canada

[73] Assignee: Innovations Foundation, Toronto, Canada

[21] Appl. No.: 599,009

[22] Filed: Feb. 9, 1996

Related U.S. Application Data

[63] Continuation-in-part of Ser. No. 470,301, Jun. 6, 1995, abandoned, which is a continuation of Ser. No. 374,332, Jan. 18, 1995, which is a continuation of Ser. No. 203,726, Feb. 28, 1994, Pat. No. 5,444,095, which is a continuation of Ser. No. 929,579, Aug. 14, 1992, abandoned, which is a continuation of Ser. No. 772,919, Oct. 8, 1991, abandoned, which is a continuation-in-part of Ser. No. 751,186, Aug. 26, 1991, abandoned, which is a continuation-in-part of Ser. No. 678,873, Apr. 4, 1991, abandoned.

[51] Int. Cl.$^6$ .................................................. A61K 31/135
[52] U.S. Cl. .......................................................... 514/654
[58] Field of Search ............................................. 514/654

[56] References Cited

U.S. PATENT DOCUMENTS

| 4,861,800 | 8/1989 | Buyske ................................... 514/646 |
| 5,444,095 | 8/1995 | Tatton et al. . |

FOREIGN PATENT DOCUMENTS

| 0 473 252 A2 | 3/1991 | European Pat. Off. ................. 31/135 |
| WO 85/05617 | 12/1985 | WIPO . |
| WO 88/04552 | 6/1988 | WIPO ..................................... 31/135 |
| WO 90/01928 | 3/1990 | WIPO ..................................... 31/135 |
| WO 92/17169 | 10/1992 | WIPO ..................................... 31/135 |
| WO 93/12775 | 7/1993 | WIPO . |
| WO 95/11016 | 4/1995 | WIPO . |
| WO 96/22068 | 7/1996 | WIPO . |
| WO 96/26720 | 9/1996 | WIPO . |

OTHER PUBLICATIONS

Tatton et al, J. of Neuroscience Research, 30: 666–672 (1991).
Tatton et al, Can. J. Neurol. Sci., 1992; 19:124–133.
Birkmayer, W. et al.; (1985) "Increased Life Expectancy Resulting from Addition of L–Deprenyl to Madopar® Treatment in Parkinson's Disease: A Longterm Study"; *J. Neural Transmission*; 64; pp. 113–127.
Finnegan, Kevin T. et al.; (1990) "Protection against DSP–4–induced neurotoxicity by deprenyl is not related to its inhibition of MAO B"; *Euro. J. Pharmacol.*; 184(1); abstract of pp. 119–126.
Greenwood, Carol E. et al.; (1991) "Increased Dopamine Synthesis in Aging Substantia Nigra Neurons"; *Neurobiology of Aging*; vol. 12; pp. 557–565.
Heikkila et al; (1985) "Dopaminergic Neurotoxicity of 1–Methyl–4–phenyl–1,2,5,6–tetrahydropyridine (MPTP) in the Mouse: Relationships Between Monoamine Oxidase, MPTP Metabolism and Neurotoxicity"; *Life Sciences*; 36; pp. 231–236.

Jonakait, G. Miller et al.; (1988) "Development of serotonin, substance P and thyrotrophin–releasing hormone in mouse medullary raphe grown in organotypic tissue culture: developmental regulation by serotonin"; *Brain Research*, 473; pp. 336–343.
The Merck Index; (1983) 10th edition, Windholz, M. (Ed.), abstract 2893, p. 423, abstract 6988, p. 1023, abstract 1983; p. 282.
Rinne; (1991) "Nigral degeneration in Parkinson's disease in relation to clinical features"; *Acta Neurol Scand.*; 84: Supp. 136; pp. 87–90.
Rinne et al; (1991) "Selegine (deprenyl) treatment and death of nigral neurons in Parkinson's disease"; *Neurology*; 41; pp. 859–861.
Seniuk et al; (1990) "Dose–dependent destruction of the coeruleus–cortical and nigral–striatal projections by MPTP"; *Brain Res.*; 527(1); pp. 7–20.
Tatton et al.; (1992); "Interactions Between MPTP–Induced and Age–Related Neuronal Death in a Murine Model of Parkinson's Disease"; *Can. J. Neurological Sciences*; 19(1) (Supp.); pp. 124–133.
Tatton, W.G. and Greenwood, C.E., (1991); "Rescue of Dying Neurons: A New Action for Deprenyl in MPTP Parkinsonism"; *Journal of Neuroscience Research*; 30; pp. 666–672.
Tatton et al.; (1991) "Different Rates of Age–Related Loss For Four Murine Monoaminergic Neuronal Populations"; *Neurobiol. of Aging*; 12; pp. 543–556.
Tatton et al; (1991) "Transmitter synthesis increases in substantia nigra neurons of the aged mouse"; *Neuroscience Letters*; 131; pp. 179–182.
Tatton et al; (1990); "MPTP produces reversible disappearance of tyrosine hydroxylase–containing retinal amacrine cells"; *Brain Res.*; 527(1); pp. 21–31.
Timar, Julia; (1989) "Recovery of Mao–B Enzyme Activity After (–)Deprenyl (Selegiline) Pretreatment, Measured In Vivo"; *Acta Physiologica Hungarica*; vol. 74(3–4); pp. 259–266.
Torok, Tamas L. et al; (1987) "Transmitter releasing action of selegiline ((–)–deprenyl) from peripheral sympathetic nerves under different experimental conditions"; *J. Pharm. Pharmacol.*; 39(10); abstract of pp. 797–802, pp. 48 of Chemical Abstracts.
Zsilla, Gabriella et al.; (1984) "Neurochemical evidences for facilitation of dopaminergic function in rat brain by repeated doses of (–) deprenyl"; *Dev. Neurosci. (Amsterdam)*; 17 (*Regular Transm. Funct.: Basic Clin. Aspects*); abstract of pp. 345–348; pp. 64 of Chemical Abstracts.

(List continued on next page.)

*Primary Examiner*—Rebecca Cook
*Attorney, Agent, or Firm*—Elizabeth A. Hanley; Mark D. Russett; Lahive & Cockfield, LLP

[57] ABSTRACT

The present invention relates to the use of deprenyl compounds to rescue damaged nerve cells in a patient and to kits containing deprenyl compounds useful for rescuing damaged nerve cells in a patient.

21 Claims, 33 Drawing Sheets

OTHER PUBLICATIONS

Zsilla, Gabriella et al.; (1986) "The Effect of Repeated Doses of (–) Deprenyl On The Dynamics of Monoaminergic Transmission. Comparison With Clorgyline"; *Pol. J. Pharmacol. Pharm.*; 38; pp. 57–67.

Zsilla, Gabriella et al.; (1983) "(–)–Deprenyl A Selective Mao 'B' Inhibitor Increases [$^3$H]imipramine Binding And Decreases β–Adrenergic Receptor Function"; *European Journal of Pharmacology*; 89; pp. 111–117.

Zsilla, G. and Knoll, J.; (1982) "The Action of (–)Deprenyl on Monoamine Turnover Rate in Rat Brain"; *Typical and Atypical Antidepressants: Molecular Mechanisms*; pp. 211–217.

Heinonen, E.H. et al;. (1993) "Desmethylselegiline, a metabolite of selegiline, is an irreversible inhibitor of MAO–B in human subjects"; *Neurology*; vol. 43(4); pp. A156.

Knoll, J. et al.; (1992) "(–)Deprenyl and (–)parafluorodeprenyl treatment prevents age–related pigment changes in the substania nigra"; *Mech. Ageing Dev;*; vol. 63(2); pp. 157–163.

Magyar, K.; (1994) "Behaviour of (–)deprenyl and its analogues" *Journal of Neural Transmission*; vol. 41; pp. 167–175.

Nickel B. et al.; (1990) "Effect of selegiline and desmethyl–selegiline on cortical electric activity in rats" *Journal of Neural Transmission*; Suppl. 32; pp. 139–144.

Rao, T.S., et al.; (1987) "N, N–Dipropargyl– 2–Phenylethylamine, a potential prodrug of 2–Phenylethlamine: neurochemical and neuropharmalogical studies in rat" *Brain Res. Bull.*; vol. 19(1); pp. 47–55.

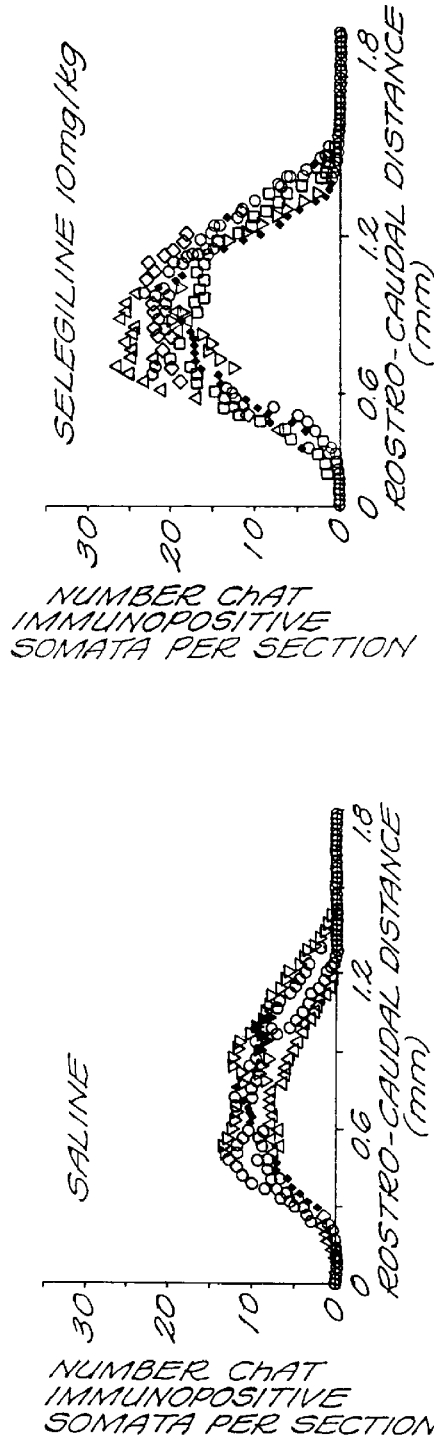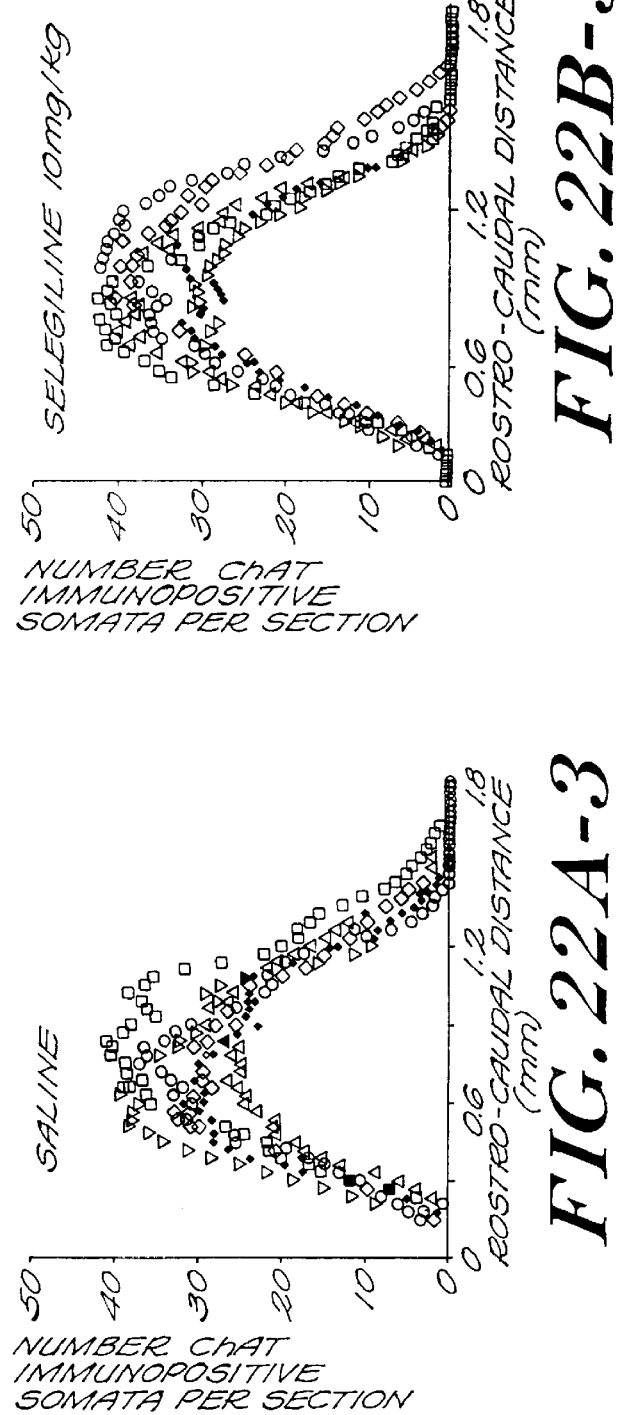

USE OF DEPRENYL COMPOUNDS TO MAINTAIN, PREVENT LOSS, OR RECOVER NERVE CELL FUNCTION

This application is a continuation-in-part of USSN 08/470,301, filed Jun. 6, 1995, which is a continuation of USSN 08/374,332, filed Jan. 18, 1995, which is a continuation of USSN 08/203,726, filed Feb. 28, 1994, now U.S. Patent No. 5,444,095, which is a continuation of USSN 07/929,579, filed Aug. 14, 1992, abandoned, which is a continuation-in-part of USSN 07/772,919, filed Oct. 8, 1991, abandoned, which is a continuation-in-part of USSN 07/751,186, filed Aug. 26, 1991, abandoned, which is a continuation-in-part of USSN 07/678,873, filed Apr. 4, 1991 abandoned. The contents of all the aforementioned applications and issued patents are hereby expressly incorporated by reference.

FIELD OF THE INVENTION

The present invention relates to the use of deprenyl compounds to rescue damaged nerve cells in an animal; to pharmaceutical compositions containing deprenyl adapted for such use; and, to methods for the treatment of disorders of the nervous system by rescuing damaged nerve cells in an animal. The invention also relates to methods for testing drugs for their activity in rescuing nerve cells in an animal.

BACKGROUND OF THE INVENTION

Deprenyl (also referred to herein as selegiline or R-(-)-N,α-Dimethyl-N-2-propynyl phenethylamine) was first used as an adjunct to conventional drug therapy (L-dihydroxyphenylalanine (L-DOPA) plus a peripheral decarboxylase inhibitor) of Parkinson's disease (PD) in Europe over a decade ago on the basis that as a selective monoamine oxidase-B (MAO-B) inhibitor, it would elevate brain dopamine levels and potentiate the pharmacologic action of dopamine formed from L-DOPA, and yet prevent the tyramine-pressor effect observed with non-selective MAO inhibitors. The combined drug therapy was reported to prolong the anti-akinetic effects of L-DOPA, resulting in the disappearance of on-off effects, reduced functional disability, and increased life-expectancy in PD patients (Bernheimer, H., et al., J. Neurolog. Sci., 1973. 20: 415–455, Birkmayer, W., et al., J. Neural Transm., 1975. 36:303–336, Birkmayer, W., et al., Mod. Prob. Pharmacopsychiatr., 1983. 19: 170–177, Birkmayer, W. and P. Riederer, Hassler, R. G. and J. F. Christ (Ed.) Advances In Neurology, 1984. 40(Y): p.0-89004, and Birkmayer, W., et al., J. Neural Transm., 1985. 64(2): p. 113–128).

Studies examining deprenyl as an adjunct to conventional L-DOPA therapy have reported a short term benefit which was usually lost by 1 year or less. Some, but not all, have reported that the levodopa dose can be decreased when taken in conjunction with deprenyl (Elizan, T. S., et al., Arch Neurol, 1989. 46(12): p. 1280–1283, Fischer, P. A. and H. Baas, J. Neural Transm. (suppl.), 1987. 25: p. 137–147, Golbe, L. I., Neurology, 1989. 39: p. 1109– 1111, Lieberman, A. N. et al., N.Y. State J. Med., 1987. 87: p. 646–649, Poewe, W., F. Gerstenbrand, and G. Ransomayr, J. Neural Transm. (suppl.), 1987. 25: p. 137–147, Cedarbaum, J. M., M. Hoey, and F. H. McDowell, J. Neurol. Neurosurg. Psychiatry, 1989. 52(2): p. 207–212, and Golbe, L. I., J. W. Langston, and I. Shoulson, Drugs, 1990. 39(5): p. 646–651).

Increasingly, deprenyl is being administered to Parkinson's disease patients following reports (Parkinson, S. G. Arch Neurol 46, 1052–1060 (1989) and U.S.A., Parkinson, S. G. N. Engl. J. Med. 321, 1364–1371 (1989)) that it delays the disease progression; however, no satisfactory mechanism has been proposed to explain its action.

Support for the use of deprenyl in Parkinson's disease (PD) is largely based on the findings of the DATATOP project (Parkinson, S. G. Arch Neurol 46, 1052–1060 (1989) and U.S.A., P.S.G. N. Engl. J. Med. 321j 1364–1371 (1989)). This multicentre study reported that deprenyl delays the onset of disabling symptoms requiring additional pharmacotherapy by nearly one year; these findings were reproduced in an independent but smaller study (Tetrud, J. W. & Langston, J. W. Science 245, 519–522 (1989)). Unfortunately, the design of the DATATOP study and its conclusions have come under strong criticism (Landau, W. M. Neurology 40, 1337–1339 (1990). Furthermore, while the authors of these projects state that their results are consistent with the hypothesis that deprenyl slows the progression of PD (Parkinson, S. G. Arch Neurol 46, 1052–1060 (1989), U.S.A., P.S.G.N. Engl. J. Med. 321, 1364–1371 (1989) and Tetrud, J. W. & Langston, J. W. Science 249, 303–304 (1990)), they by no means constitute proofs (Tetrud, J. W. & Langston, J. W. Science 249, 303–304 (1990)).

It has been proposed that deprenyl, an MAO-B inhibitor, may delay the progression of PD by minimizing free-radical induced death of surviving dopaminergic nigrostriatal (DNS) neurons (Langston, J. W. in Parkinson's Disease and Movement Disorders (eds. Jankovic, J. & Tolosa, E.) 75–85 (Urban and Schwarzenberg, Baltimore-Munich 1988)) based on the observation that deprenyl could block MPTP-induced neurotoxicity in primates (Langston, J. N., Forno, L. S. Robert, C. S. & Irwin, I. Brain Res 292, 390–394 (1984)) and the hypothesis that other environmental toxins with mechanisms of action similar to that of MPTP may be involved in the etiology of PD (Tanner, C. M. TINS 12:49–54 (1989)). However, since MAO-B is not present in dopaminergic neurons (Vincent, S. R. Neuroscience 28, 189–199 (1989), Pintari, J. E., et al. Brain Res 276:127–140 (1983), Westlund, K. N., Denney, R. M., Rochersperger, L. M., Rose, R. M. & Abell, C. W. Science (Wash. D.C.) 230, 181–183 (1985) and Westlund, K. N., Denney, R. M., Rose, R. M. & Abell, C. W. Neuroscience 25, 439–456 (1988)), it is unclear how its inhibition would protect DNS neurons unless another highly toxic compound were formed in non-dopaminergic neurons which could in turn damage DNS neurons in a manner analogous to that of MPTP. Surprisingly, no investigation has included the measurement of DNS neuronal numbers to determine whether deprenyl could influence neuronal survival when measured after MPTP has cleared from the central nervous system.

SUMMARY OF THE INVENTION

Broadly stated the present invention relates to the use of deprenyl compounds to rescue damaged nerve cells in a patient.

In one aspect, the invention provides a method for rescuing damaged nerve cells in a patient, including administering to a patient having damaged nerve cells an amount of a deprenyl compound such that rescuing of damaged nerve cells occurs in the patient; with the proviso that the deprenyl compound is not selected from the group consisting of deprenyl, pargyline, AGN-1 133, or AGN-1135.

The invention also relates to a pharmaceutical composition for use in the treatment of disorders of the nervous system comprising an amount of a deprenyl compound, effective to rescue damaged nerve cells in a patient.

The invention further relates to a method for the treatment of disorders of the nervous system by rescuing damaged nerve cells in a patient comprising administering to a patient an amount of a deprenyl compound effective to rescue damaged nerve cells.

BRIEF DESCRIPTION OF THE DRAWINGS

Further details of the invention are described below with the help of the examples illustrated in the accompanying drawings in which:

FIG. 19 shows photomicrographs of adjacent ChAT immunoreacted (A1 and B1) and Nissl stained (A2 and B2) sections through the facial nucleus ipsilateral to transection of the facial nerve;

FIG. 22 shows ChAT+ counts for facial motoneurons in 35 day old rats after a unilateral axotomy at 14 days of age;

DETAILED DESCRIPTION OF THE INVENTION

Figure 1:
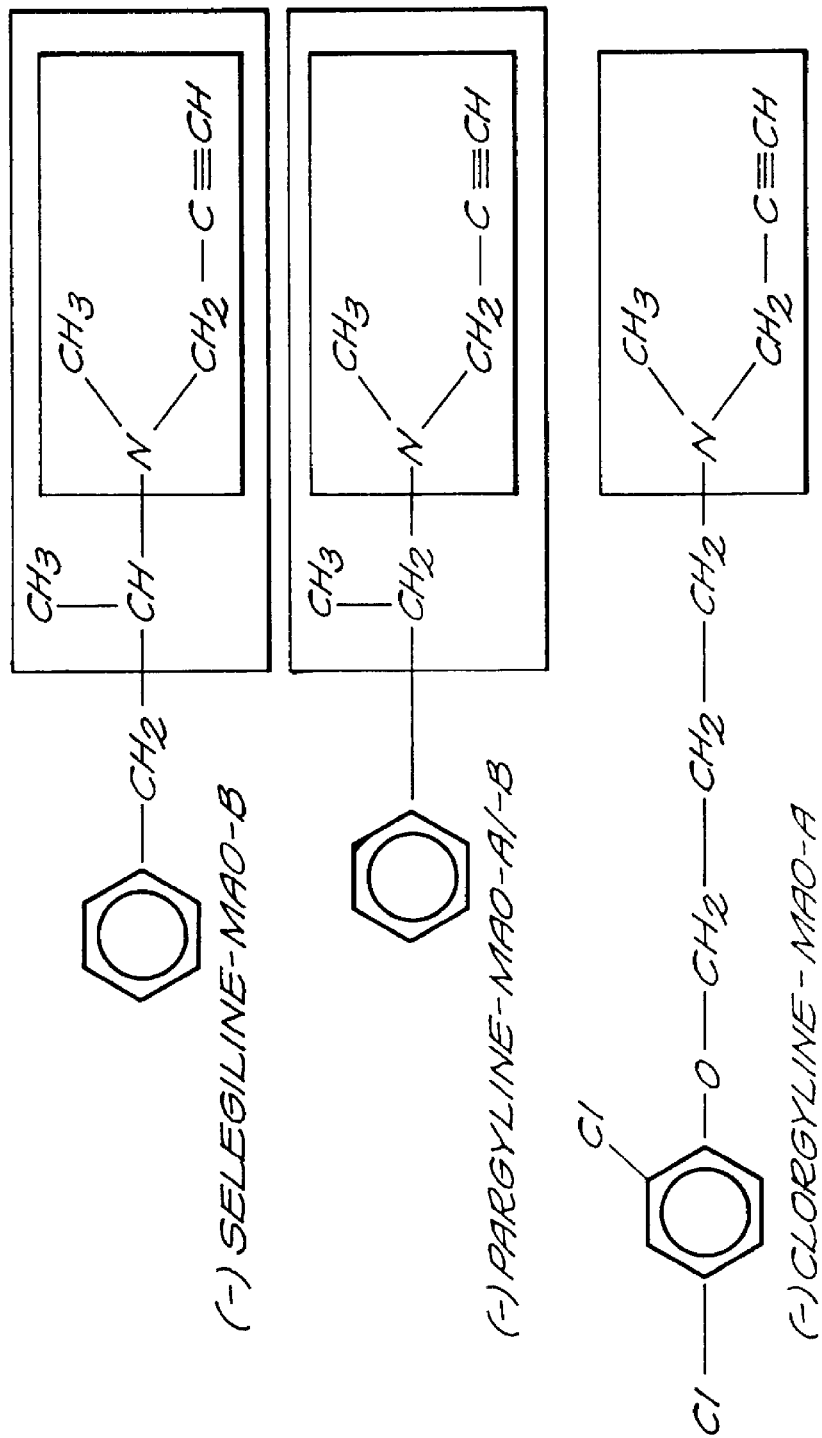
FIG. 1 shows a comparison of the known molecular structures of L-deprenyl, clorgyline and pargyline.

The present invention provides methods for rescuing damaged nerve cells by administering a deprenyl compound to a patient.

In one aspect, the invention provides a method for rescuing damaged nerve cells in a patient, comprising: administering to a patient having damaged nerve cells an amount of a deprenyl compound such that rescuing of damaged nerve cells occurs in the patient; with the proviso that the deprenyl compound is not selected from the group consisting of deprenyl, pargyline, AGN-1133, or AGN-1135.

The terms "patient" or "subject", as used herein, refer to a warm-blooded animal having damaged nerve cells. In preferred embodiments, the patient is a mammal, including humans and non-human mammals such as dogs, cats, pigs, cows, sheep, goats, rats, and mice. In a particularly preferred embodiment, the patient is a human.

The terms "rescue of damaged nerve cells" or "rescuing of damaged nerve cells" herein refer to the reversal of the sequence of damage to death in (otherwise) lethally damaged nerve cells and/or compensation in part for the loss of muscle-derived trophic support.

The present inventors have studied the time course of neuronal death induced by the neurotoxin 1-methyl-4-phenyl-1,2,5,6-tetrahydropyridine (MPTP). MPTP is oxidized, under the action of monoamine oxidase-B (MAO-B), via a dihydropyridium intermediate (MPDP+) to its toxic metabolite 1-methyl-4-phenyl-pyridinium ion (MPP+). It is believed that MPTP is converted to MPP+in nondopaminergic cells, released and then taken up into dopaminergic neurons where it exerts its neurotoxic effects (see Vincent S. R. Neuroscience, 1989, 28 p. 189–199, Pintari, J. E. et al. Brain Res, 1983, 276(1) p. 127–140, Westlund, R. N. et al. Neuroscience, 1988, 25(2) p. 439–456, Javitch, J. A. et al. P.N.A.S. USA 1985, 82(7) p. 2173–2177, Mayor, 1986 #1763, and Sonsalla, P. R. et al. 17th Annual Meeting Of The Society For Neuroscience, New Orleans, La., USA, Nov., 1987, 13(2)).

MPTP is rapidly metabolized and cleared in the mouse (Johannessen, J. N. et al. Life Sci. 1985, 36: p. 219–224, Markey, S. P. et al. Nature, 1984, 311 p. 465467, Lau, Y. S. et al. Life Sci. 1988, 43(18): p. 14591464). In contrast to the rapid metabolism and excretion of MPTP, the present inventors have demonstrated that loss of dopaminergic neurons progresses over a period of twenty days following cessation of MPTP administration. MPTP (30 mg/kg/d) was administered i.p. to mice for five consecutive days (total cumulative dose 150 mg/kg) to produce a loss of approximately 50% of TH-immunopositive (TH+) neurons in the substantia nigra compacta (SNc) and ventral tegmental area (VTA)(see Seniuk, N. A., W. G. Tatton, and C. E. Greenwood, Brain Res., 1990. 527s p. 7–20 which are incorporated herein by reference for the relationship between MPTP dose and loss of catecholaminergic neurons).

The present inventors have also found that the death of TH+ SNc neurons followed a similar timecourse. 20–30% of TH+ somata were lost by the five days after the completion of the administration of MPTP; loss of TH+ neurons continued over the next ten to fifteen days with no detectable loss thereafter. This continual loss of TH+ neurons could not be accounted for by the presence of MPP+, based on the excretion data referred to above. Joint plots of counts of TH+ and Nissl stained SNc somata als0 confirmed that the loss of TH+ somata represented the death of SNc neurons rather than a loss of TH immunoreactivity.

In tandem with the loss of TH+ SNc somata the present inventors have also found changes in immunodensity of TH protein in SNc and the ventral tegmental area (VTA). Cytoplasmic TH immunodensity was 40% lower in the somata of the remaining TH+ DNS neurons for MPTP-treated animals at day 5 in comparison to saline treated controls. Average somal TH-immunodensity increased over time and had reached control levels by 20 days following MPTP. Alterations in striatal DA concentrations and dopamine-dependent behaviors such as locomotion were found to parallel the changes in TH-immunochemistry. Further, the present inventors found that an increase in striatal DA content and DA synthesis as estimated by DOPAC/DA ratios also appeared to parallel behavioral recovery and indicated increased DA content and synthesis in the VTA and SNc neurons surviving MPTP exposure.

Thus, the present inventors have significantly found that following MPTP-induced neuronal damage, there is a critical 20 day period in which TH+ SNc neurons either undergo effective repair and recovery or else they die.

Most studies with deprenyl have been designed to demonstrate that inhibition of MAO-B activity in vivo blocks the conversion of NPTP to MPP+ and the neurotoxicity of MPTP. As a consequence, deprenyl was usually given either several hours or for several days prior to and then throughout MPTP administration to ensure that MAO-B activity was inhibited during the time of MPTP exposure (for example, see Cohen, G., et al., Eur. J. Pharmacol., 1984. 106s p. 209–210, Heikkila, R. E., et al., Eur. J. Pharmacol, 1985. 116(3): p. 313–318, Heikkila, R. E., et al., Nature, 1984. 311: p. 467–469 and Langston, J. W., et al., Science (Wash. D.C.), 1984, 225 (4669) p. 1480–1482). Comparable results have been obtained using other selective inhibitors of MAO-B such as AGN1133, AGN-1135 and MD 240928 (Heikkila, R. E., et al., Eur. J. Pharmacol, 1985. 116(3): p. 313–318 and Fuller, R. W. and L. S. K. Hemrick, Life Sci, 1985. 37(12): p. 1089–1096) suggesting that the mechanism of action of deprenyl was mediated by its ability to block MAO-B and thereby prevent the toxin from being converted to its active form.

In contrast to the above studies, the present inventors were interested in determining whether deprenyl could exert an effect on DSN neurons which was independent of its ability to block MPTP conversion to MPP+. MPTP-treated mice (cumulative dose of 150 mg/kg) received deprenyl (0.01, 0.25, 10 mg/kg i.p.; 3 times per week) from day 3 to day 20 following MPTP administration. Deprenyl administration was withheld until day 3 to ensure that all mice were exposed to comparable levels of MPP+ and that all MPTP and its metabolites had been eliminated from the central nervous system. Clorgiline, an MAO-B inhibitor, was also administered to the MPTP-treated mice.

The present inventors found that in saline treated mice, about 38% of dopaminergic substantia nigracompacta (DSN) neurons died progressively over the twenty days. The number of DSN neurons was found to be statistically the same in the MPTP-Saline and MPTPClorgiline treated mice. However, deprenyl increased the number of DSN neurons surviving MPTP-induced damage (16% loss—0.01 mg/kg, 16% loss—0.25 mg/kg, and 14% loss 10 mg/kg), with all doses being equipotent. Thus, the present inventors have demonstrated that deprenyl could rescue dying neurons and increase their probability of undergoing effective repair and re-establishing their synthesis of enzymes, such as tyrosine hydroxylase, necessary for dopamine synthesis. This is believed to be the first report of a peripherally or orally administered treatment which reverses the sequence of damage to death in neurons which would have otherwise died.

The inventor's studies ruled out the possibility that deprenyl was mediating its resuscitative effect through inhibition of MPTP conversion to its toxic metabolite NPP+. The results suggest that deprenyl has a previously unidentified mechanism of action. It is difficult to reconcile a direct effect of deprenyl in dopaminergic neurons themselves due to the absence of MAO-B in these cells (Vincent, S. R., Neuroscience 28, 189–199 (1989); Pintari, J. E., et al. Brain Res. 276, 127–140 (1983); Westlund, R. N. et al. Science, (Wash D.C.) 230, 181–183 (1988) and Westlund, K. N. et al. Neuroscience 25, 439–456 (1988)), making it unlikely that the results can be explained on the basis of MAO-B inhibition by deprenyl within the dopaminergic neurons themselves. Measurements of MAO-A and MAO-B in MPTP mice at the beginning and end of treatment with deprenyl (0.01 mg/kg) showed that the 0.01 mg/kg dose did not produce any significant MAO-A or MAO-B inhibition at the two time periods, suggesting that it is highly unlikely that deprenyl mediates its resuscitative effect thought inhibition of MAO-B. Further, clorgyline an MAO-A inhibitor did not increase the number of surviving DSN neurons after neuronal death induced by MPTP.

Other results have confirmed that the rescue of damaged neurons by deprenyl does not depend on the known MAO-B or MAO-B inhibition activity. It has been demonstrated that the rescue of axotomized motoneurons bydeprenyl (see discussion below) is permanent as the) motoneurons do not die when the deprenyl treatment is subsequently discontinued. It has also been demonstrated that the MAO-B inhibitor N-(2-aminoethyl)-4-chlorobenzamide hydrochloride is not effective in rescuing damaged motoneurons.

The survival of rat facial motoneurons after axotomy at 14 days of age was also examined and it was found that deprenyl increased by 2.2 times the number of motoneurons surviving 21 days after the axotomy (See Example 3 herein). Further, a dose of 0.01 mg/kg of deprenyl was just as effective as 10 mg/kg deprenyl in rescuing the motoneurons similar to the 0.01 mg/kg dose used with the MPTP model. Pargyline has also been shown to rescue motoneurons. Thus, it has been significantly demonstrated that deprenyl and pargyline can compensate in part for the loss of trophic support caused by axotomy suggesting a role for deprenyl compounds in the treatment of motoneuron death in conditions such as amyotrophic lateral scleroais.

Animals lesioned at 14 days, treated for the next 21 days with 10 mg/kg deprenyl (dl4-35) and then left untreated until 65 days of age did not show any further motoneuronal death. It was also demonstrated, that the rescue is permanent for the axotomized motoneuron i.e. the motoneurons do not begin to die when deprenyl treatment is discontinued after 21 days and there is no further death over the next 30 days.

The resuscitative effect of deprenyl may be mediated by any of the cells in the nervous system and the mechanism likely involves the activation of a receptor on the cells (such as a receptor for a neuronotrophic factor) through a structure which may not be related to the structure which blocks MAO-B. This would imply that deprenyl could help prevent the death of all neurons in the brain that respond to glial trophic factors, rather than just influencing dopaminergic neurons alons. Hence as well as being therapeutically effective in Parkinson's disease, it would also be effective in other neurodegenerative and neuromuscular diseases and in brain damage due to hypoxia, ischemia, stroke or trauma and may even 810w the progressive loss of neurons associated with brain aging (Coleman, P. D. & Flood D. G., Neurobiol. Aging 8, 521–845 (1987); McGeer, P. L. et al. in Parkinsonism and Aging (eds. D. B. Calne, D,C, - G. Comi and R. Horowski) 25–34 (Plenum, N.Y., 1989). It may also be useful in stimulating muscle reinnervation in traumatic and nontraumatic peripheral nerve damage.

The present studies also indicate that the propargyl terminus may be a factor required for the rescue of damaged neurons. As indicated above, the MAO-A inhibitor, clorgyline, at doses of 2 mg/kg delivered every second day, did not increase the number of surviving dSNC neurons after MPTP-induced damage. A comparison of the known molecular structures of L-deprenyl and clorgyline (See FIG. 1), reveals that the compounds have the same structure in the terminal portion which contains the propargyl group See box in FIG. 1). In contrast, the phenol ring includes the two bulky chlorines and an oxygen-linked 3 carbon chain attaches the chlorine-substituted phenol to the nitrogen with 2 carbons with amethyl side chain in L-deprenyl. The inability of clorgyline to rescue the DSN neurons may relate to the chlorines preventing the propargyl group from reaching an attachment site or may indicate that the critical structure includes the portion of the molecule linking the phenol ring to the nitrogen.

The MAO-B inhibitor N-(2-aminoethyl)-4chlorobenzamide hydrochloride was found not to rescue immature axotomized motoneurons. The compound does not have the terminal alkyne moiety of deprenyl and pargyline so it appears that it binds to or interacts with a different part of the flavine portion of MAO-B.

The (+) isomer of deprenyl at a dosage of 0.01 mg/kg was found not to rescue immature axotomized motoneurons. Thus, the optical rotation of the compounds may also be important for the rescue.

As discussed above, the present invention relates to the use of deprenyl compounds to rescue damaged nerve cells, to pharmaceutical compositions containing deprenyl compounds adapted for such use; and, to methods for the treatment of disorders of the nervous system by rescuing damaged nerve cells.

The administration of deprenyl compounds may rescue damaged nerve cells in an animal, and thus may be used for the treatment of neurodegenerative and neuromuscular diseases and in acute damage to nervous tissue due to hypoxia, hypoglycemia, ischemic stroke or trauma. It may also be used to slow the progressive loss of neurons associated with brain aging; although the present inventors have shown that deprenyl does not prevent age-related death of mouse DSN neurons. More specifically, deprenyl compounds may be used to treat Parkinson's disease, ALS, head trauma or spinal cord damage, patients immediately following an ischemic stroke, hypoxia due to ventilatory deficiency, drowning, prolonged convulsion, cardiac arrest, carbon monoxide exposure, exposure to toxins, or viral infections. Deprenyl compounds may also be used to stimulate muscle reinnervation in traumatic and nontraumatic peripheral nerve damage.

I. Deprenyl Compounds

The language "deprenyl compound", as used herein, includes deprenyl (N,α-dimethyl-N-2-propynylphenethylamine), compounds which are structurally similar to deprenyl, e.g., structural analogs, or derivatives thereof. Thus, in one embodiment, a deprenyl compound can be represented by the following formula (Formula I):

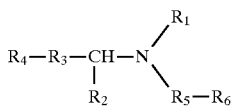

Formula I in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or —(CH2)$_n$—X—(CH2)$_m$;

in which X is O, S, or N-methyl; m is 1 or 2; and n is 0,1, or 2;

$R_4$ is alkyl, alkenyl, alkynyl, heterocyclyl, aryl or aralkyl; and $R_5$ is alkylene, alkenylene, alkynylene and alkoxylene; and $R_6$ is $C_3$–$C_6$ cycloalkyl or —C≡CH; or $R_2$ and $R_4$–$R_3$ are joined to form, together with the methine to which they are attached, a cyclic or polycyclic group;

and pharmaceutically acceptable salts thereof.

In certain preferred embodiments, a deprenyl compound is not selected from the group consisting of deprenyl, pargyline, AGN-1133, AGN-1135, or MD 240928.

In preferred embodiments, $R_1$ is a group that can be removed in vivo. In certain embodiments, $R_1$ is hydrogen. In other preferred embodiments, $R_1$ is methyl. In certain preferred embodiments, $R_2$ is hydrogen. In certain preferred embodiments, $R_2$ is methyl. In some preferred embodiments, $R_3$ is alkylene, more preferably methylene. In other preferred embodiments, $R_3$ is —(CH$_2$)$_n$—X—(CH$_2$)$_m$. In preferred embodiments, $R_4$ is aryl. In certain preferred embodiments, $R_4$ is phenyl. In other preferred embodiments, $R_4$ is aralkyl. In yet other preferred embodiments, $R_4$ is alkyl. In still other preferred embodiments, $R_5$ is alkylene, more preferably methylene. In certain preferred embodiments, $R_6$ is

—C≡CH

In other preferred embodiments, $R_6$ is cyclopentyl.

In another preferred embodiment, the deprenyl compound has the structure

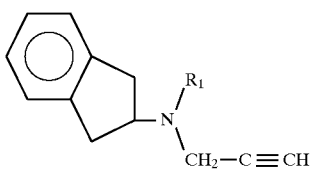

wherein $R_1$ is as described above. Preferred deprenyl compounds include (−)-desmethyldeprenyl, and

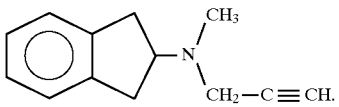

In another embodiment, a deprenyl compound can be represented by the following formula (Formula II):

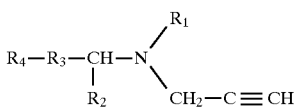                                    Formula II in which
$R_1$ is hydrogen, alkyl, alkenyl, alkynyl, aralkyl, alkylcarbonyl, arylcarbonyl, alkoxycarbonyl, or aryloxycarbonyl;
$R_2$ is hydrogen or alkyl;
$R_3$ is a bond or methylene; and
$R_4$ is aryl or aralkyl; or
$R_2$ and $R_4$-$R_3$ are joined to form, together with the methine to which they are attached, a cyclic or polycyclic group;
and pharmaceutically acceptable salts thereof.

In another embodiment, the deprenyl compound can be represented by the following formula (Formula III):

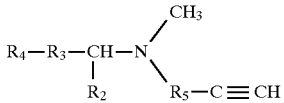                                    Formula III in which
$R_2$ is hydrogen or alkyl;
$R_3$ is a bond or methylene; and
$R_4$ is aryl or aralkyl; or
$R_2$ and $R_4$-$R_3$ are joined to form, together with the methine to which they are attached, a cyclic or polycyclic group; and
$R_5$ is alkylene, alkenylene, alkynylene and alkoxylene;
and pharmaceutically acceptable salts thereof.

In yet another embodiment, the deprenyl compound can be represented by the following formula (Formula IV):

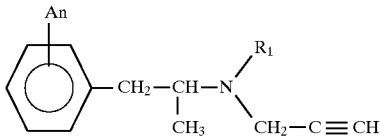

Formula IV in which
$R_1$ is hydrogen, alkyl, alkenyl, alkynyl, aralkyl, alkylcarbonyl, arylcarbonyl, alkoxycarbonyl, or aryloxycarbonyl;
A is a substituent independently selected for each occurence from the group consisting of halogen, hydroxyl, alkyl, alkoxyl, cyano, nitro, amino, carboxyl, —$CF_3$, or azido;

n is 0 or an integer from 1 to 5;
and pharmaceutically acceptable salts thereof.

In certain embodiments of the invention, the deprenyl compound is not deprenyl (including (−)-deprenyl).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$–$C_{20}$ for straight chain, $C_3$–$C_{20}$ for branched chain), and more preferably 10 or fewer. Likewise, preferred cycloalkyls have from 4–10 carbon atoms in their ring structure, and more preferably have 5, 6 or 7 carbons in the ring structure. Unless the number of carbons is otherwise specified, "lower alkyl" as used herein means an alkyl group, as defined above, but having from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group (e.g., an aromatic or heteroaromatic group). Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to -C(O)-alkyl. Similarly, the term "arylcarbonyl" refers to -C(O)-aryl. The term "alkyloxycarbonyl", as used herein, refers to the group -C(O)-O-alkyl, and the term "aryloxycarbonyl" refers to -C(O)-O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to -N($R_8$)($R_9$), in which $R_8$ and $R_9$ are each independently hydrogen, alkyl, alkyenyl, alkynyl, aralkyl, aryl, or $R_8$ and $R_9$, together with the nitrogen atom to which they are attached, form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above for alkyls, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

The terms "heterocyclyl" or "heterocyclic group" refer to 4- to 10-membered ring structures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The term "can be removed in vivo", as used herein, refers to a group that can be cleaved in vivo, either enzymatically or non-enzymatically. For example, amides can be cleaved by amidases, and N-methyl amines can be cleaved by enzymatic oxidation. For example, when deprenyl is administered to a subject, it is believed, as described infra, that the methyl group can be removed in vivo to yield an active compound. As a further example, with reference to Formula I, when $R_1$ is alkylcarbonyl, the resulting amide group can be hydrolytically cleaved in vivo, enzymatically or non-enzymatically, to yield a deprenyl compound including a secondary amine (e.g., $R_1$ is converted to hydrogen in vivo). Other groups which can be removed in vivo are known (see, e.g., R. B. Silverman (1992) "The Organic Chemistry of Drug Design and Drug Action", Academic Press, San Diego) and can be employed in compounds useful in the present invention.

II. Pharmaceutical Compositions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deprenyl compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The stability of deprenyl can be affected by the pH of the medium in which the deprenyl is formulated. For example, deprenyl is more stable at a pH in the range of about 3–5 than at a pH of about 7. Therefore, when formulating a deprenyl compound in a pharmaceutical composition, it is preferred that the deprenyl compound be maintained at a suitable pH. In preferred embodiments, a pharmaceutical composition of the invention has a pH in the range of about 3 to about 5, more preferably about 3 to about 4. Furthermore, ethyl alcohol is a preferred solvent for improving stability of deprenyl. Thus, in certain embodiments, alcoholic or aqueous alcoholic media are preferred for the pharmaceutical compositions of the invention.

As set out above, certain embodiments of the present deprenyl compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like (see, for example, Berge et al. (1977) "Pharmaceutical Salts",J. Pharm. Sci. 66:1–19).

In other cases, the deprenyl compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and is aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the deprenyl compound which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Methods of preparing these formulations or compositions include the step of bringing into association at least one deprenyl compound of the present invention with the carrier and, optionally, one or more accessory ingredients. In general, the formulations are prepared by uniformly and intimately bringing into association a deprenyl compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A deprenyl compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (I) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deprenyl compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the deprenyl compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deprenyl compound, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more deprenyl compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the deprenyl compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a deprenyl compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a deprenyl compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deprenyl compound in the proper medium. Absorption enhancers can also be used to increase the flux of the deprenyl compound across the skin. The rate of such flux can be controlled by either providing a rate controlling membrane or dispersing the deprenyl compound in a polymer matrix or gel. Devices, including patches, which transdermally deliver a deprenyl compound by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise one or more deprenyl compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject deprenyl compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Injection (subcutaneous or intraperitoneal) or topical ophthalmic administration are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deprenyl compound of the present invention employed, or the ester, salt or amide thereof, the route of administration, the time of administration, the rate of excretion of the particular compound being employed, the duration of the treatment, other drugs, compounds and/or materials used in combination with the particular deprenyl compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a deprenyl compound of the invention will be that amount of the compound which is the lowest dose effective to produce a therapeutic effect. Such an effective dose will generally depend upon the factors described above. Generally, intraperitoneal and subcutaneous doses of the compounds of this invention for a patient, when used for the indicated nerve-cell rescuing effects, will range from about 0.0001 to about 10 mg per kilogram of body weight per day, more preferably from about 0.001 mg/kg to about 1 mg/kg per day.

If desired, the effective daily dose of a deprenyl compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition). It will be understood that two or more deprenyl compounds can be administered in a single therapeutic composition.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

It is believed that certain deprenyl compounds can be at least partially metabolized in vivo after administration to a subject. For example, (−)-deprenyl can be metabolized by the liver to (−)-desmethyldeprenyl, as well as (−)-methamphetamine and (−)-amphetamine, after oral administration. The hepatic metabolism of (−)-deprenyl can be inhibited by administration of a P450 inhibitor such as Proadifen. In animal and cell-culture studies, administration of Proadifen reduces the ability of (−)-deprenyl to prevent cell death, but does not block the cell-rescuing activity of (−)-desmethyldeprenyl. Thus, it is believed that at least one metabolite of (−)-deprenyl, most likely (−)-desmethyldeprenyl, is an active compound. It is presently believed that (−)-methamphetamine and (−)-amphetamine are inhibitors of the cell-rescuing activity of deprenyl compounds. It is also believed that monoamine oxidase (MAO, including both MAO-A and MAO-B) inhibitory activity is not required for nerve-cell rescuing activity. Absence of MAO inhibitor activity may in fact provide a drug with fewer side effects. Thus, in certain embodiments, it is preferred that the deprenyl compound have low MAO inhibitor activity, or be administered so as to minimize MAO inhibition (e.g., by use of a suitable prodrug or formulation).

In view of the foregoing, it is preferable to administer deprenyl compounds by a route that minimizes metabolism to inhibitor compounds such as (-)-methamphetamine and (-)-amphetamine, while allowing metabolism to active compounds such as (-)-desmethyldeprenyl. Metabolism to an active compound can occur at the desired site of activity, e.g., in the target organ or area, e.g., the brain. Thus, prodrugs, which are metabolized to active compounds, are useful in the methods of the invention.

It has been found that certain deprenyl compounds have greater therapeutic efficacy (e.g., are effective at lower doses) when administered so as to decrease or prevent the "first-pass" effect. Accordingly, intraperitoneal or especially subcutaneous injection are preferred routes of administration. In preferred embodiments, a deprenyl compound is administered in divided doses. For example, a deprenyl compound can be administered by frequent (e.g., pulsed) injections, or by a controlled infusion, which can be constant or programmably varied as described above. In preferred embodiments in which a deprenyl compound is administered orally, the deprenyl compound can be formulated to reduce the amount of hepatic metabolism after oral administration and thereby improve the therapeutic efficacy.

In certain embodiments, the deprenyl compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J Physiol.* 1233:134); gp120 (Schreier et al. (1994) *J Biol. Chem.* 269:9090); see also K. Keinanen; M. L. Laukkanen (1994) *FEBS Lett.* 346:123; J. J. Killion; I. J. Fidler (1994) *Immunomethods* 30 4:273. In a preferred embodiment, the therapeutic compounds of the invention are formulated in liposomes; in a more preferred embodiment, the liposomes include a targeting moiety.

The following invention is further illustrated by the following example, which should in no way be construed as being further limiting. The contents of all references, pending patent applications and published patent applications, cited throughout this application are hereby incorporated by reference. It should be understood that the animal models for nerve cell rescue used in the example are accepted and that a demonstration of efficacy in these models is predictive of efficacy in humans.

The following non-limiting examples are illustrative of the present invention:

EXAMPLES

Example 1

This example demonstrates the loss of tyrosine hydroxylase immunopositive (TH+) neurons from the substantia nigra compacta (SNc) following the administration of NPTP and their rescue by deprenyl.

In the first part of the study, the time course of MPTP induced neuronal death was established as follows. MPTP (30 mg/kg/d) was administered i.p. to 8 week old isogenic C57BL mice (from the National Institutes of Aging colony at Jackson Laboratories, USA (C57BL/NNia)); (n=6/time period) for five consecutive days (total cumulative dose of 150 mg/kg). Mice were killed by anaesthetic overdose (pentobarbital) followed by perfusion with isotonic saline (containing 5% rheomacrodex and 0.008% xylocane) and 4% paraformaldehyde 5, 10, 15, 20, 37 and 60 days following their last MPTP injection. Dissected brains were immersed in 4% paraformaldehyde in 0.1 m phosphate buffer overnight and placed in 20% sucrose.

In the second part of the study, the rescue by deprenyl of TH+ SNc neurons from MPTP induced loss was demonstrated as follows. MPTP (30 mg/kg/d) was administered i.p. to 8 week old C57BL mice (n=6–8/treatment group) for five consecutive days (days −5 to 0;

total cumulative dose of 150 mg/kg). Three days following cessation of MPTP administration (day 0), mice were treated with saline, deprenyl (Deprenyl Canada) (0.01, 0.25 or 10 mg/kg i.p.) or Clorgiline (Sigma Chemical Company, U.S.A.) (2 mg/kg) three times per week. Deprenyl administration was withheld until day 3 to ensure that all mice were exposed to comparable levels of MPP+ and that all MPTP and its metabolites had been eliminated from the central nervous system. Doses of deprenyl were chosen to reflect those used in studies demonstrating that deprenyl can prolong the lifespan of the rat and inhibit MAO-B activity by approximately 75% but have no effect on MAO-B activity (0.25 mg/kg) or cause inhibition of both MAO-B and MAO-A (10 mg/kg) (Knoll, J. Mt. Sinai J. Med. 55, 67–74 (1988) and Knoll, J. Mech. Ageing Dev. 46, 237–262 (1988), Demarest, R. T. and Azzarg A. J. In: Monoamine Oxidase: Structure, Function and Altered Function (T. P. Singer, R. W. Von Korff, D. L. Murphy (Eds)), Academic Press, New York (1 979) p. 423–430). A dose of 0.01 mg/kg deprenyl was also chosen; at this dose less than $10^{-7}$M will reach the brain tissue. As a further control, mice were treated with only deprenyl and were not administered MPTP. Mice were killed by anaesthetic overdose (pentobarbital) followed by paraformaldehyde perfusion 20 days following their last MPTP injection.

For both parts of the study, brains were bisected longitudinally along the midline and the half brains were glued together using Tissue-Tek so that surface landmarks were in longitudinal register. The glued brains were frozen in −70° C. methylbutane and then 10 $\mu$m serial sections were cut through the entire longitudinal length of each SNc.

Alternate sections were processed for TH immunocytochemistry using a polyclonal TH antibody as the primary antibody and a standard avidin-biotin reaction (ABC kit, Vector Labs) with diaminobenzidine (DAB) as the chromogen for visualization as generally described in Seniuk, N. A. et al. Brain Res. 527, 7–20 (1990) and Tatton, W. G. et al. Brain Res. 527, 21–32 (1990) which are incorporated herein by reference, and modified as follows. Slide-mounted sections were incubated with unlabelled primary TH antisera (Eugene Tech) in 0.2% Triton/0.1M phosphate buffer at 4° C. overnight. Tissues were washed with phosphate buffer then incubated for 1 hour with biotinylated goat anti-rabbit IgG secondary antibody followed by avidin-HRP incubation. A 0.05% solution of DAB in 0.01% hydrogen peroxide was used to visualize the immunoreactive somata. For comparative optical density measurements, sections from control and MPTP-treated brains were mounted on the same slide to reduce the effect of slide to slide variability in the assay procedure and were processed for immunocytochemistry.

Figure 2:
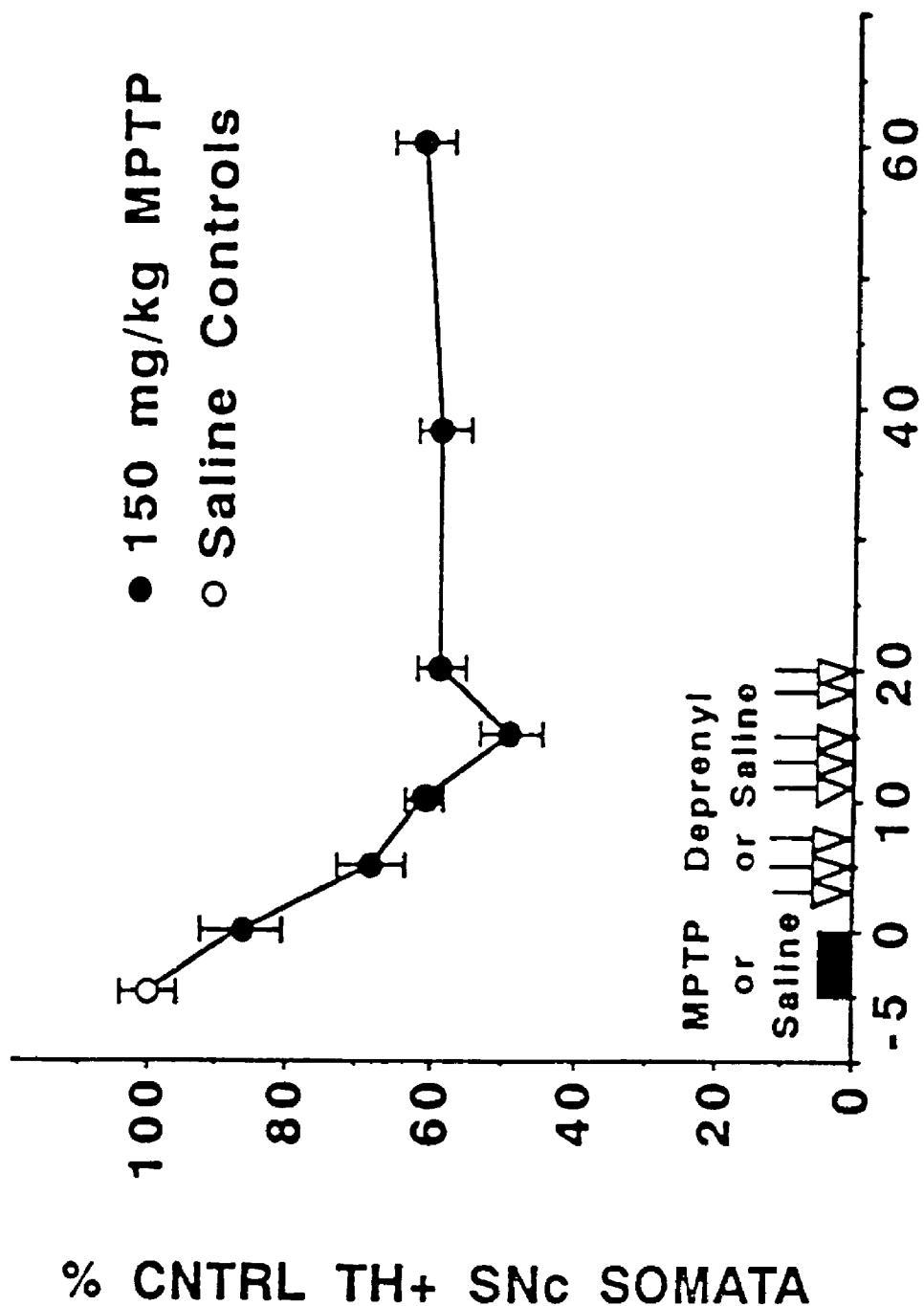
FIG. 2 is a graph showing the numbers of tyrosine hydroxylase immunopositive (TH+) neurons in the substantia nigra compacta (SNc) following the administration of MPTP.

The number of TH+ SNc neurons was obtained by counts of number coded alternate serial sections through each entire nucleus. Sections were recounted by multiple blind observers to check any observer bias. The values were corrected for section thickness (Konigsmark, B. W. In: Nauta, W. H., Ebesson S. O. E., ed., Contemporary Research Methods in Neuroanatomy, New York, Springer Verlag, p. 315–380, 1970). The mean value plus or minus the standard error of the mean was computed for the saline injected control mice. Subsequent data was then expressed as a percentage of this mean number as shown in FIG. 2.

Intervening sections were Nissl stained to define nuclear outlines (See Seniuk et al., Brain Res. 527: 7, 1990; Tatton et al. Brain Res. 527:21, 1990 which are incorporated herein by reference). The paired half sections for the glued half brains insured that any differences in neuronal numbers in the experimental and control groups were not due to different penetration or exposure to the antibodies or the reagents.

On 20 randomly-chosen half sections through the length of each nucleus for each animal, the region containing TH+ somata was traced using a camera lucida attachment to the microscope and the outline was then transposed to the immediately adjacent Nissl section using local histological features for landmarks (each nucleus usually included about 90 pairs of sections). The numbers of Nissl somata containing a nucleolus within the outline were counted according to three size groups (small—140 to 280 $\mu$m$^2$, medium—300 to 540 $\mu$m$^2$ and large—540 to 840 $\mu$m$^2$), excluding glial profiles (40 to 100 $\mu$m$^2$), using criteria similar to those of the rat SNc (Poirier et al. 1983 Brain Res. Bull. 11:371). Numbers of TH+ somata were plotted against numbers of Nissl somata for the corresponding areas of 20 immediately adjacent sections. The joint Nissl/TH+ counts provide a means for determining whether reductions in the numbers of TH+ SNc somata are due to neuronal destruction or a loss of TH immunoreactivity by surviving neurons (see Seniuk et al. 1990, supra, for details as to rationale for the procedure).

Figures 3, 3A:
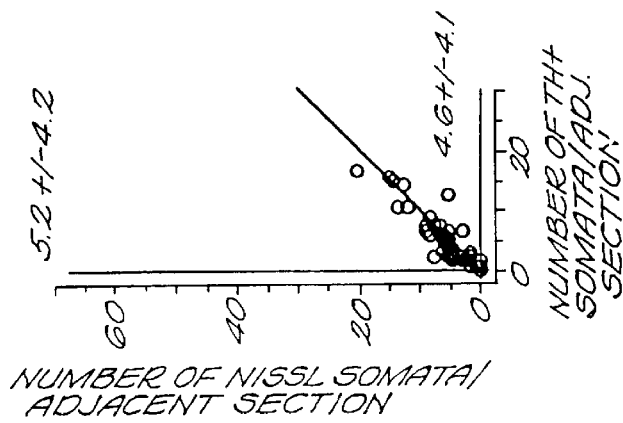
FIG. 3 are joint plots of the counts of TH+ and Nissl stained SNc somata from corresponding areas of immediately adjacent sections for Saline Only treated (A1, A2, A3), MPTP-Saline treated (B1, B2, B3) and MPTP-Deprenyl treated animals (C1, C2, C3) with the data pooled from 3 animals in each group at 20 days following the MPTP treatment.
Figures 2, 3A:
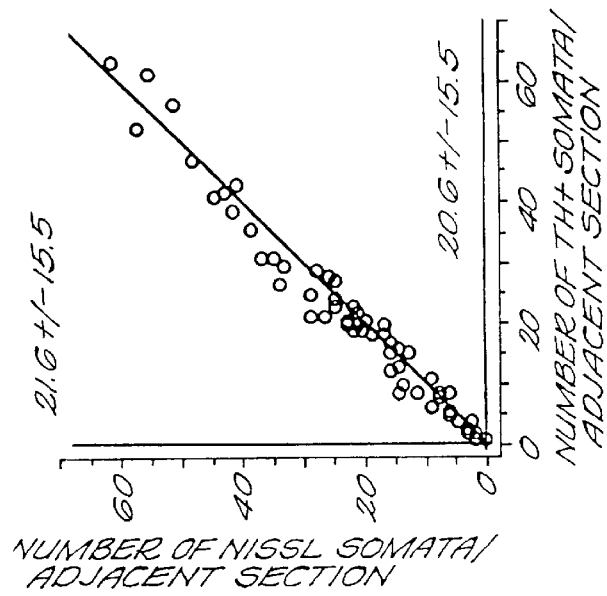
Figures 1, 3A:
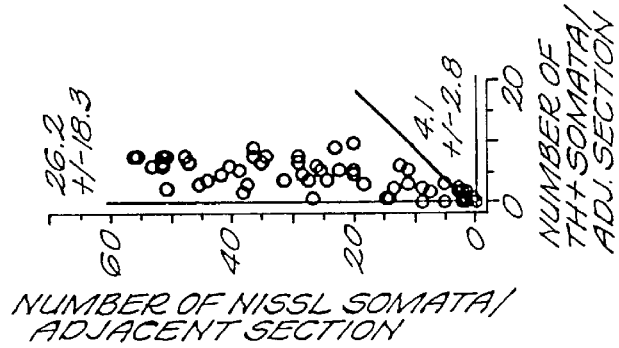

FIG. 3 shows a loss of TH+ somata from the SNc from days 0 to 20 post MPTP, with no decline thereafter. 20 to 30% of TH+ somata were lost by five days after completion of the injection schedule (day 5); loss of TH+ neurons continued over the next ten to fifteen days with no further disappearance thereafter. This continual loss of TH+ neurons could not be accounted for by the presence of MPTP or its toxic metabolite MPP+, due to its rapid elimination from the body (Johannessen, J. N. et al., Life Sci, 36, 219–224 (1985); Markey, S. P. et al., Nature, 311, 465–467 (1984); and Lau et al., Life Sci. 43, 1459–1464 (1988)).

Some neurons have the capacity to initiate repair following axonal damage, such as that seen with MPTP, by reactivating DNA transcription "programs" similar to those utilized by developing neurons to extend their axons or neurites (see Barron, K. V. in Nerve, Organ and Tissue Regeneration: Research Perspectives (ed. Seil, J.), 3–38 (Academic Press, New York, 1986). In the case of the TH+ SNc neurons, it would appear that a critical 20 day period exists in which these neurons either undergo effective repair and recovery following MPTP-induced damage or they die.

Joint plots of the counts of TH+ and Nissl stained SNc somata from corresponding areas of immediately adjacent sections in mice treated with saline only (values for three animals are pooled in FIGS. 3A1–A3) show that the numbers of TH+ somata are linearly related to the number of Nissl somata and are closely scattered around an equal value diagonal (illustrated by the diagonal lines in FIG. 3) for the medium-sized SNc somata (FIG. 3A2)) and the large-sized SNc somata (FIG. 3A3). In each plot in FIG. 3, the mean +/−1.0 standard deviation for the Nissl counts and the TH+ counts of somata per half section are shown at the upper end of each Y axis and the right end of each X axis respectively. For the medium and large somata the mean number of Nissl somata exceed the corresponding mean number of TH+ somata by 5–10% which appears to correspond to the percentage of nigrostriatal neurons which are not TH+(Van der Kooy et al. Neuroscience 28:189, 1981).

Figures 3, 3B:
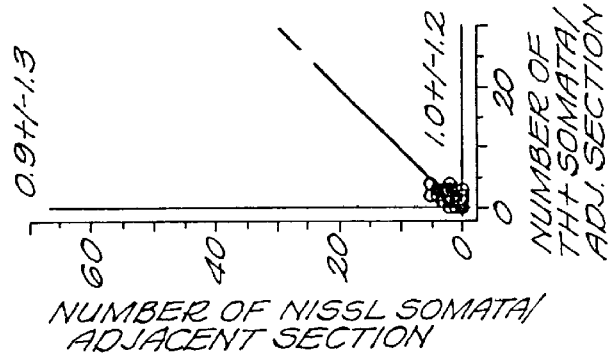
Figures 2, 3B:
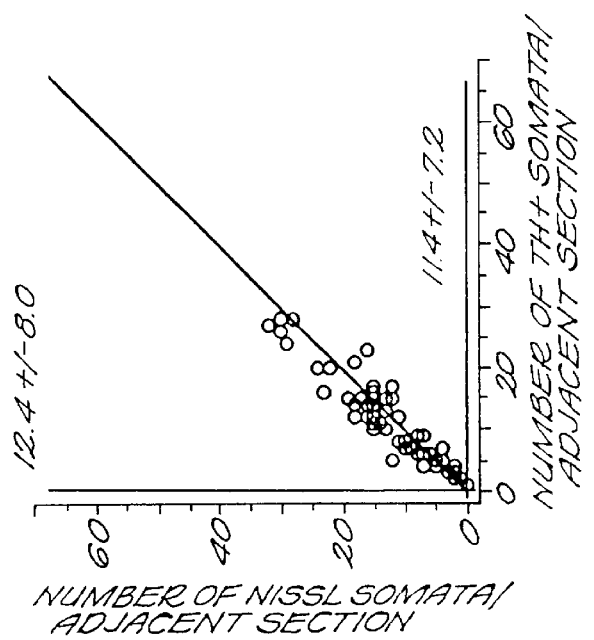
Figures 1, 3B:
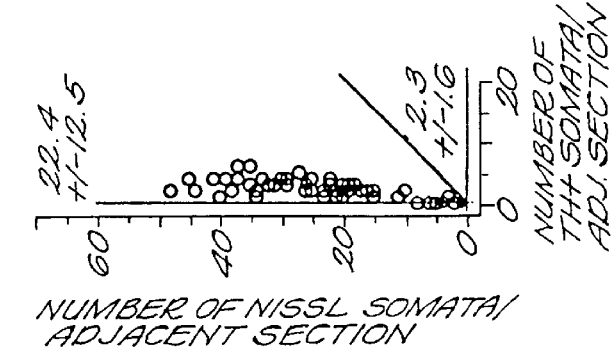

Joint counts of the small-sized SNc somata in the saline treated animals show that only a small proportion of the small neurons are TH immunoreactive and therefore dopaminergic (FIG. 3A1). These results are in keeping with previous findings in rodents which indicate that the large and medium sized somata are those of dopaminergic nigrostriatal neurons while the smaller somata are largely those of locally ramifying interneurons (Van der Kooy et al., 1981 supra; Poirier et al. Brain Res. Bull. 11:371, 1983). Joint Nissl/TH counts of somata in the animals treated with MPTP alone or MPTP followed by saline (values for three MPTP-saline animals are pooled in FIGS. 3B1, 3B2 and 3B3) confirmed that by 20 days after the completion of the MPTP treatment the loss of TH+ somata represented the death of SNc neurons rather than a loss of TH immunoreactivity in surviving neurons. FIG. 3B2 and 3B3 show that even though the counts of Nissl and TH+ somata are reduced from 21.6+/−15.5 and 20.6+/−15.5 per section to 12.4+/−8.0 and 11.4+/−7.2 for the medium-sized and large-sized somata, respectfully (values are means +/−1.0 standard deviation), the almost equal value relationships between the counts were maintained. If the SNc neurons were losing TH immunoreactivity but not dying, the scatter of the joint plots would be expected to shift to loci above the equal value diagonal (Seniuk et al. Brain Res. 527:7, 1990). Furthermore, FIG. 3B1 shows that the numbers of small-sized Nissl stained somata decreased slightly (26.2+/−18.3 to 22.4+/−12.5 per section) in accord with the reduction (4.1+/−2.8 to 2.3+/−1.6 per section) in the TH+ component of the small-sized SNc somata. If some of the losses of medium and large sized SNc somata were due to atrophy so that their cross-sectional areas no longer fell within the medium and large size ranges in response to the MPTP treatment, one would expect an increase in the numbers of small sized Nissl stained somata.

Figure 4C:
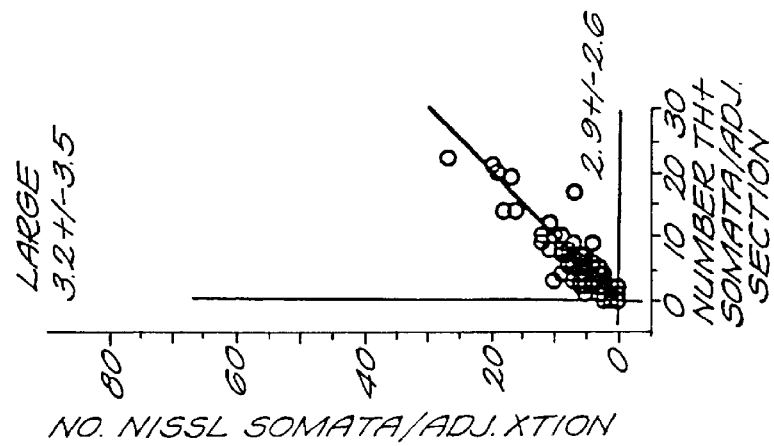
FIG. 4 are joint Nissl/TH+ plots for days 0, 3, 5, 10, 15 and 20 for pooled saline controls.
Figure 4B:
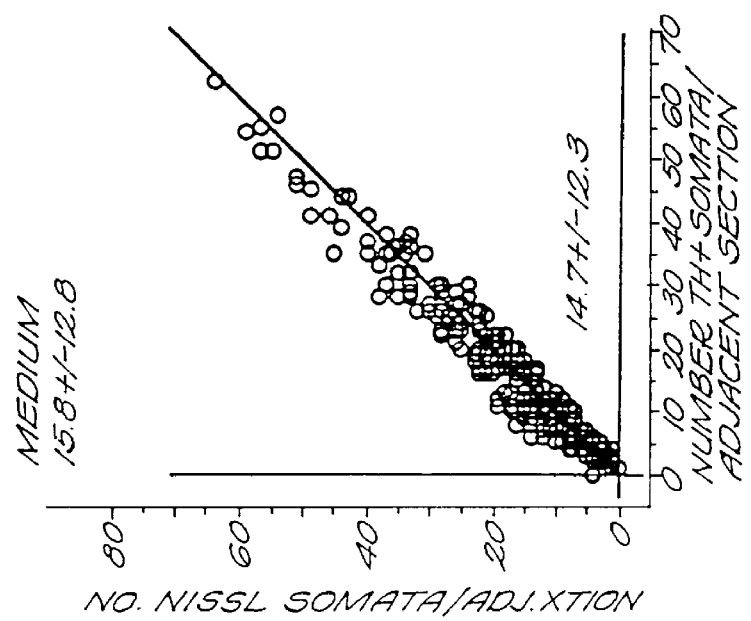
Figure 4A:
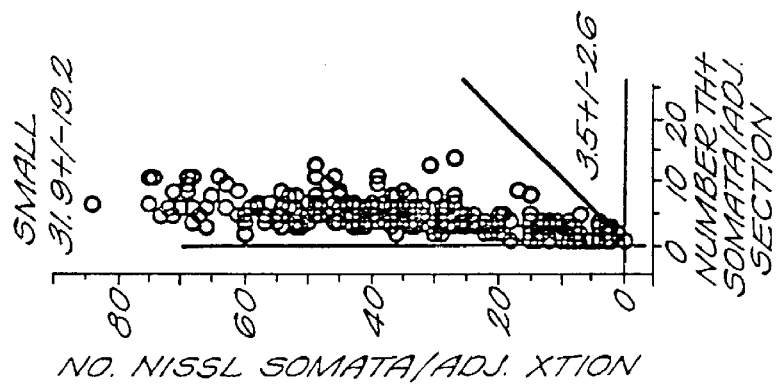
Figure 5A:
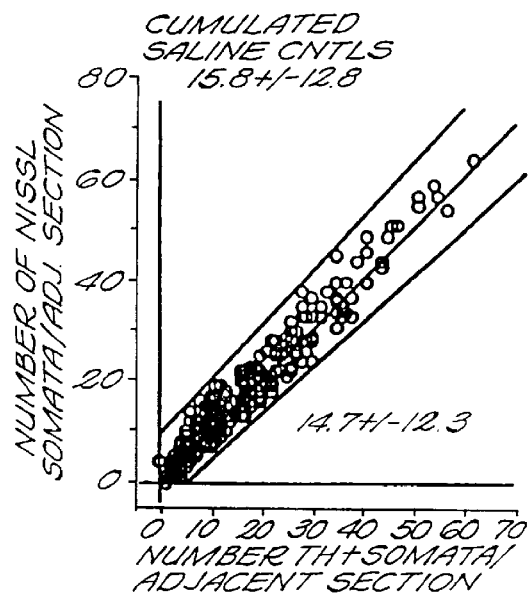
FIG. 5 are joint Nissl/TH+ plots for cumulated saline controls and for days 0, 5, 10, 15, and 20 after completion of MPTP treatment.
Figure 5B:
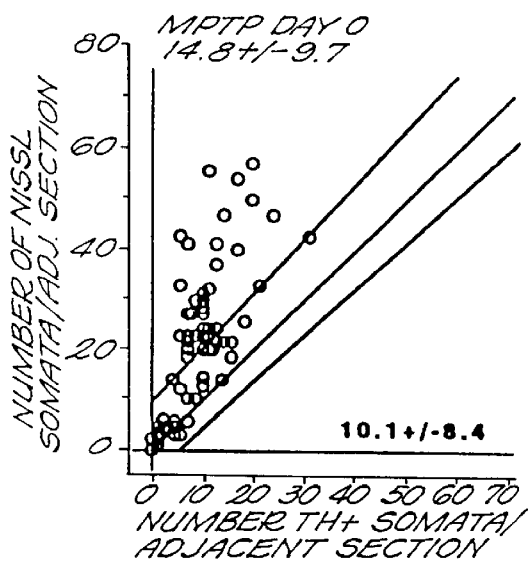
Figure 5C:
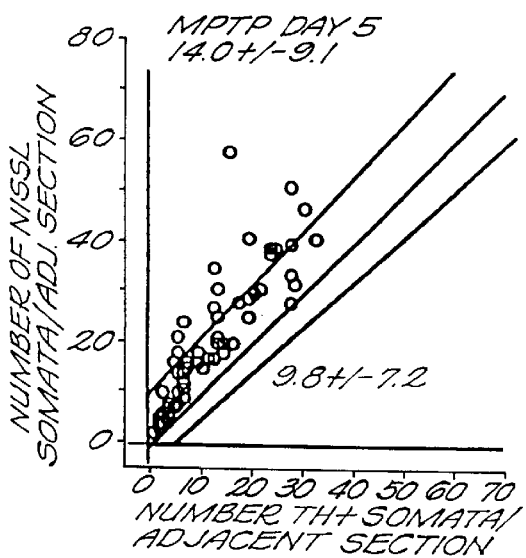
Figure 5D:
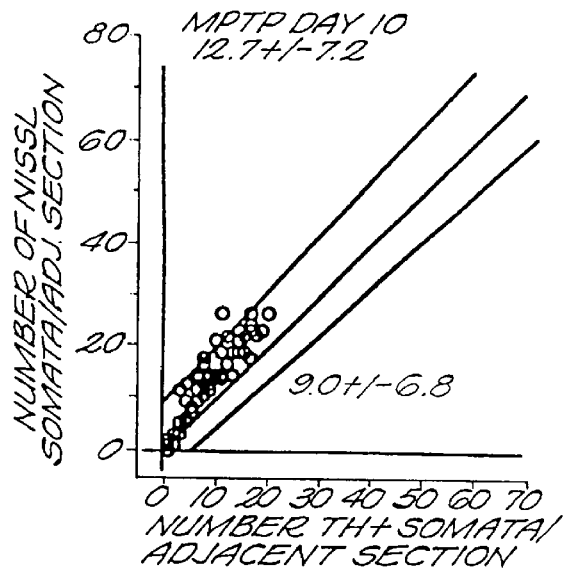
Figure 5E:
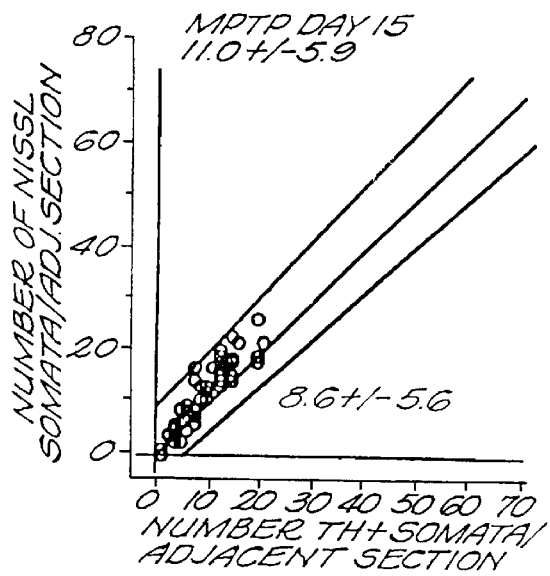
Figure 5F:
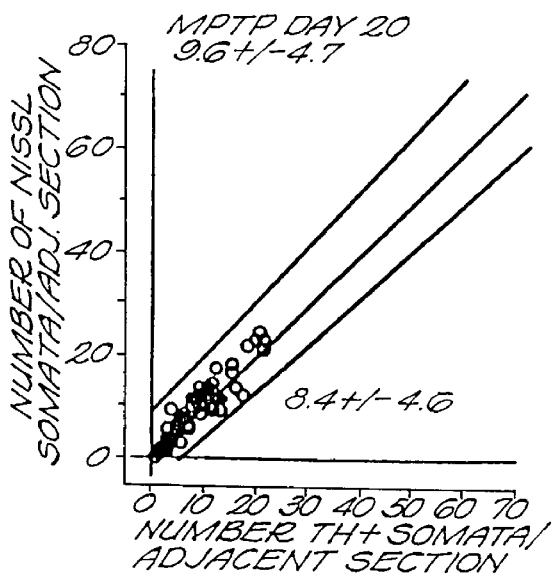

Joint Nissl/TH+ plots for days 0, 3, 5, 10, 15 and 20 after completion of the MPTP treatment and for the ssline controls are shown in FIGS. 4 and 5.

FIG. 4 represents Nissl/TH plots for the three major size groups of SNc somata in is rodents (small cross sectional somal areas, 140–280 $\mu$m$^2$, medium cross sectional somal areas, 300–540 $\mu$m$^2$ and large cross sectional somal areas, 540–840 $\mu$m$^2$) for the saline control animals. The data was pooled for saline controls sacrificed at days 0, 3, 5, 10, 15 and 20 after completion of the MPTP exposure. As previously shown, the joint Nissl/TH+ plots for the small SNc somata largely fall above the equal value diagonal (mean values of 31.9+/−19.2 per section for Nissl counts and 3.5+/−2.6 for TH+ counts) since most of the small somata are those of non-dopaminergic neurons. In contrast, the medium and large somata which are known to be largely dopaminergic cluster closely about the equal value diagonal (Nissl mean/section of 15.8+/−12.8 and TH+ mean/section of 14.7+/−12.3 for the medium-sized somata and Niss1 mean/section of 3.2+/−3.5 and TH+ mean/section of 2.9+/−2.4 for the large-sized somata). Hence for the saline controls the great majority of medium sized and large-sized Niss1 stainable somata are also TH immunoreactive.

FIG. 5 shows that at Day 0 (the final day of the MPTP exposure), a major proportion of plots for the medium-sized somata (medium-sized somata account for more than 90% of the dSNc neurons) fall above the equal value diagonal and above the range of the points established for the saline treated animals. This indicates that a significant proportion of the medium-sized dSNc neurons have lost detectable TH immunoreactivity but have not yet died at Day 0 (compare the mean Niss1 counts/section for the pooled saline controls of 15.8+/−12.8 to that for the Day 0 MPTP exposed of 14.8+/−9.7 showing that 14.8/15.8 of the medium sized somata are still present at Day 0). Gradually for days 5 through 20 the locus of the points return to within the band established for the saline controls while the extent of the points along the equal value diagonal shrinks toward the origin of the plots. That progressive change in the loci of the points in the joint Niss1/TH+plots indicates that the neurons are gradually dying over the 20 day period so that by day 20 all of the surviving medium-sized neurons have detectable TH immunoreactivity.

Figure 6:
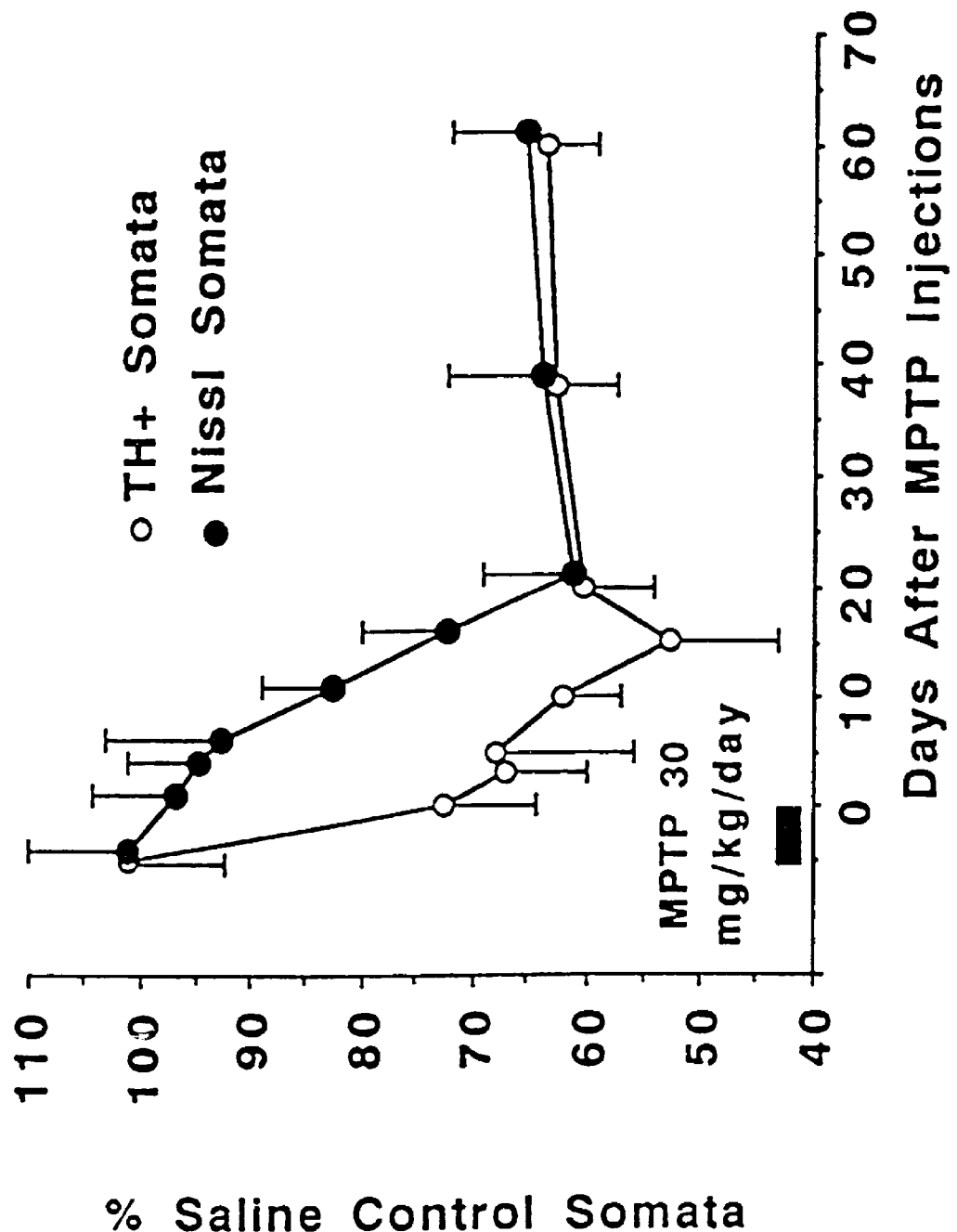
FIG. 6 shows superimposed plots for the percentage of Nissl stained somata and the percentage of TH+ immunoreactive somata relative to the mean values for the saline controls for Day 0 through Day 60.

FIG. 6 shows superimposed plots for the percentage of Niss1 stained somata and the percentage of TH immunoreactive somata relative to the mean values for the saline controls for Day 0 through Day 60. The difference between the TH immunoreactive percentages and the Niss1-stained percentages demonstrates the percentage of dSNc neurons which are sufficiently damaged to suspend TH synthesis but have not died due to the toxin. Hence at Day 3, when the deprenyl treatment was initiated, an average of 37% of the dSNc somata had lost detectable TH immunoreactivity but only 4% had died. The two plots converge between days 15 and 20 when the percentage of TH immunoreactive somata is not different from the number of Niss1 stainable SNc somata. The difference between the two plots can be taken to estimate the percentage of severely damaged dSNc neurons that are potentially rescuable at each time point after MPTP exposure.

According to the superimposed plots in FIG. 6, 84% of the dSNc neurons that died by days 15–20 could potentially be rescued at Day 3. Hence, since it was found that deprenyl rescued 66% of that 84%, deprenyl treatment in fact rescued 79% of the neurons that had not died before therapy was initiated.

Figure 7:
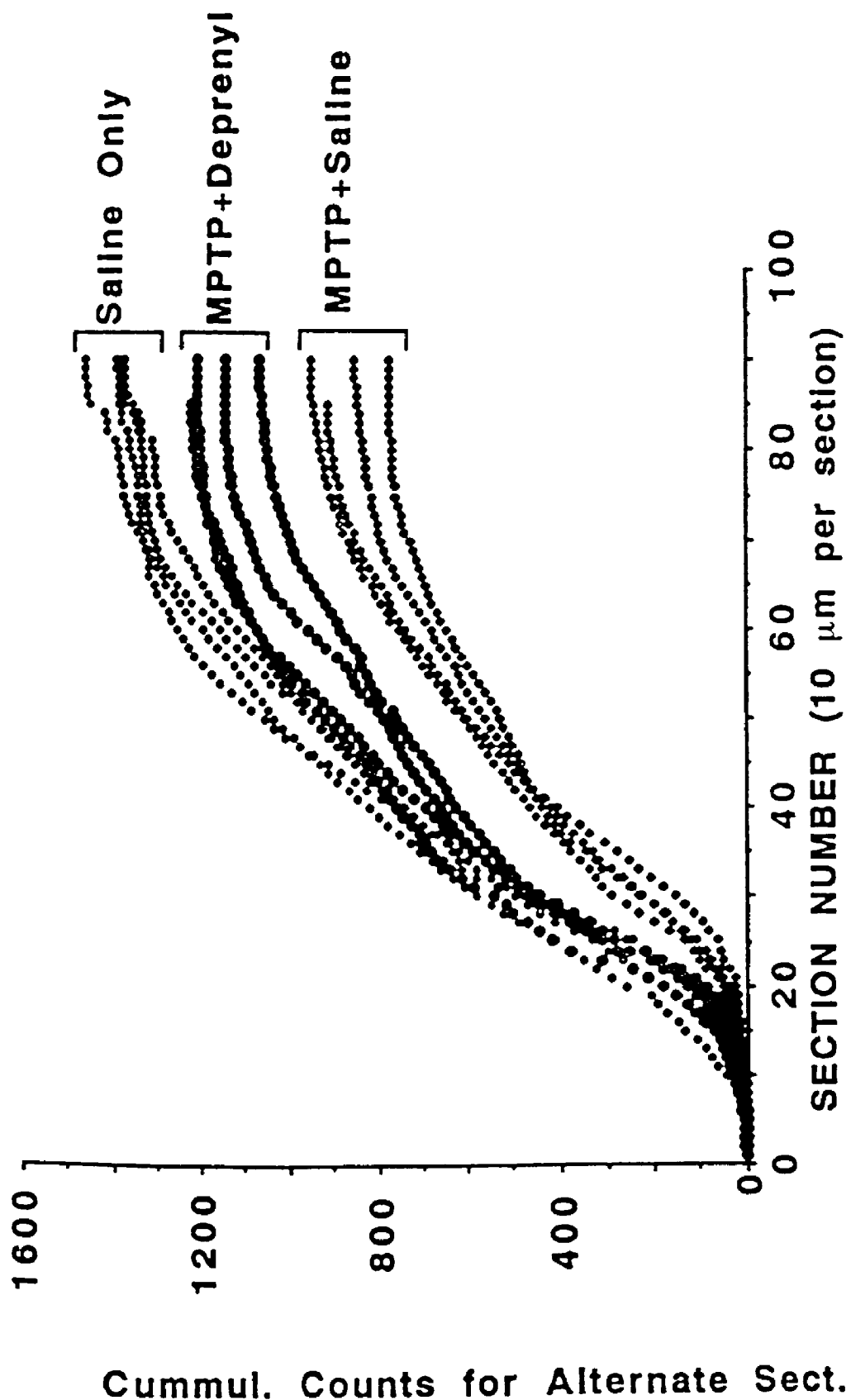
FIG. 7 is a graph showing the cumulative counts of TH+ SNC neurons versus section number for individual representative SNc nuclei taken from alternate 10 micron serial sections throughout the entire nucleus.
Figure 8:
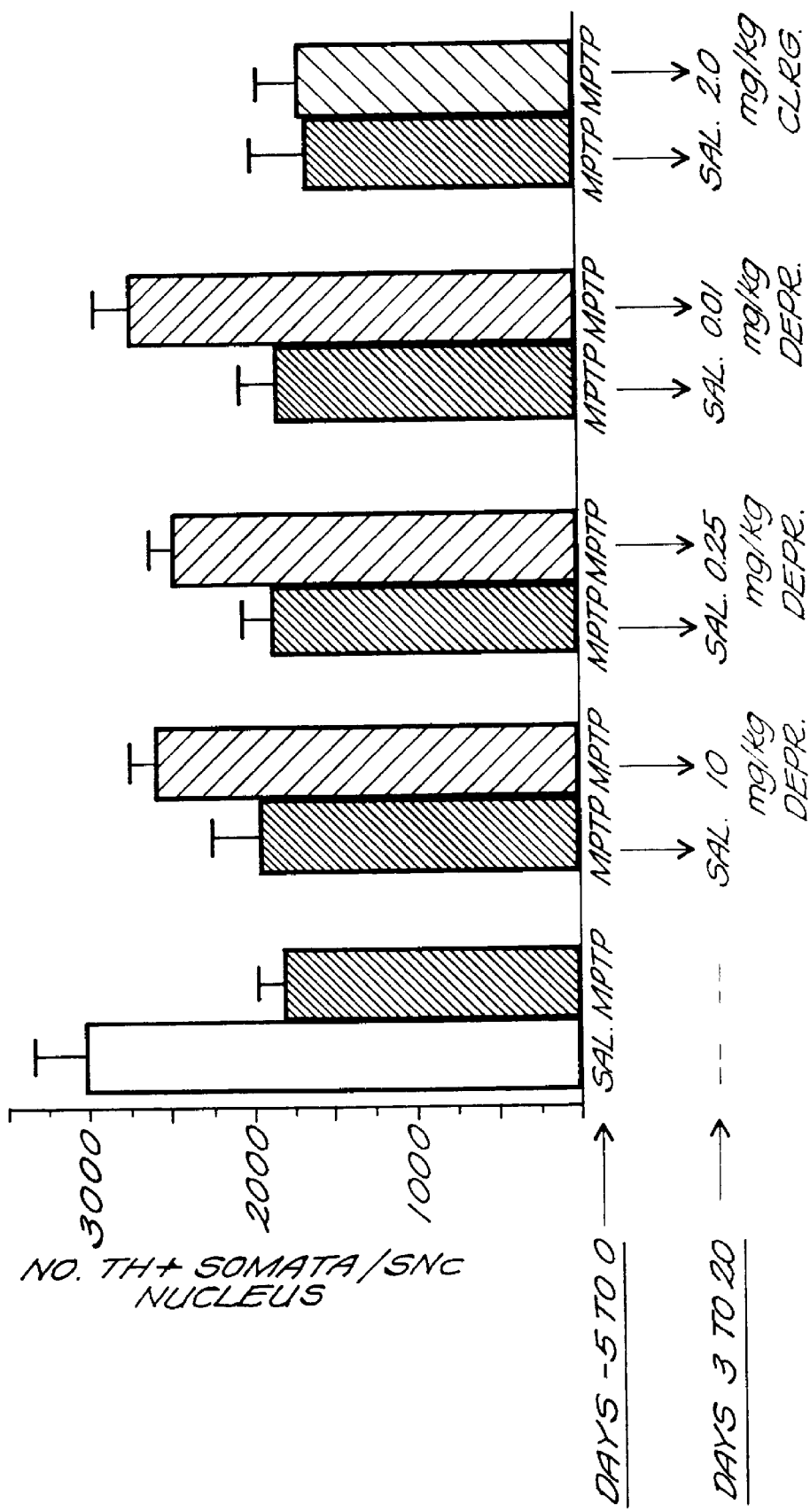
FIG. 8 is a graph showing the mean and SEM values for the MPTP, MPTP-Saline and MPTP-deprenyl treated mice.

FIG. 7 presents the raw counts of TH+ SNc somata for individual SNc nuclei taken from alternate 10 micron serial sections throughout the entire rostro-caudal length of each nucleus and expressed as a cumulative frequency distribution. Four representative trials for each treatment are presented in FIG. 7. Values for neuronal counts from mice treated with saline alone, MPTP (150 mg/kg) and saline and MPTP plus deprenyl (0.25 mg/kg, 3 times per week) are shared with those presented in histogram fashion in FIG. 8. As shown in FIG. 8, the cumulative frequency distribution curves for all SNc nuclei (n=4/treatment group) have a similar pattern indicating that the loss of TH+ somata following MPTP and their rescue by deprenyl occurred in all parts of the nuclei, although it appears to be greatest in the rostral portion of the nuclei (sections 10–40) that contains neurons which are relatively more resistant to the toxin. FIG. 8 also illustrates that there is no overlap in individual frequency distribution curves between the three groups of animals.

Figure 9A:
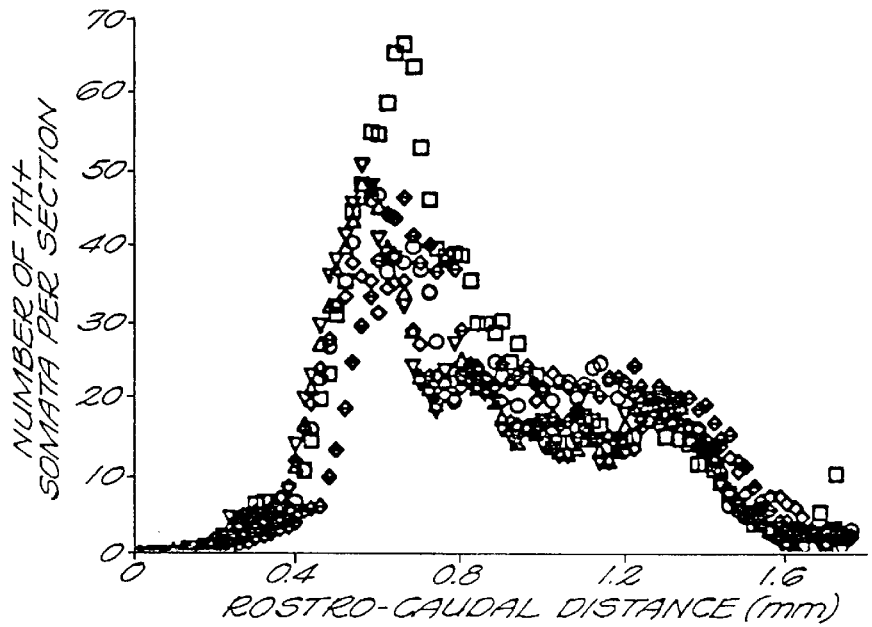
FIG. 9 is a graph showing TH+ somal counts for SNC neurons along the rostrocaudal length of a nucleus.
Figure 9B:
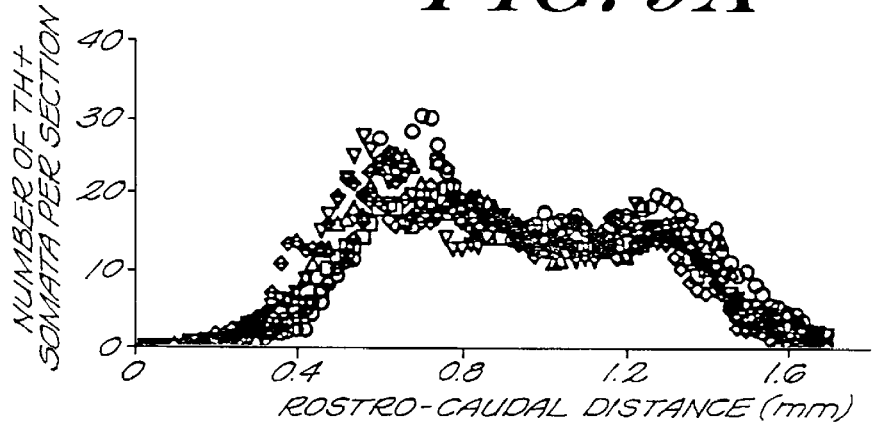
Figure 9C:
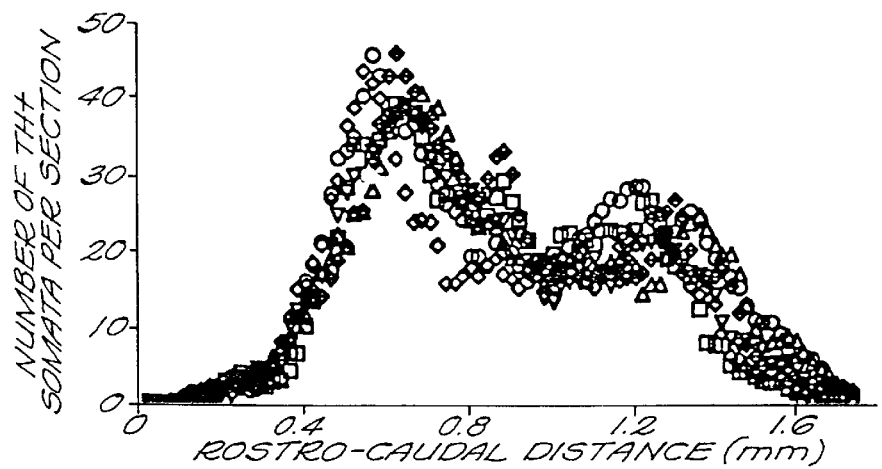

FIG. 9 shows TH+ somal counts for dSNC neurons along the rostrocaudal length of a nucleus. Rostrocaudal counts for 6 animals are superimposed in each panel. The area under each represents the total number of immunoreactive dSNC neurons and it shows the rescue by deprenyl.

Data shown in FIG. 8 represent the average number for all trials (n=6–8 mice/treatment group, i.e. 12–16 SNc nuclei) ±S.E.M. of TH+ somata/SNc nucleus. To obtain these values, raw counts of TH+ somata were converted to neuronal numbers using a correction factor of 2.15 as described by Konigsmark, B. W., in Contemporary Research Methods in Neuroanatomy (eds. Nauta, W. H. and Ebesson SOE) 315–380 (Springer Verlag, New York, 1970). FIG. 8 shows an increased number of TH+ SNc somata in the deprenyl treated mice relative to animals receiving MPTP alone, suggesting that deprenyl prevented a portion of the neuronal loss associated with MPTP-induced toxicity. Both low and high doses of deprenyl were equipotent in preventing the TH+SNc neuronal loss.

In particular FIG. 8 shows that the mean corrected numbers of TH+ somata found for animals treated with saline only of 3014+/−304 (mean +/−SEM) were significantly reduced (Mann-Whitney Test, $p<0.001$) in the animals treated with MPTP only (1756+/−161) and the MPTP-Saline groups (1872+/−187, 1904+/−308 and 1805±185). Therefore MPTP caused average losses of 36, 38 and 42% of TH+ somata in those three MPTP pretreated groups (black bars in FIG. 8). All the NPTP saline control groups are statistically the same ($p>0.05$). FIG. 8 also shows that Clorgyline, an MAO-A inhibitor, does not rescue the neurons since the MPTP-Saline (1706+/−155) and MPTP-Clorgyline (1725+/−213.6) values are statistically the same.

Deprenyl significantly increased ($p<0.005$) the number of TH+, SNc somata after MPTP to 2586+/−161 (14% loss), 2535+/−169 (16% loss) and 2747+/−145 for the 10, 0.25 is and 0.01 mg/kg doses respectively. Hence all doses of deprenyl reduced the loss of TH+ somata caused by the MPTP to less than 50% of the loss that was found when the MPTP was followed by saline, i.e., all three deprenyl doses produce similar and statistically significant ($p<0.001$) increases in neuronal numbers compared to the saline treated animals.

Figure 10:
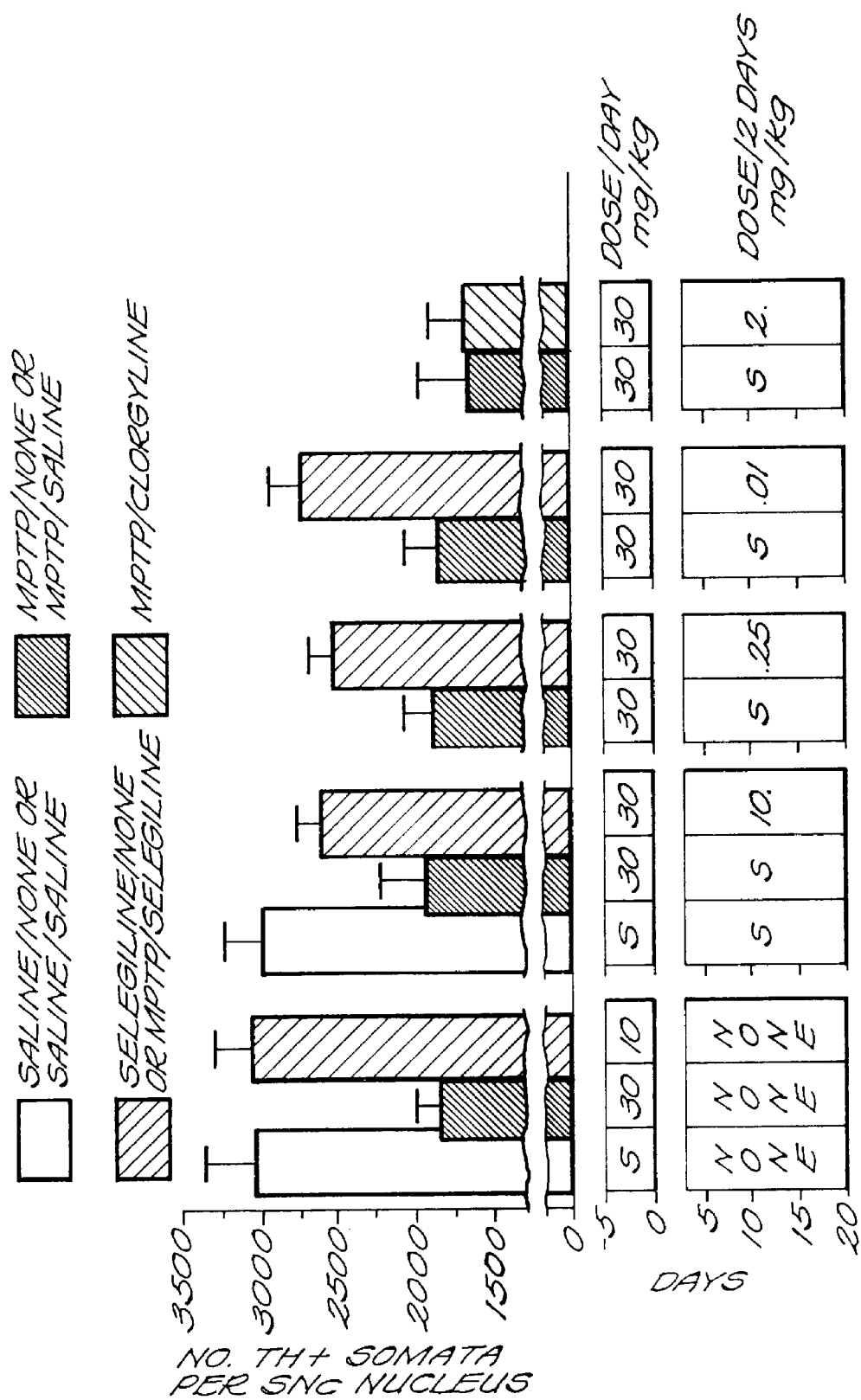
FIG. 10 is a graph showing the mean corrected number of TH+ somata for saline, MPTP, MPTP-saline, MPTP-clorgyline and MPTP-deprenyl treated animals with a table illustrating the timing of the various treatments.

FIG. 10 also shows the mean corrected number of TH+ somata found for animals treated with saline only, MPTP only, MPTP-saline, MPTP-clorgyline, MPTP-deprenyl with a table illustrating the timing of the various treatments. It also shows somal counts for animals only treated with deprenyl. Deprenyl alone does not alter the counts of TH+ somata in animals not previously exposed to MPTP.

The results illustrated in FIGS. 7 and 8 are even more striking when one considers the time-course of MPTP-induced loss of TH+ SNc neurons discussed above. By day five 75% of the TH+ SNc neurons which would die by day twenty had already lost their TH-immunoreactivity and only 25% of the TH+ SNc neurons which would die continued to lose TH-immunoreactivity between days 5 and 20. Assuming that the time course of neuronal loss was identical in the first and second part of the study, the numbers of TH+ SNc somata would have decreased from a mean of 3014 somata/nucleus to 2169 at day 3 and then further declined to an average of 1872 somata/nucleus by day 20. Deprenyltreated mice (0.25 mg/kg) had an average of 2535 somata/nucleus, thereby showing that deprenyl rescued all TH+ SNc neurons that would have died during the 17 days of administration and may even have rescued some TH+ SNc neurons which were no longer identifiable by TH+ immunocytochemistry.

Figures 3, 3C:
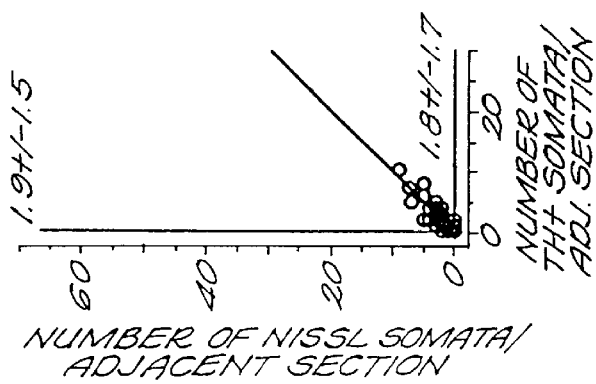
Figures 2, 3C:
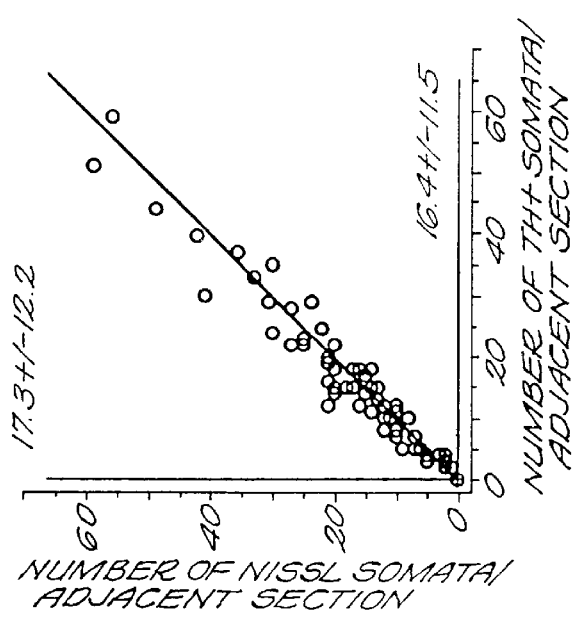
Figures 1, 3C:
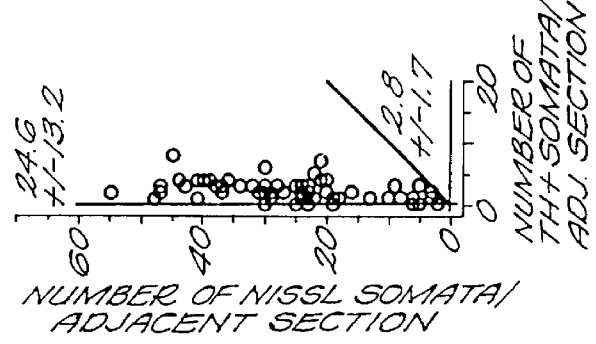

The joint Niss1/TH+ counts in FIGS. 3C1–C3 were plotted for pooled data from three animals treated with MPTP followed by 0.25 mg/kg doses of deprenyl. FIG. 3C2 shows a joint reduction in the loss of Niss1 and TH+ medium-sized SNc somata compared to that for the MPTP-saline animals (FIG. 3B2). There is a relatively smaller reduction in the loss of large-sized somata for the MPTP-deprenyl animals (FIG. 3C3) compared to that for the MPTP-saline animals (FIG. 3B3). The joint Niss1/TH+ plots establish that reduced loss of TH+ SNc somata in the MPTP-deprenyl treated mice is due to reduction in neuronal death rather than a reduction in the number of neurons which are not TH immunoreactive.

Example 2

MPTP-Mice were administered deprenyl (0.01 mg/kg or 0.25 mg/kg) following the procedure set out in Example 1. MAO-A and MAO-B measurements were obtained in accordance with the method set out below 24 hours after the first 0.25 mg/kg or 0.01 mg/kg deprenyl administration and 18 days later (corresponding to day 21 which would be just after the animals were sacrificed for the immunochemistry at day 20).

MAO activity was assayed in fresh tissue homogenates by the method of Wurtman, R. J. and Axelrod, J., (Biochem Pharmacol 1963;12:1439–1444), with a modification of substrates in order to distinguish between MAO-A- and MAO-B. This method relies on the extraction of acidic metabolites of either (14-C)-serotonin (for MAO-A) or (14-C) phenylethylamine (for MAO-B) in toluene/ethyl acetate. Tissue homogenates were incubated in potassium phosphate buffer containing either radiolabelled serotonin (100 micromolar) or phenylethylamine (12.5 micromolar) for 30 minutes at 37° C. The reaction was stopped by the addition of HC1 and acid metabolites extracted into toluene/ethyl acetate. Radioactivity in the toluene/ethyl acetate layer is determined by liquid scintillation spectrometry. Blanks are obtained from either boiled tissue homogenates or from reaction mixtures containing 5 enzyme (Crane, S. B. and Greenwood, C. E. Dietary Fat Source Influences Mitochondrial Monoamine Oxidase Activity and Macronutrient Selection in Rats. Pharmacol Biochem Behav 1987;27:1–6).

Figure 11:
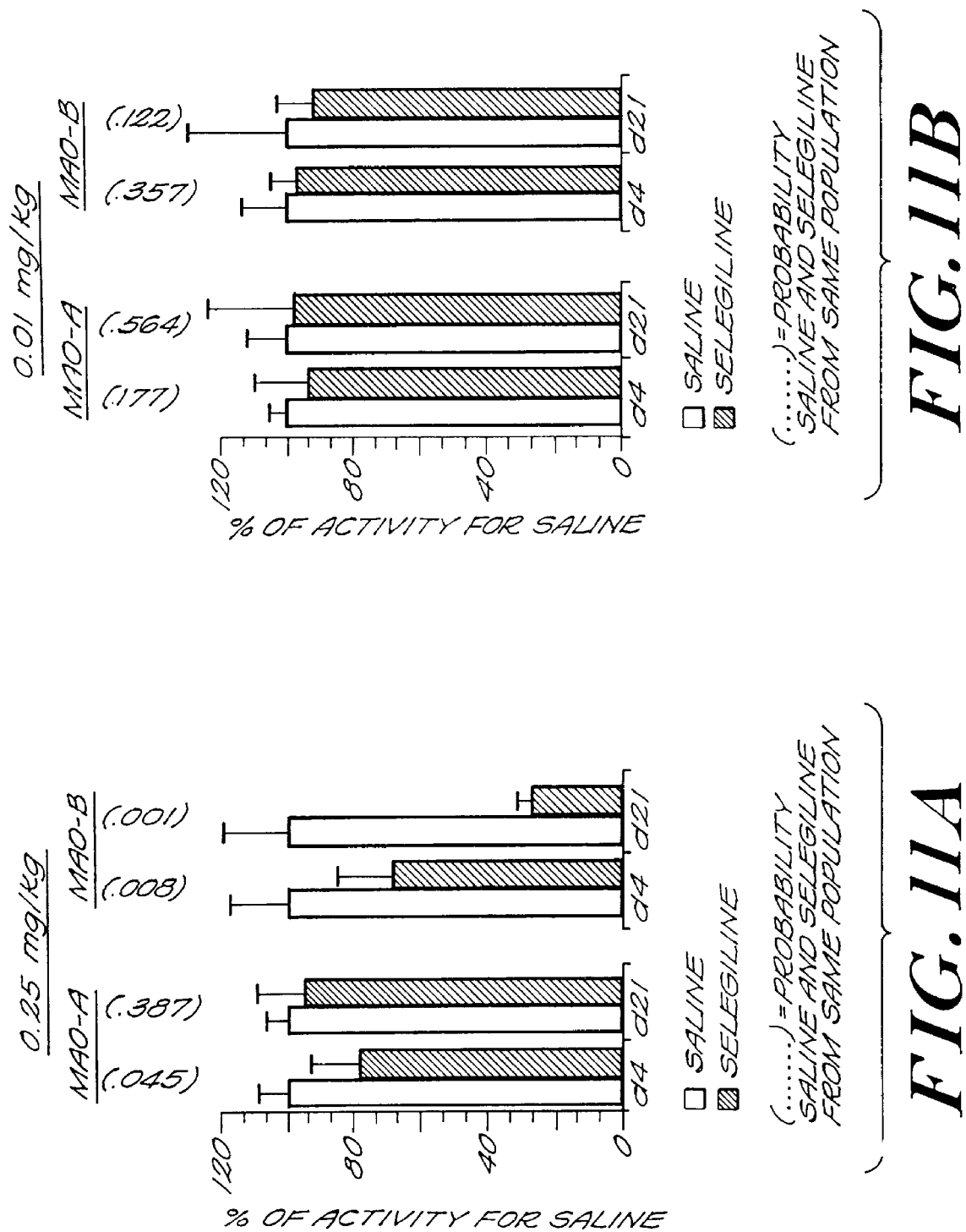
FIG. 11 is a bar graph showing MAO-A and MAO-B measurements at 24 hours (d4) after the first administration of deprenyl (0.25 mg/kg or 0.01 mg/kg) and 18 days later (d22)

FIG. 11 presents the MAO-A and MAO-B measurements for 24 hours after the first 0.25 mg/kg or 0.01 mg/kg and 18 days later (corresponding to day 21 which would be just after the animals were sacrificed for the immunocytochemistry at day 20). Hence since MAO-B inhibition (100%—MAO-B activity) would gradually increase over the 17 day treatment period, the two measures (labelled d4 and d22 to correspond to FIG. 2) give a picture of MAO-A and MAO-B activity at the beginning and end of the treatment period.

The KS probability shown in the brackets above each pair (saline and deprenyl treatment) represents the results of the Kolmogorov-Smirnov two sample non-parametric statistical testing (Siegel, S. Non Parametric Statistics for the Behavioral Sciences, McGraw-Hill Book Company, New York, 1956, pp. 127–136) to determine if the deprenyl-saline pairs are drawn from the same population. The probability value indicates the probability that the data comes from the same population. A value of $p<0.5$ is required to detect any significant differences and $p<0.01$ is preferable. Hence there is weak but detectable inhibition of MAO-A at d4 for the 0.25 mg/kg deprenyl dose which may be real since the MAO-B inhibitor may cause weak MAO-A inhibition at higher doses. The 0.25 mg/dose causes strong MAO-B inhibition at both d4 (72% activity, 28% inhibition) and d22 (31% activity, 69% inhibition). Ninety percent or more MAO-inhibition was required for anti-depressant effects but conceivably 28 to 69% MAO-B inhibition might mediate the rescue at deprenyl doses of 0.25 mg/kg.

Most importantly, the 0.01 mg/kg dose did not produce any significant MAO-A or MAO-B inhibition at d4 and d22. Hence the marked rescue with 0.01 mg/kg is equipotent to that with 0.25 mg/kg but cannot be due to MAO-B inhibition. Therefore, deprenyl may activate a receptor through a 3D structure which may not be related to the structure which blocks MAO-B.

Example 3

Male, C57BL/6J mice obtained at five weeks of age from Jackson Labs (Bar Harbor, is Maine) were housed in individual cages and allowed food and water ad libitum. Mice were given an initial two week acclimatization period to a 12:12 hour light:dark (LD) cycle in an isolated room kept at a constant temperature of 21° C. Subjective "day" began at 8:00 hours while subjective "night" began at 20:00 hours. Light levels were maintained at 200 lux during the subjective day. Locomotory movements were selectively quantified with a Stoelting Electronic Activity Monitor, individual sensor boxes being placed under each cage. Higher frequency signal interruption such as feeding or grooming events were not recorded. Locomotory movements for individual mice were continuously monitored under continual darkness (DD) or under LD conditions for 90 to 120 days. After approximately 20 days the mice were treated with twice daily injections for 5 days (pre injection days −5 to 0) of saline or MPTP (to achieve cumulative doses of 37.5, 75, 150 and 300 mg/kg). Injections were always given during the subjective day 0 the first injection occurring 4 hours after 'lights on' and the second, 4 hours before "lights off".

Spectral analysis (Bloomfield, P. Fourier Analysis of Time Seriess An Introduction; John Wylie and Sons: New York, 1976, Brigham, E. O. The Fast Fourier Transform; Prentice-Hall, New York, 1974, Marmarelis, P. Z.; Marmarelis, V. Z. Analysis of Physiological Systems The White-Noise Approach; Plenum Press: New York and London, 1978) of the locomotory activity was done with a SYSTAT statistical software program using fast Fourier transforms. Activity counts from periods just exceeding 240 hours (about 10 days) or 120 hours (about 5 days) were used. The number of samples were chosen to just exceed 128 or 256 in order to fulfill the rule of powers of 2. Before Fourier decomposition the activity values were treated with a split-cosine-bell taper to reduce leakage from strong components into other components. These values were then padded with zeros to 512 samples. The mean was then removed from these values and the Fourier transform was calculated for 100 lags to encompass hours/cycle values of 5.12 to 512. The magnitudes were sguared to determine the power of each component and the power for each hour/cycle value was expressed as a percentage of the total power.

Figure 12:
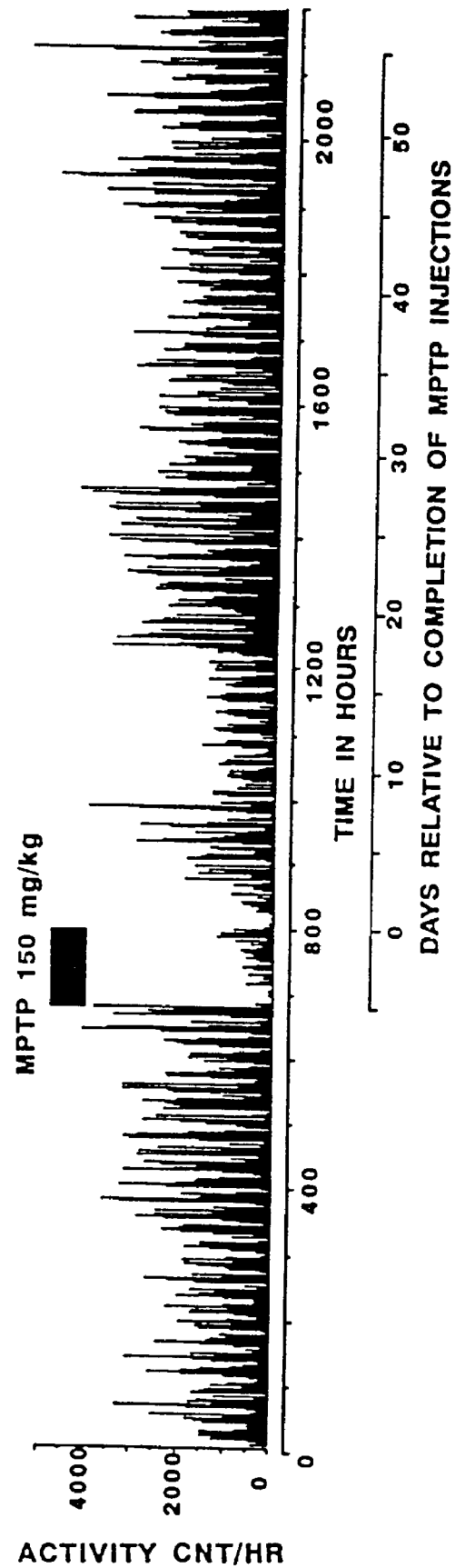
FIG. 12 shows a spectral analysis of locomotory activity for mice injected with MPTP.

Neurochemical assays were performed at 5, 10, 15 and 20 days following the last of the MPTP injections. The mice were sacrificed by cervical dislocation and the brain removed. Striatal tissue was dissected so as to include the nucleus accumbens and the caudate. The tissue was frozen in 2-methylbutane (Kodak) at −70° C. until their catecholamine concentrations were measured by reverse-phase ion-pair high performance liquid chromatography (HPLC) with electrochemical detection. Tissue samples were weighed, then homogenized in 0.2N perchloric acid containing dihydroxybenzylamine as internal standard and extracted onto alumina (Mefford, I. N. J. Neurosci. Neth. 1981, 3, 207–224). The catecholamines were desorbed into 0.1N phosphoric acid, filtered and injected onto an Ultrasphere ODS 5 micron column. The mobile phase contained 7.1 g/l $Na_2HPO_4$, 50 mg/l EDTA, 100 mg/l sodium octyl sulphate and 10% methanol. The detector potential was +0.72 versus a Ag-AgCl reference electrode. Interrun variability was approximately 5%. FIG. 12 shows 92 days of typical recording and the black bar indicates the interval of MPTP injection (150 mg/kg in total, 30 mg/kg daily for five days). Each vertical bar on the activity trace represents the sum of activity for one hour. Note that there is slower rhythm with a period between 100–200 hours superimposed on a faster (about 24 hour) circadian rhythm which introduces a cyclic variation into the amplitude of the activity peaks. The regularity of these patterns, as well as the amplitude of activity, was significantly affected during the MPTP injection period (675h–842h), but seemed to "recover" by 1200 hours, viz. between days 15–20 post-injection.

Figure 13A:
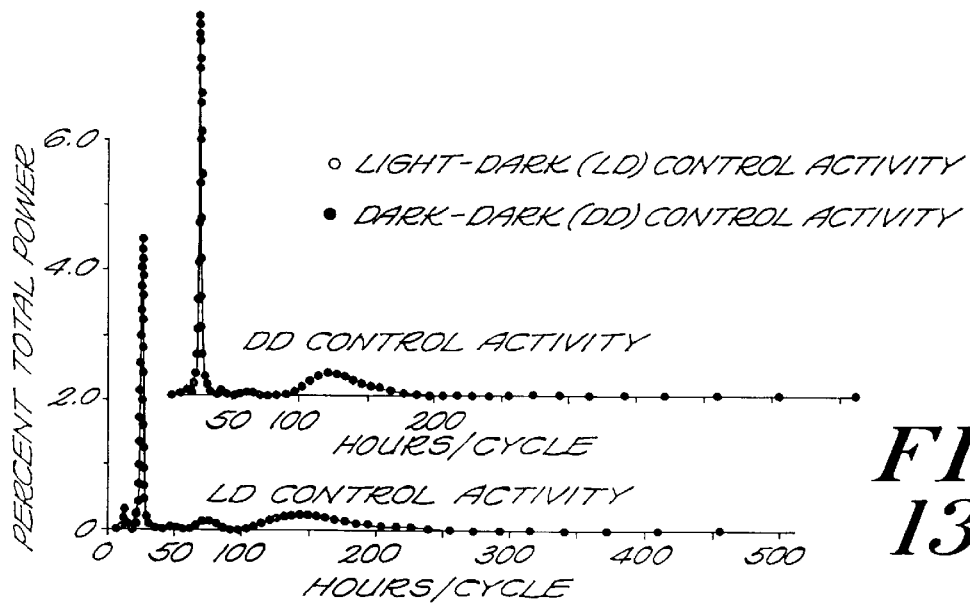
FIG. 13 shows high resolution power spectra for LD and DD preinjection control period from a saline injected mouse.
Figure 13B:
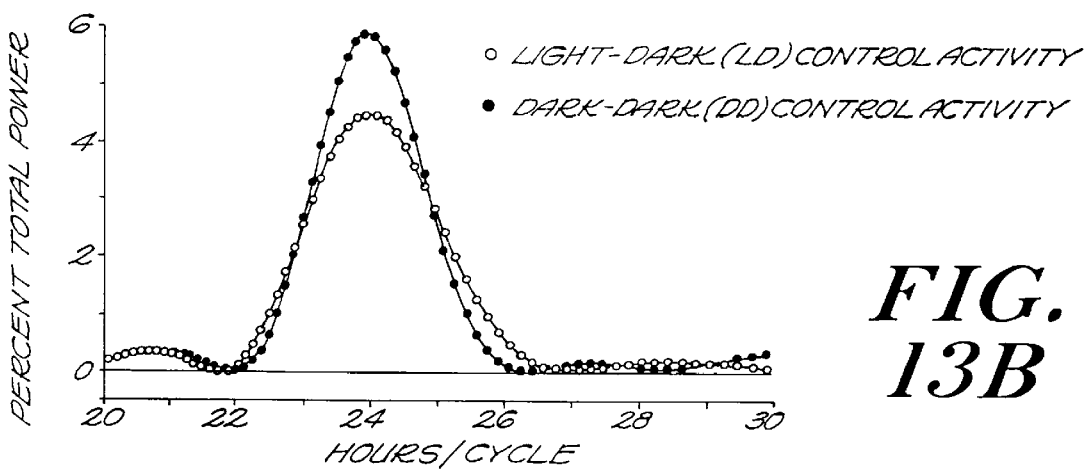
Figure 13C:
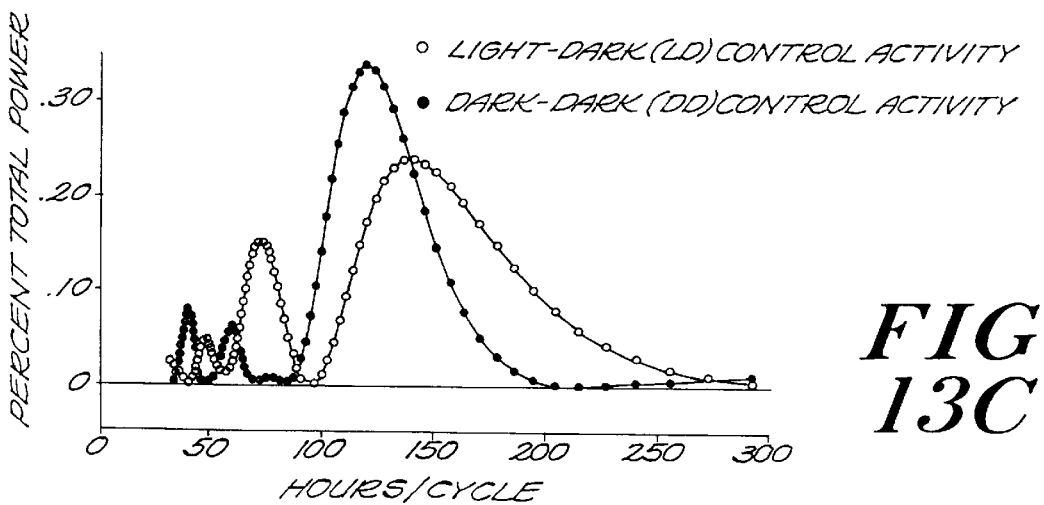
Figure 14A:
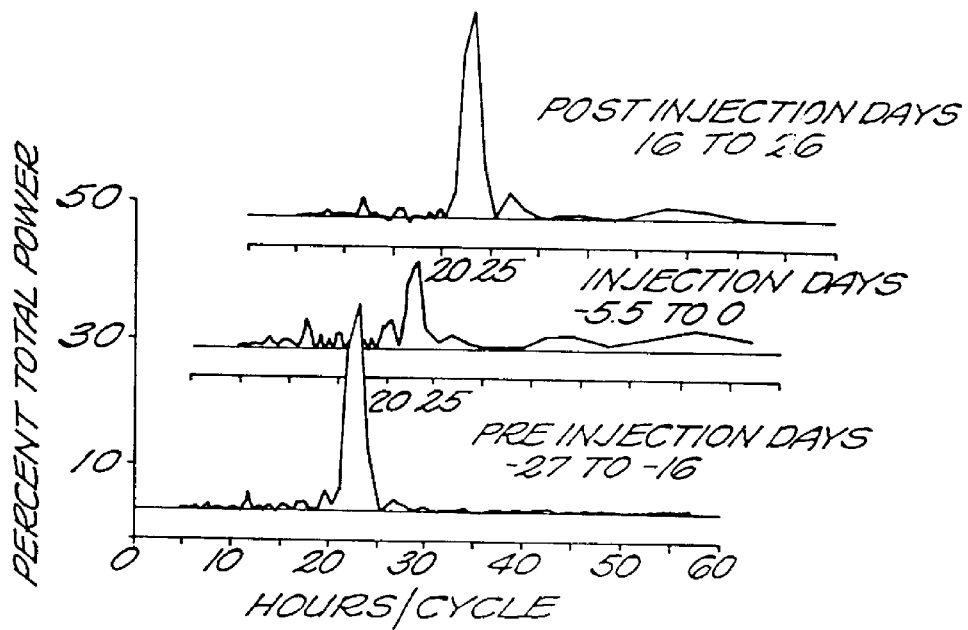
FIG. 14 shows a high resolution power spectra for control and MPTP mice.
Figure 14B:
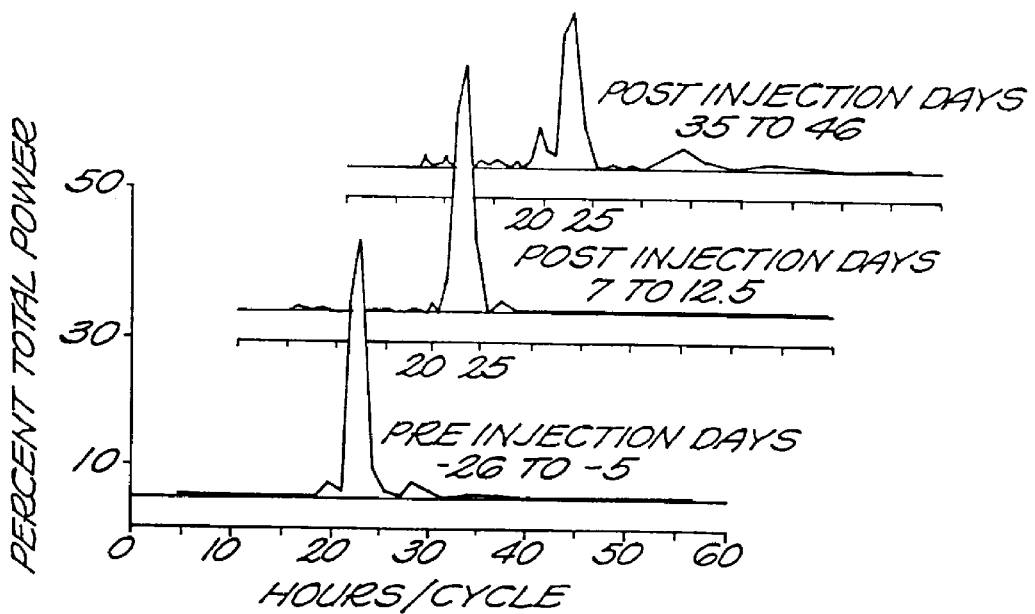
Figure 14C:
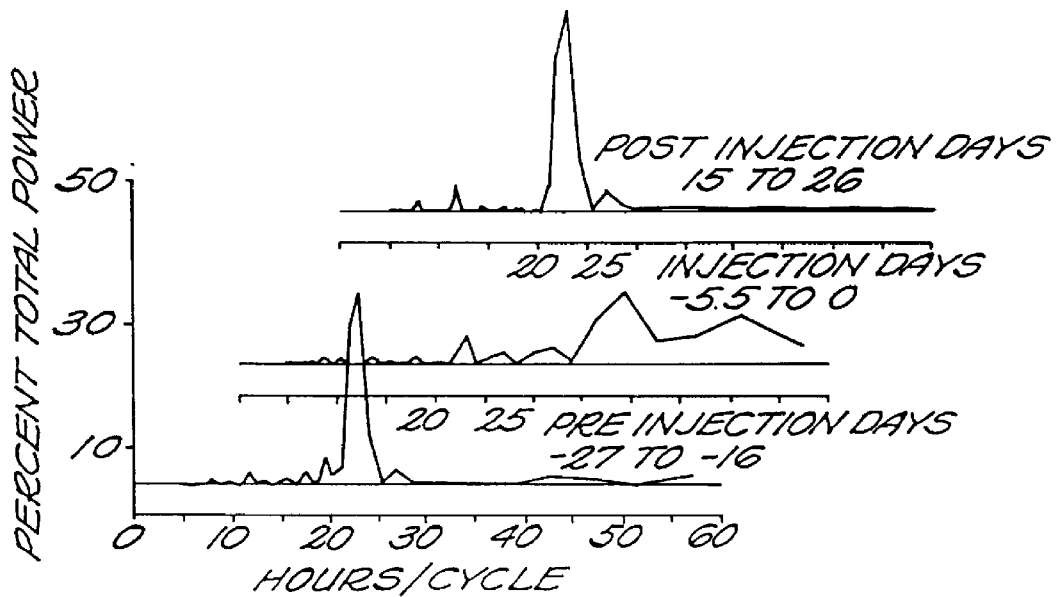
Figure 14D:
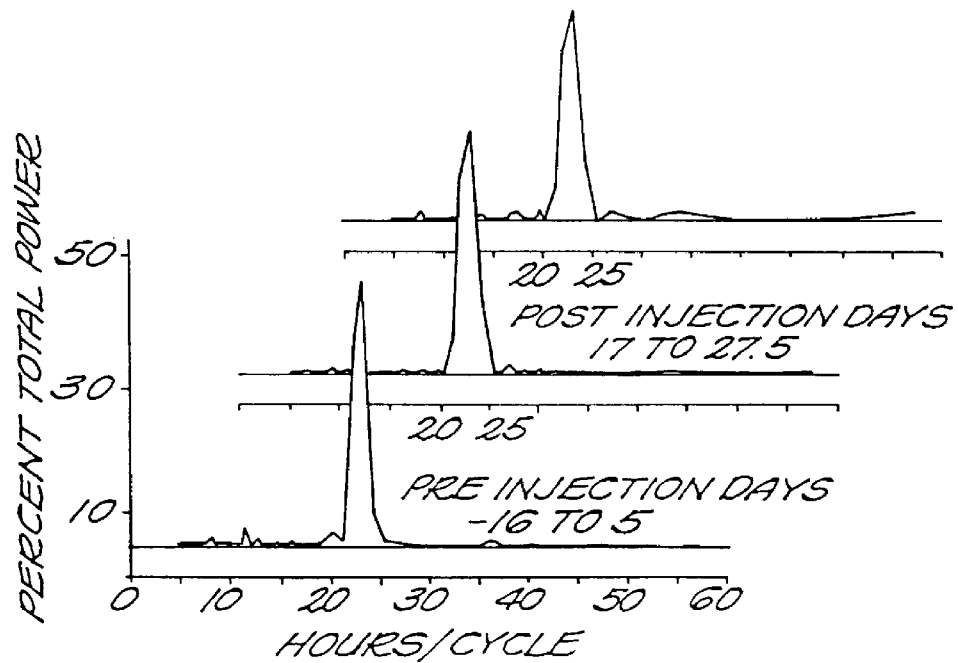

Analysis of the locomotory activity in the time domain was complicated by the superimposition of multiple endogenous activity cycles so that Fourier analysis was used to quantitate the data. High resolution power spectra for LD and DD preinjection control periods from a saline injected mouse are shown in FIG. 13. The spectra were calculated for 256 activity counts then padded to 4096 values with zeros before the Fourier transform was applied. In FIG. 13A, both LD and DD spectra display a major peak at approximately 24 hours/cycle which includes in excess of 75% of total power. Note the slight shift in the centroid of the DD peak to a cycle length which is approximately 9 minutes shorter than the LD peak. In FIG. 13B a secondary peak occurs between 100–250 hours/cycle which is consistent with previous observations from the raw data of FIG. 12. This peak is shifted by about 50 hours/cycle for the DD spectra as compared to the LD spectra. Longer hours/cycle values did not reveal any other peaks. Note that a third smaller peak arising only during LD entertainment occurs over 60–90 hours/cycle. The clear separation of the circadian peak from the slower peaks made it possible to independently evaluate the changes in the power of the dominant 24 hour component after MPTP treatment. The locomotory activity was therefore measured as the percentage power under the 22–26 hours/cycle peak.

In FIG. 14, panel A shows that interruption of the animals' endogenous activity by saline injections was sufficient to reduce the percentage power of the P22–26 relative to preinjection and post-injection days. Hence, activity changes like those in Panel B could not be reliably interpreted for the MPTP injection period. Saline injections did not produce any changes in the P22–26 in the post-injection period (Panel C for an example). In contrast, the 150 and 300 mg/kg doses (see FIG. 15) resulted in marked depression of the P22–26 which recovered by days 12 to 20 (Panels B and D).

Figure 15:
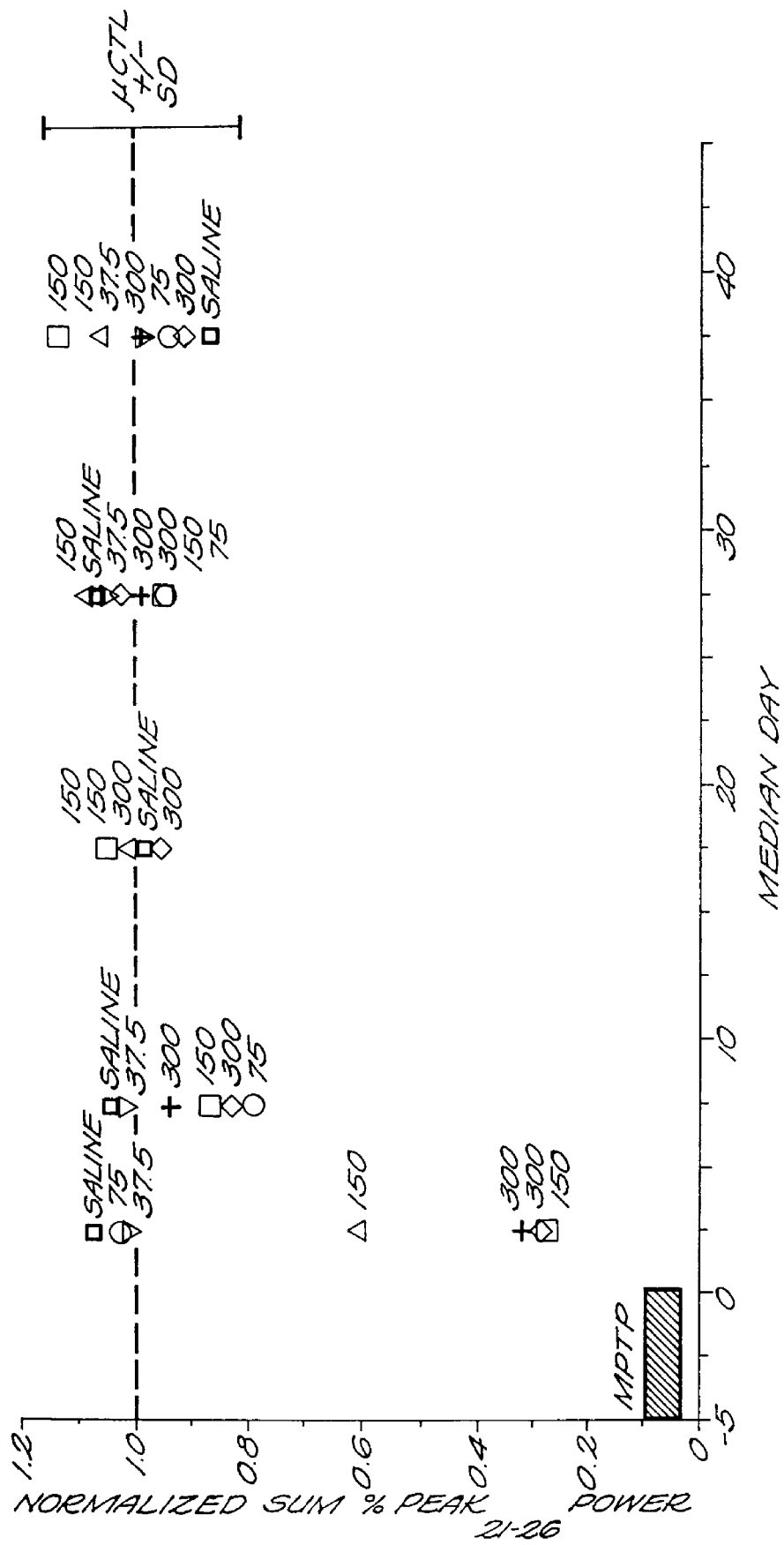
FIG. 15 is a graph showing the normalized sum % peak power versus median day.

FIG. 15 shows that saline and 37.5 or 75 mg/kg MPTP injections did not alter P22–26 locomotory activity significantly from that of the control pre-injection days (the error bar represents +/−1 s.d. for the pooled control activity). In contrast, peak power for the P22–26 was reduced to 20–60% of mean control values in the 5 days following 150 or 300 mg/kg MPTP treatment and returned to normal by median Day 20.

Figure 16A:
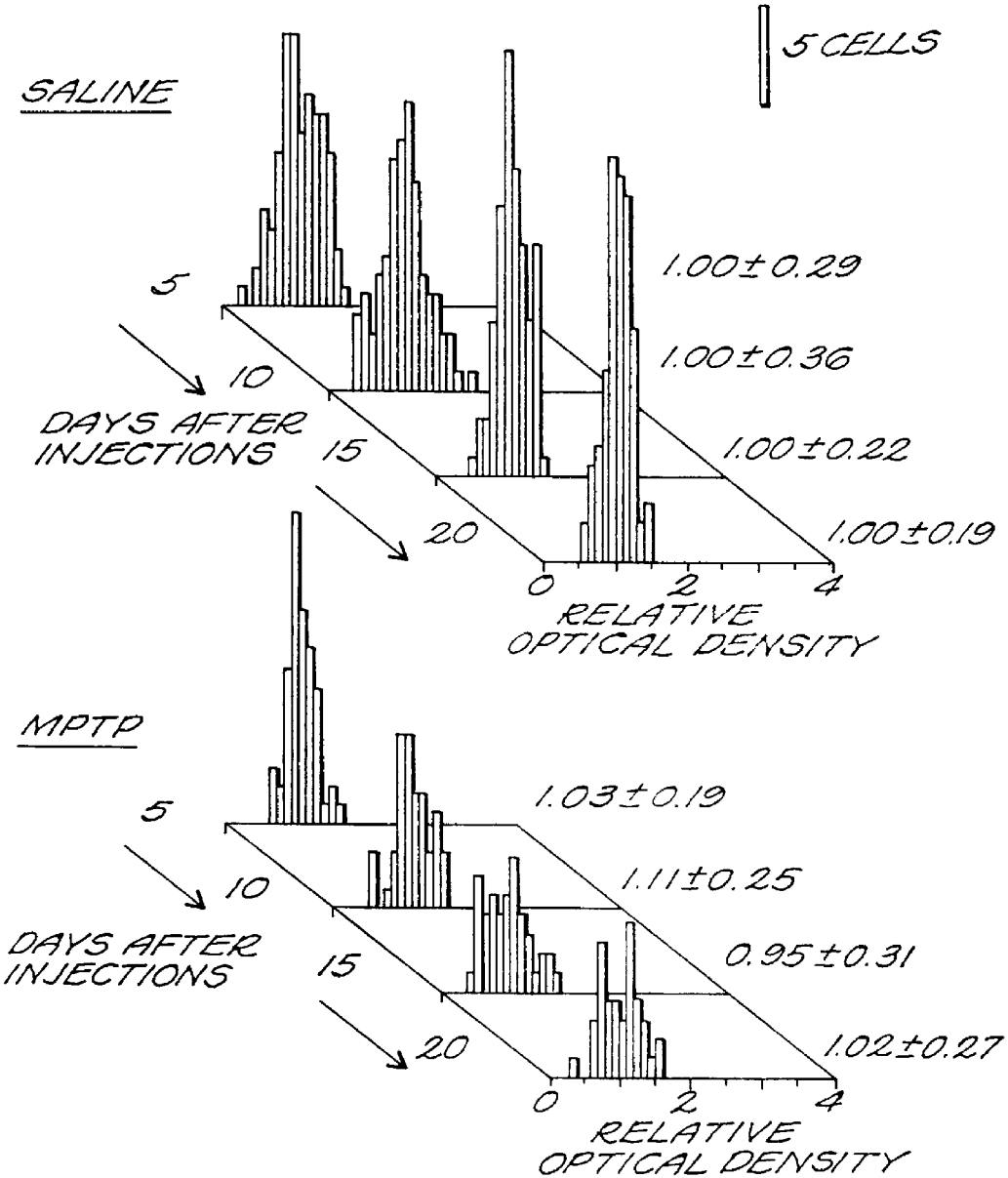
FIGS. 16A and 16B show SNc sections for glued brains from animals treated with MPTP or saline.
Figure 16B:
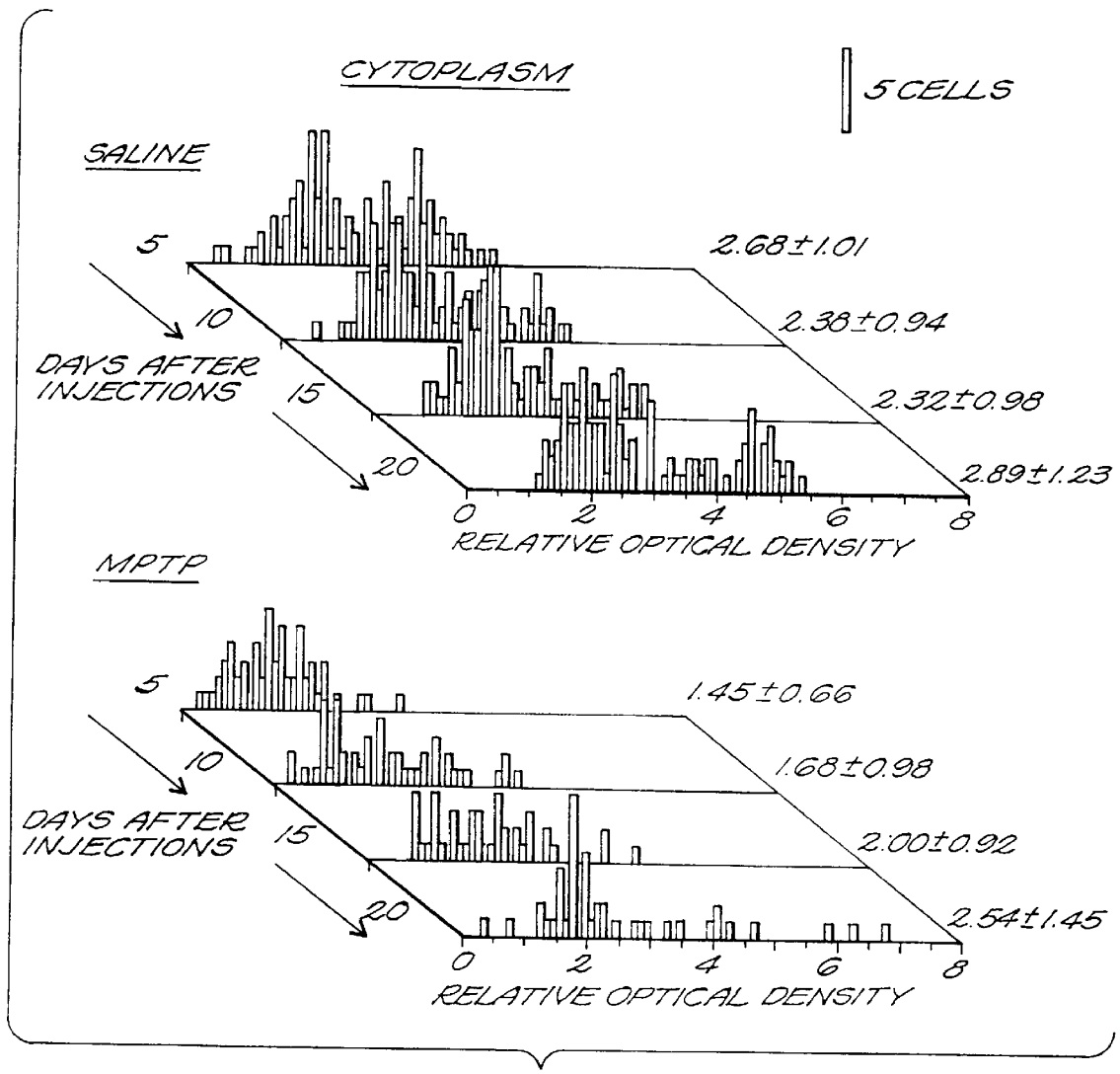
Figure 17A:
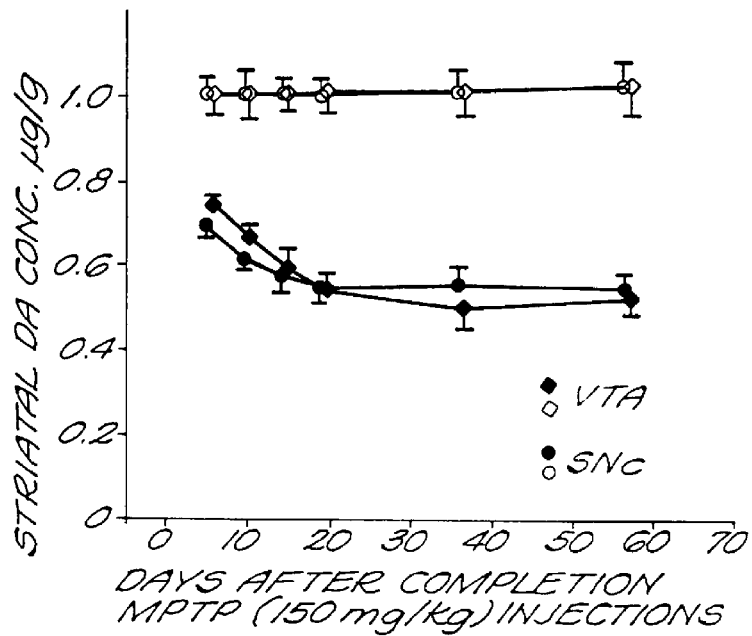
FIG. 17A, B, C, and D are graphs showing the counts of TH+, SNc and VTA neuronal somata following MPTP treatment taken through whole nuclei expressed as a percentage of the mean counts for the corresponding saline-injected animals (A); the concentration of striatal DA (B); the concentration of striatal DOPAC, and the DOPAC/DA ratio (D) for saline and MPTP injected mice.
Figure 17B:
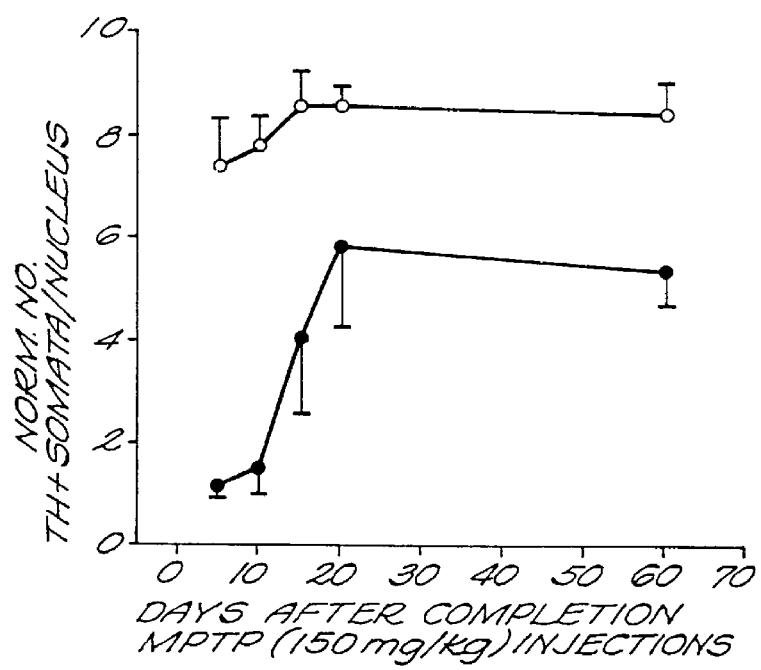
Figure 17C:
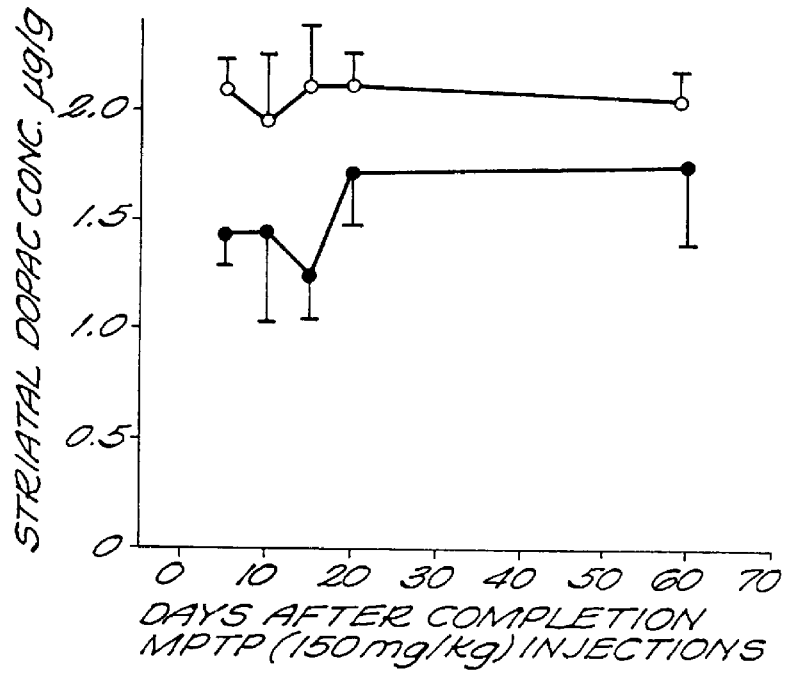
Figure 17D:
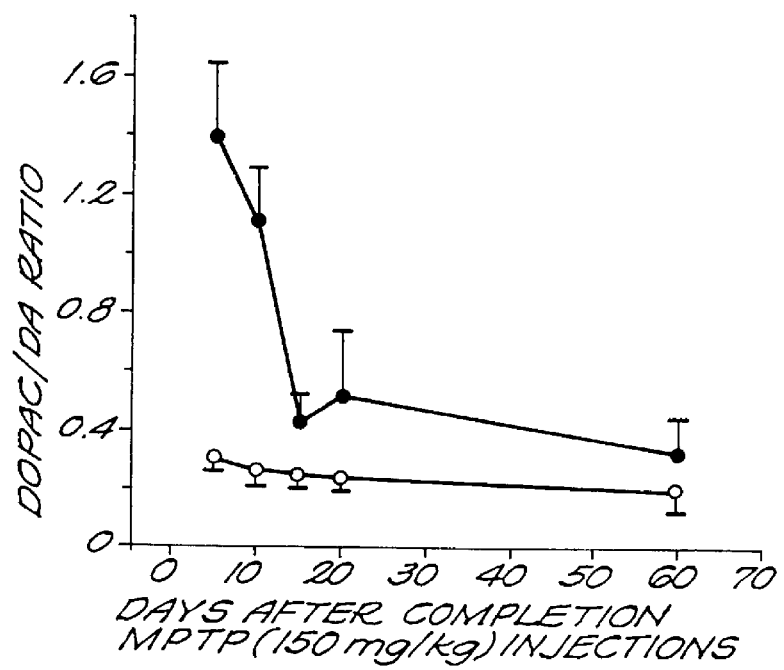

A second series of animals, treated with 150 mg/kg MPTP or saline, were sacrificed for TH immunocytochemistry and sections were visualized with avidin-conjugated horseradish peroxidase and diaminobenzidine at days 5, 10, 15, 20 and 60 following MPTP injection. The paraformaldehyde perfused brains were bisected along the midline and halves from a saline-injected and an MPTP-injected animal were glued together using Tissue-Tek so that surface landmarks were longitudinally in register. Serial 10 $\mu$m sections were taken through the brainstem to encompass an SNc from both animals so that SNc neurons from the saline and MPTP animals were immediately adjacent and were exposed to similar concentrations of the antibodies and reagents. Panel A and Panel B (FIG. 16) present SNc sections for glued brains at Days 5 and 20.

FIG. 17, Panel A presents the counts of TH+ SNc and VTA neuronal somata following NPTP treatment taken through whole nuclei expressed as a percentage of the mean counts for the corresponding saline-injected animals (error bars are s.d.). MPTP injected animals are represented by the filled symbols. Note the gradual decrease in the number of SNc somata with detectable TH immunoreactivity from Days 5 to 20 with an apparent maintenance of the number of TH+ somata after Day 20. Panels B, C and D present the concentration of striatal DA and DOPAC for the saline and MPTP injected animals. Note the similarity of the time course for the recovery of striatal DA concentrations toward normal levels with recovery of locomotory activity in FIG. 15. The DOPAC/DA ratio shows a marked increase and rapid decline over Days 5–10 for the MPTP injected animals and then maintains a constant level at about 2 times that of the saline injected animals.

A computer optical density (OD) system was used to measure somal cytoplasmic TH immunoreactivity and the background immunoreactivity in the immediately adjacent tissue for randomly chosen SNc and VTA somata (Tatton, W. G. et al. Brain Res. 1990, 527, 21–32) for the glued brain sections. Background OD per unit area was subtracted from somal OD per unit area for each cell to obtain an estimate of cytoplasmic TH immunodensity per unit area. The mean background OD for the saline injected half of each glued section was used to normalize the values for the MPTP background OD and the saline and MPTP cytoplasmic ODs. FIG. 17 presents distributions for the normalized background and cytoplasmic measurements for TH+ SNc somata at Days 5–20 after saline or 150 mg/kg MPTP injections. In this and other studies using the glued brains, background values did not differ significantly (p<0.05) for the saline injected and MPTP injected halves thereby allowing valid comparisons of the cytoplasmic values. The control distributions for the saline injected animals often revealed a bimodal distribution of TH immunodensity for the SNc somata ranging from 0.5 to 6 times mean background levels with modes at about 2 and 4 times mean background level.

Figure 18A:
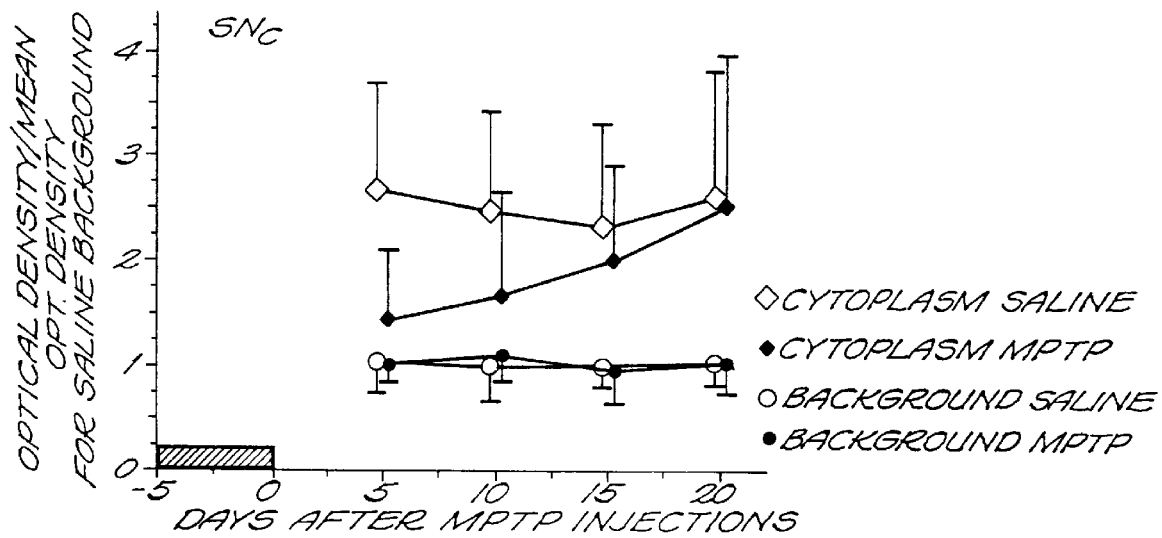
FIG. 18 is a graph showing the mean OD/mean O.D. for saline background versus days after MPTP injections.
Figure 18B:
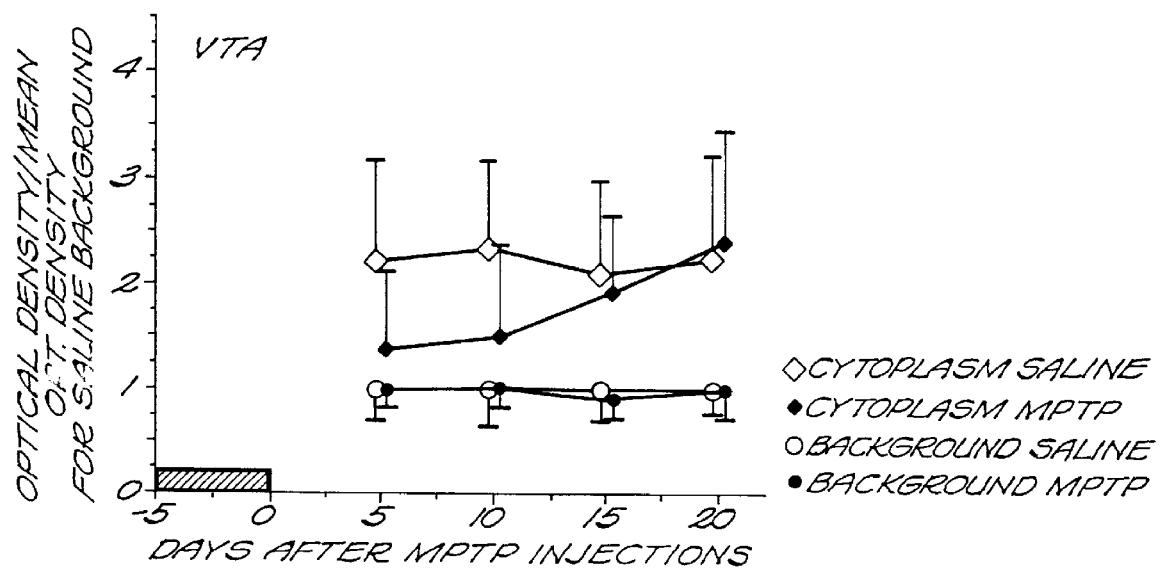
Figures 1, 19A:
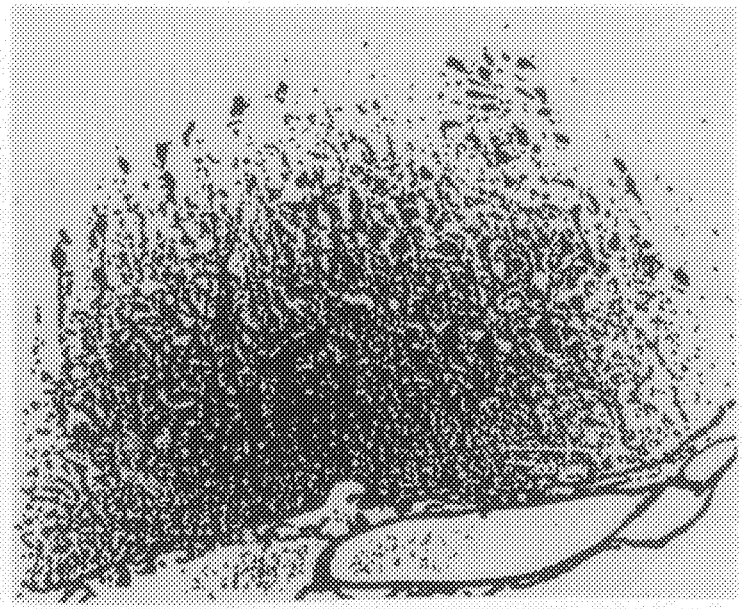
Figures 2, 19A:
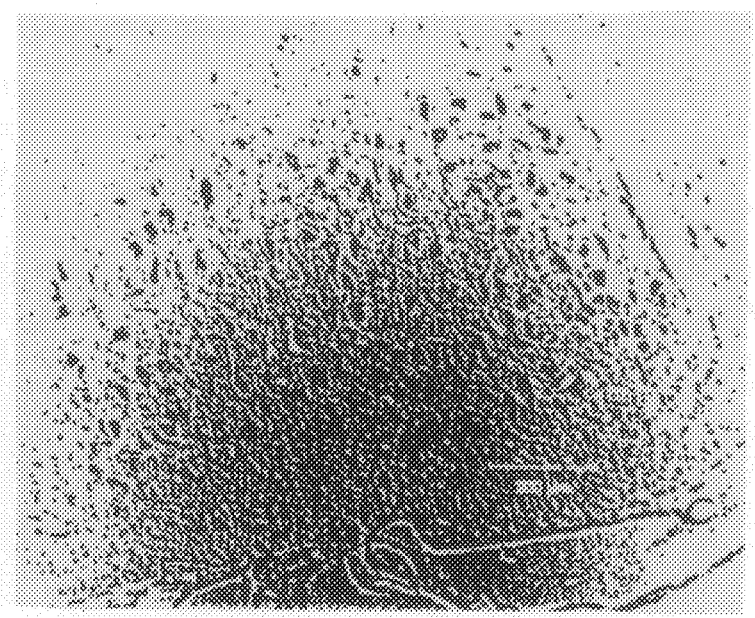
Figures 1, 19B:
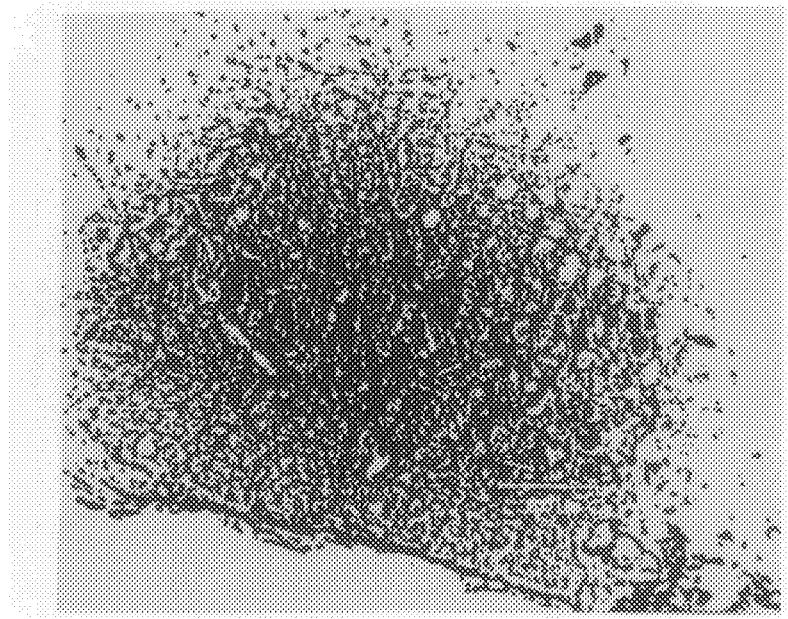
Figures 2, 19B:
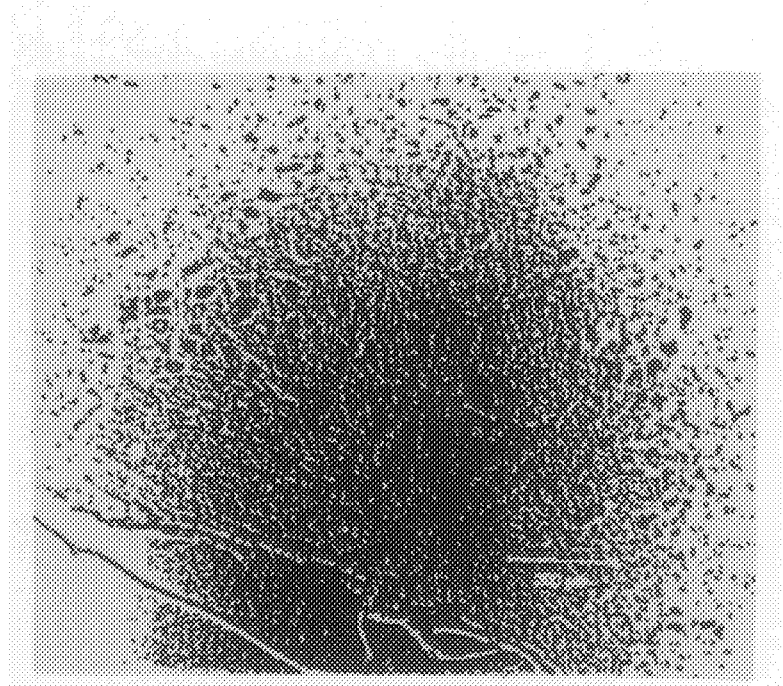

Within 5 days there was a marked reduction in cytoplasmic TH immunodensity for the MPTP treated SNc and VTA somata with a gradual recovery to a distribution approximately that of the saline controls by 20 days post-injection (FIGS. 17 and 18). The recovery of the TH immunodensity of SNc and VTA neurons following MPTP treatment parallels the recovery of striatal DA concentrations and locomotory activity.

The inventors have adapted spectral analysis techniques with fast Fourier transforms to the analysis of long term locomotory activity in mice treated with MPTP. This provides both highly sensitive and reproducible data that is not dependent on subjective assessment of animals that have been aroused by recent handling or the presence of observers. Initially, it was proposed that MPTP did not produce motor deficits in rodents due to the view that rat and mouse SNc neurons were resistant to the toxin. This was based largely on neurochemical data that reported only transient changes in striatal dopamine following MPTP (Ricuarte, G. A. et al. Brain Res. 1986, 376, 117–124, and Walters, A., et al. Biogenic Amines 1984, 1, 297–302). Others reported slowed limb movements, abnormal gait and chronically reduced locomotory activity in mice treated with high doses of the toxin which appeared to correlate with maintained changes in striatal DA concentration (Duvoisin, R. C., et al. In Recent Development in Parkinson's Disease; S. Fahn et al. Raven Press: New York, 1986; p. 147–154, Heikkila, R. E., et al. Science 1984, 224, 1451–1453, Heikkila, R. E., et al. Life Sci. 1985, 36, 231–236). Previous measurements of changes in locomotory activity in rodents following MPTP unfortunately have been either short term (Saghal A., et al. Neuroscl. Lett. 1985, 48, 179614 184) or brief isolated measurements (Willis, G. L., et al. Brain Res Bull 1987, 19, 57–62). To date there has been no satisfactory explanation of the behavioral recovery observed in various MPTP models including the cat (Schneider, J. S., et. al. Exp Neurol 1986, 91, 293–307), the marmoset (Waters, C. M., et al. Neuroscience 1987, 23, 1025–1039) or the rodent (Chiueh, C. C., et al. Psychopharmacol. Bull. 1984, 20, 548–553, and Johannessen, J. M. et al. Life Sci. 1985, 36, 219–224).

Locomotory activity as measured by the power under the P22–26 peak, striatal DA concentration and TH immunodensity in SNc and VTA somata are correlated in their recovery toward normal after MPTP treatment. The numbers of SNc and VTA somata with detectable TH immunoreactivity decay to a steady state level over the first 20 days after MPTP treatment. Hence dopamine content in the striatum is increasing while the number of SNc and VTA neurons with detectable TH content is decreasing. The rapid rise and fall of the DOPAC/DA ratio likely is related to the death of DA terminals in the striatum with loss of DA into the extracellular space. Yet the ratio is maintained at an increased level after Day 15 in support of the earlier findings suggesting that DA synthesis is increased in SNc neurons surviving MPTP exposure.

The measurements of TH immunodensity in the somata of SNc and VTA neurons are unlikely to provide a linear estimate of TH concentration. Although the use of the peroxidase reaction likely provides a linear estimate of the numbers of the secondary antibody-avidin complexes in the cytoplasm (Reis, D. J., et al. In Cytochemical Methods in Neuroanatomy Alan R. Liss, Inc.: New York, 1982; p. 205–228), the affinity constants for the inventors' polyclonal antibodies and those for the immunoreaction between the primary and secondary antibodies may not provide for a linear relationship between the concentration of the epitope and the concentration of avidin molecules. Yet, the results probably do indicate recovery in TH concentrations in the somata of VTA and SNc surviving MPTP exposure. The recovery of TH immunodensity parallels the increases in striatal DA content which suggests that a recovery of TH synthesis is factor in the recovery of DA content and possibly increased DA synthesis by individual surviving neurons.

Neostriatal dopaminergic and other catecholaminergic systems in rodents have been related to the generation of locomotory activity (Tabar J., et al. Pharmacol Biochem Behav 1989, 33, 139–146, Oberlander, C., et al. Neurosci. Lett. 1986,67, 113–118, Melnick, M. E. et al. 17th Annual Meeting Of The Society For Neuroscience, New Orleans, La., USA, Nov. 1987, 13, Marek, G. J., et al. Brain Res 1990, 517, 1–7, Rostowski, W., et al. Acta Physiol. Pol. 1982, 33, 385–388, Fink, J. S., Smith, G. P. J. Comp. Physiol. Psych. 1979, 93, 24–65). Yet the specific role, if any, of SNc or VTA neurons is uncertain. Hence the correlated recoveries for SNc and striatal parameters relative to the locomotory activity do not necessarily imply cause and effect. Yet the present inventors have suggested that since MPTP causes similar loss of TH+neurons in a variety of catecholaminergic systems (Seniuk, N. A. et al. Brain Res. 1990, 527: p.7–20), similar recovery of transmitter-related function in those systems to that we have shown for SNc and VTA dopaminergic neurons (Seniuk, N. A. et al. Brain Res. 1990, 527s p.7–20) may underlie the behavioral recovery. The recovery of DA synthesis may represent an attempt of the SNc neurons surviving the MPTP exposure to compensate for the loss of their fellows in that a component of the compensation is related to a recovery and then increased synthesis of tyrosine hydroxylase in the neurons surviving the MPTP exposure.

Example 4

An experiment was carried out to determine whether deprenyl can reduce the death of other axonally-damaged neuronal phenotypes, e.g., rat motoneurons. The proportion of rat motoneurons which die after axotomy is maximal during the first 4 days of life (80–90% loss) and then diminishes to adult levels (20–30% loss) over the next 3 to 4 weeks (Sendtner et al. Nature, 345, 440–441, 1990, Snider W. D. and Thanedar, S. J. Compl. Neuro 1, 270,489, 1989). Two groups (n=6) of fourteen day old rats received a unilateral facial nerve transjection (lesion) while two groups were unlesioned (no lesion). Paired lesion and no lesion groups were treated with saline, deprenyl (0.01 and 10 mg/kg), pargyline (10 mg/kg) every other day. The rats were sacrificed at 21 days after axotomy and serial coronal histological sections of the brainstem at the level of the facial nuclei processed for choline acetyl transferase (ChAT) immunocytochemistry (Tatton et al, Brain Res. 527:21, 1990 which is incorporated herein by reference) and Niss1 staining (Seniuk et al., Brain Res. 527: 7, 1990; Tatton et al. Brain Res. 527:21, 1990 which are incorporated herein by reference) (FIG. 19).

In particular, the right facial nerves were transected at their exits for the stylomastoid foramen under halothane-nitrous oxide anaesthesia for two groups of 14 day old Sprague-Dawley rats while two other groups were unoperated (n=6 in each group). On the day of the surgery, a lesioned and an unlesioned group were begun on deprenyl 10 mg/kg intraperitoneally every second day until sacrifice. The other lesioned and unlesioned groups were given identical injections with saline. Twenty one days after the transections, the rats were killed by anaesthetic overdose followed by perfusion with isotonic saline and 4% paraformaldehyde in phosphate buffer. Brains from the unlesioned groups were bisected longitudinally along the midline and the half brains from saline treated and deprenyl treated animals were glued together using Tissue-Tek so that the surface landmarks coincided. The glued brains for the unlesioned animals and the intact brains for the lesioned animals were frozen in −70° C. methylbutane and 10 μm serial sections were cut through the portion of the medulla containing the facial nuclei. Every third serial section was reacted with a polyclonal antibody against ChAT then incubated with biotinylated secondary antibody, followed by incubation with HRP conjugated avidin and finally reacted with diaminobenzidine and hydrogen peroxide (Tatton et al., Brain Res. 527:21, 1990). The paired sections for the glued half brains insured that any differences in immunoreaction between the deprenyl and saline unlesioned control groups were not due to different penetration or exposure to the antibodies or the reagents.

The following experiments were also carried out using the procedures described above:

A group of fourteen day old rats received a unilateral facial nerve transection (lesion) while groups were unlesioned (no lesion). Paired lesion and no lesion groups were treated with saline or deprenyl (10 mg/kg) every other day. The rats were sacrificed as and ChAT immunochemistry was carried out as described herein.

A group of fourteen day old rats received a unilateral facial nerve transection and were treated with 10 mg/kg deprenyl every other day for 21 days. Animals were sacrificed at 35 days of age and at 65 days of age and ChAT immunochemistry was carried out as described herein.

A group of one day old rats received a unilateral facial nerve transection and were treated with deprenyl every other day with saline or deprenyl (10 mg/kg). The animals were sacrificed at 8 days of age and ChAT immunochemistry was carried out as described herein.

FIG. 19 shows photomicrographs of adjacent ChAT immunoreacted (A1 and B1) and Niss1 stained (A2 and B2) sections through the fscial nucleus ipsilateral to transection of the facisl nerve. A1 and A2 are for saline treated animals and B1 and B2 are for deprenyl treated animals.

Figure 20:
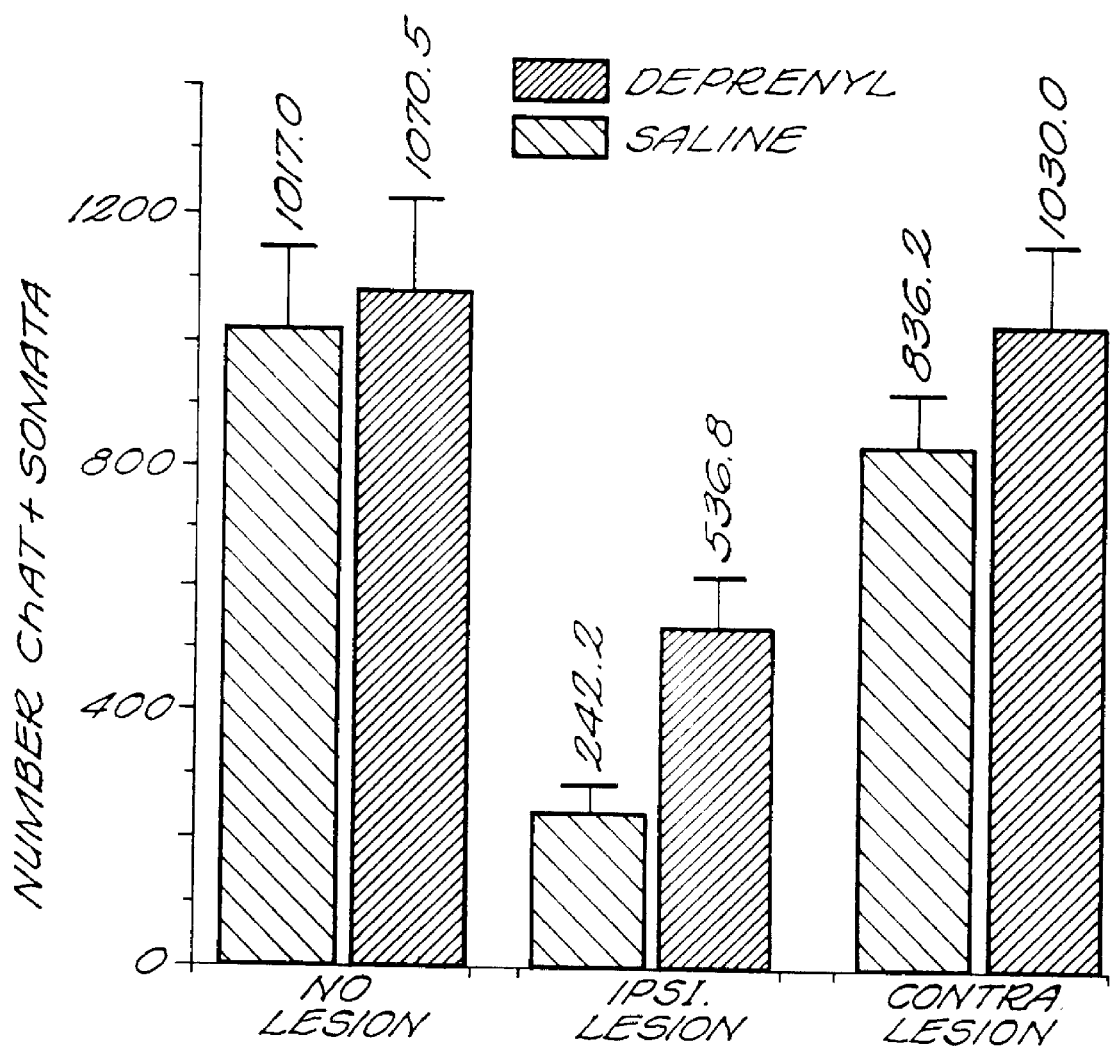
FIG. 20 is a bar graph for the counts of ChAT+ somata for the facial nuclei for the different lesion and treatment groups (bars-means, error bars-standard deviations)

FIG. 20 is a bar graph for the counts of ChAT+ somata for the facial nuclei for the different lesion and treatment groups (bars-means, error bars—standard deviations). ChAT immunoreactive somata containing nuclear profiles were counted from every third section taken serially through entire facial nuclei. The value at the top of each bar is the mean. The Ipsi.Lesion and Contra.Lesion indicate the nuclei located ipsilaterally and contralaterally to the facial nerve transection respectively. The counts were not adjusted to estimate the total numbers of ChAT+ somata in the facial nuclei, so the numbers for unlesioned groups are approximately one third of values reported for counts of Niss1 stained somata. The values were compared statistically in a pairwi~e fashion using the Mann Whitney U test.

As shown in FIG. 20 counts of ChAT immunopositive (ChAT+) somata for every third serial section through the full lengths of the facial nuclei were statistically the same ($p=0.520$) for the no lesion-saline and the no lesion-deprenyl groups. In contrast, the numbers of ChAT+ somata decreased significantly for the lesion-saline group for the facial nuclei both ipsilateral (23.8% no lesion-saline, $p=0.003$) and contralateral (82.2% no lesion-saline, $p=0.024$) to the facial nerve transection. Deprenyl treatment more than doubled the number of ChAT+ somata for the ipsilateral lesioned facial nucleus (52.7% no lesion-saline $p=0.004$) and prevented the decrease in the ChAT+ counts for the contralateral nucleus 80 that they were statistically the same as the no lesion groups ($p=0.873$).

Figure 21A:
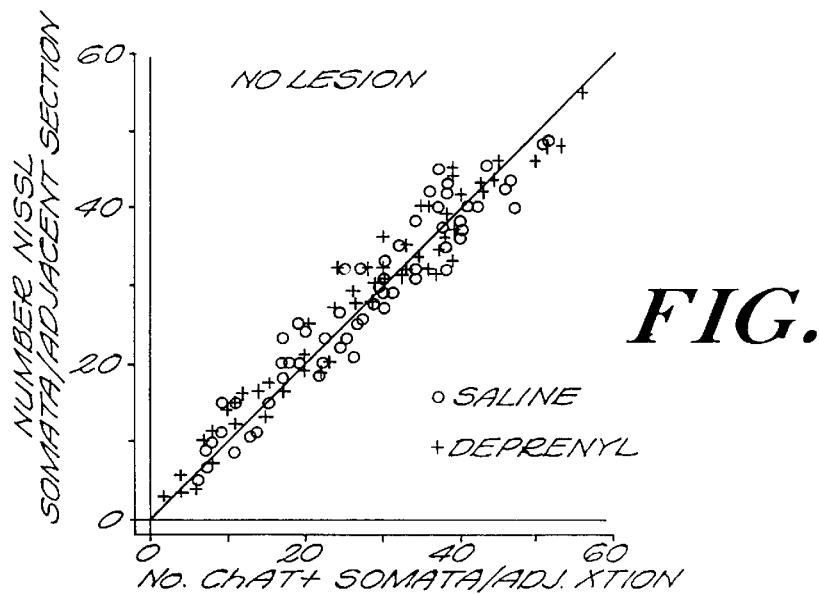
FIG. 21 depicts graphs showing joint Nissl/ChAT+ counts of adjacent sections for the no lesion groups (FIG. 14A), the ipsilateral lesion-saline animals (FIG. 14B), the lesion-deprenyl animals (FIG. 14B), and the contralateral lesion animals (FIG. 14C)
Figure 21B:
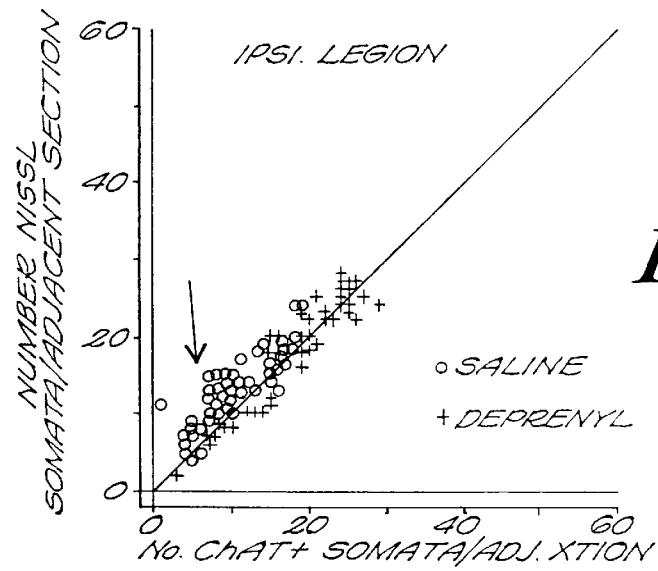
Figure 21C:
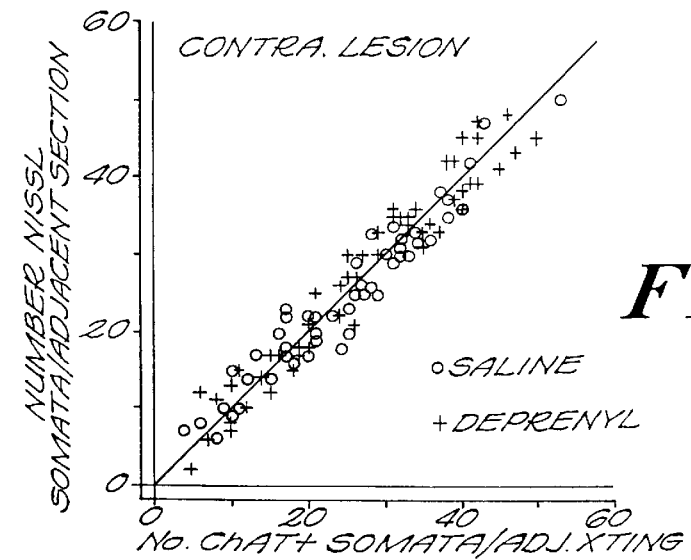

FIG. 21 shows the joint Niss1/ChAT+ counts of adjacent sections. One of each pair of intervening sections between those that were immunoreacted for ChAT was Niss1 stained. With the aid of a camera lucida the number of ChAT+somata and Niss1-stained nucleolus-containing somata (Oppenheim, R. W. J. Comp. Neurol. 246:281, 1986 for criteria) were counted in matching areas of adjacent sections on 20 randomly-chosen sections through the length of each nucleus for each animal. Niss1 counts were then plotted against ChAT+ counts for the adjacent sections values from three animals in each lesion-treatment group were pooled). Comparison of Niss1 and ChAT+ somal counts were done to determine whether decreases in the number of immunopositive somata reflected the death of the motoneurons or loss of immunoreactivity.

The joint plots of the Niss1/ChAT somal counts for the no lesion groups (FIG. 21) show distributions that are symmetrical around the equal value diagonal with similar means and standard deviations for the saline (Niss1 $27.6+/-12.04$, ChAT+ $27.3+/-13.80$, $p=0.526$, Niss1 and ChAT counts for the same groups were compared using; the paired t test) and deprenyl groups (Niss1 $28.9+/-13.2$, ChAT $28.5+/-13.8$, $p=0.641$). The ipsilateral lesion-saline animals (FIG. 21) show lower joint values with an asymmetrical distribution with respect to the equal value diagonal (the shift to higher Niss1 values is marked by an arrow) with is reflected in the higher mean value for the Niss1 counts ($12.6+/-4.18$) relative to the ChAT+ counts ($9.7+/-4.0$, $p=0.001$). The lesion-deprenyl points (FIG. 21B) showed a smaller reduction than the saline points and had a symmetrical distribution around the equivalent value diagonal (Niss1 $17.6+/-6.5$, ChAT+ $17.5+/-6.1$, $p=0.616$). Finally, the plot for the contralateral lesion animals (FIG. 21C) shows that the points for both the saline (Niss1 $24.6+/-10.1$, ChAT+ $24.8+/-10.7$, $p=0.159$) and deprenyl (Niss1 $28.9+/12.1$, $28.5+/-12.0$, $p=0.74$ 1) groups are symmetrically distributed relative to the equivalent value diagonal.

Thus, the distribution of the joint Niss1/ChAT+ plots to above the equal value diagonal and the significant difference between the joint Niss1 and CHAT+ counts for the ipsilateral lesion-saline animals (FIG. 21) showed that about 84% of the decrease in the numbers of ChAT+ somata shown in FIG. 20 resulted from motoneuronal death while loss of ChAT immunoreactivity only caused about 16% of the decrease in ChAT+ motoneurons. The joint counts also showed that all of the loss of ChAT+ somata from the contralateral nuclei resulted from motoneuronal death. Most importantly, the joint counts established that deprenyl treatment caused a marked reduction in the motoneuronal death and reversed or prevented the loss of ChAT immunoreactivity in surviving motoneurons in the ipilateral nuclei. It also prevented any motoneuronal death in the contralateral nuclei.

Figures 1, 22B:
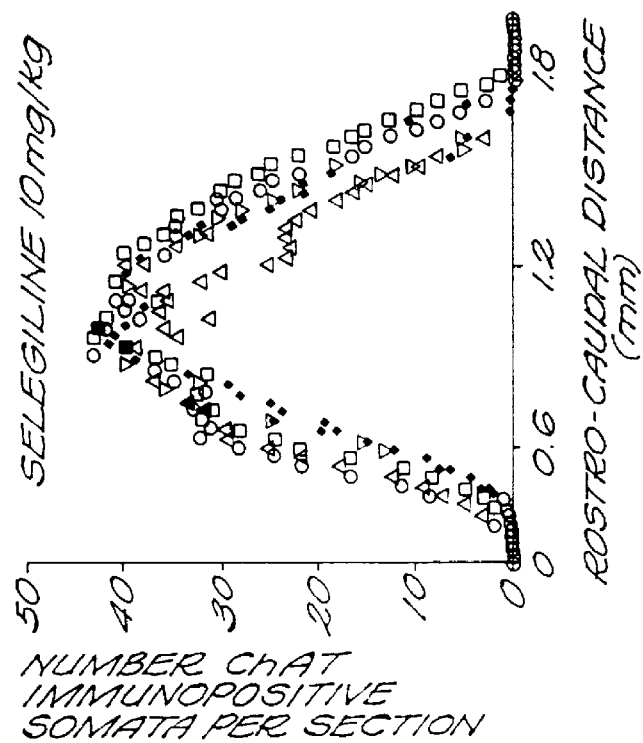
Figures 1, 22A:
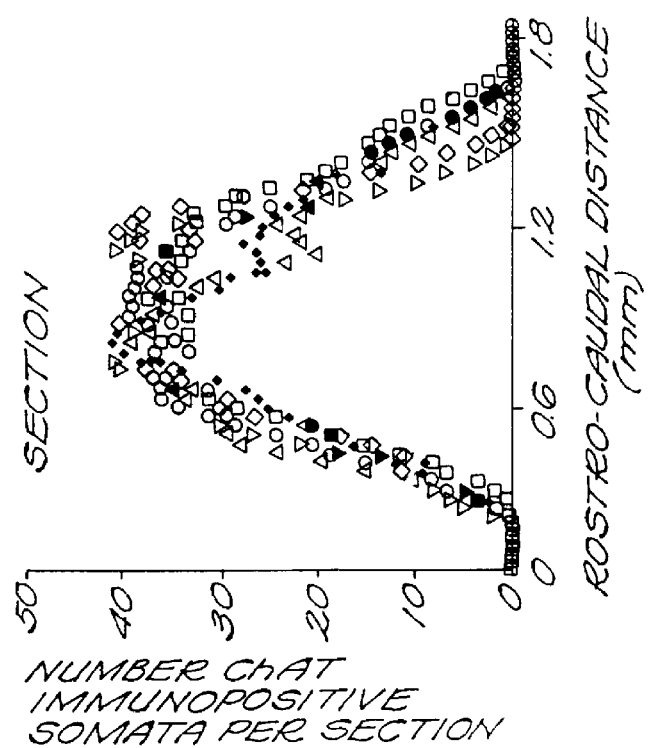

FIG. 22 shows ChAT+ counts for facial motoneurons in 35 day old rats after a unilateral axotomy at 14 days of age. It shows the rescue of the motoneurons whose axons were transected (IPSI transection) and the complementary rescue of the small number of facial motoneurons that die on the opposite side of the brainstem (Contra transection).

Figure 23:
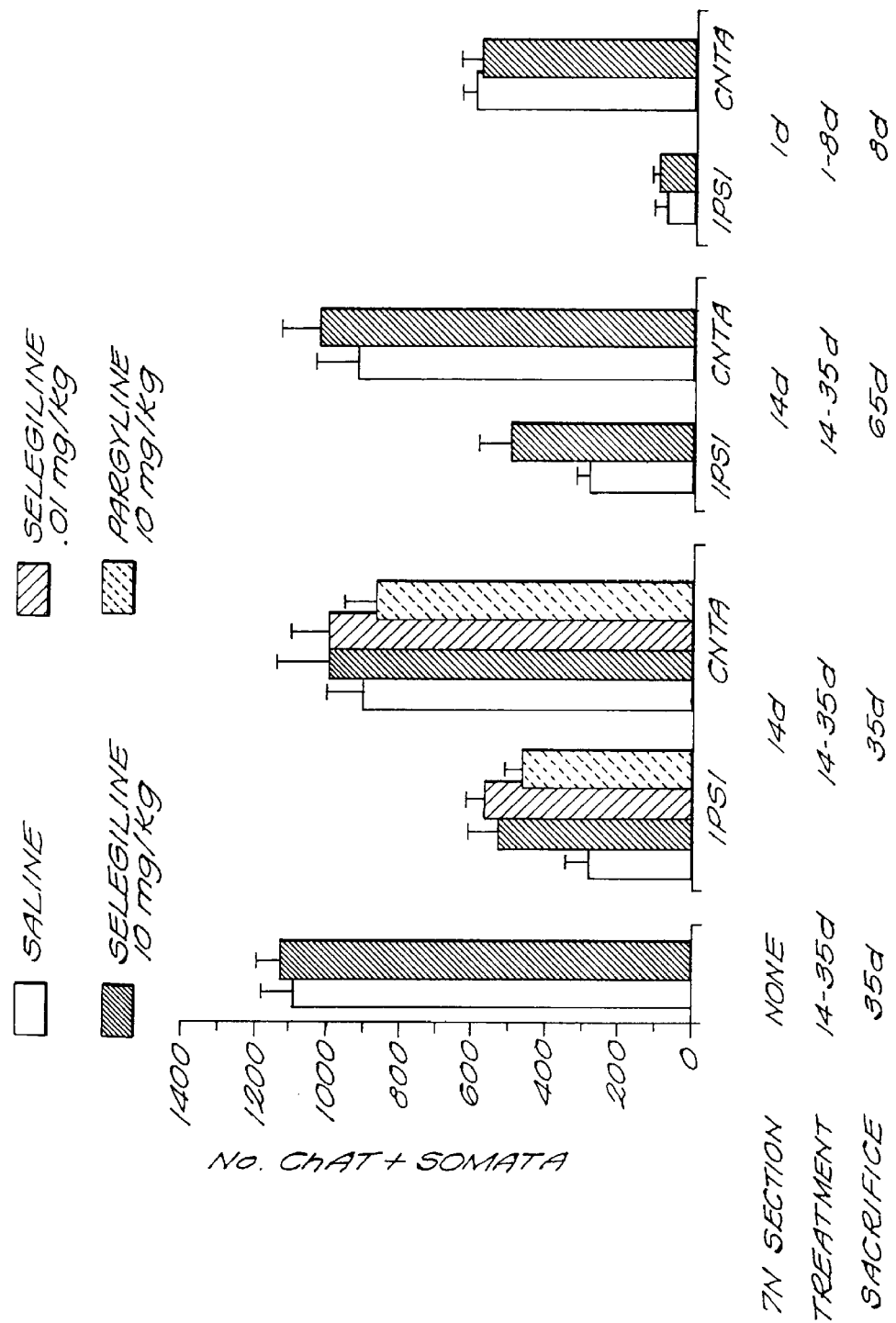
FIG. 23 shows the data shown in FIG. 20 and includes data for additional animals.

FIG. 23 sets out the data shown in FIG. 20 (leftmost two groups of bars) and includes data from some additional animals (group sizes increased from 6 to 8 or more). It also shows that pargyline rescues the motoneurons (hatched bars, possibly more weakly than deprenyl as the groups differ at the $p<0.05$ level). Further, a dose of 0.01 mg/kg of deprenyl was found to be just as effective as 10 mg/kg deprenyl in rescuing the motoneurons similar to the 0.01 mg/kg dose used with the MPTP model.

Animals lesioned at 14 days, treated for the next 21 days with 10 mg/kg deprenyl (d14–35) and then left untreated until 65 days of age do not show any further motoneuronal death (compare the third group of bars from the left to the corresponding bars in the second group that were sacrificed at 35 days of age when deprenyl treatment was still under way). This indicates that the rescue is permanent for the axotomized motoneuron i.e. the motoneurons do not begin to dle when deprenyl treatment is discontinued after 21 days and there is not further death over the next 30 days.

FIG. 23 also shows that rat motoneurons whose axons are transected at 1 day of age have a greater amount of death than 14 day motoneurons and cannot be rescued by deprenyl. Therefore, it appears that some factor must reach maturity in the nervous system before deprenyl can be effective and that factor appears between 1 and 14 days of age.

This is the first evidence that deprenyl can prevent the death of motoneurons and is consistent with the work indicating that deprenyl can reduce the death of axonally-damaged neurons. The death of axotomized motoneurons in immature rats is believed to reflect a dependency of the motoneurons for trophic support from the muscles they innervate (Crews, L. and Wigston, D. J.; J. Neurosci 10, 1643, 1990; Snider, W. D. and Thanedar, S. supra). Recent studies have shown that some neuronotrophic factors can reduce the loss of the motoneurons supporting that concept (Sendtner, M. et al., Nature 345:440, 1990). This study suggests that deprenyl has the capacity to activate some mechanism which compensates for the loss of target derived trophic agents. Part of the action of deprenyl in neurodegenerative diseases may reflect a similar compensation for reduced trophic support.

The finding of a small amount of motoneuronal death in the facial nucleus contralateral to a facial nerve transection is in accord with previous reports of decreased numbers of axons in the intact nerve contralateral to the transection of a motor nerve (Tamaki, K. Anat. Rec. 56, 219, 1933) and a variety of other changes in contralateral nuclei (Pearson, C. A. et al. Brain Res. 463, 1988). Deprenyl completely prevents the death of the contralateral motoneurons.

Axotomy initiates transient changes in protein synthesis in facial motoneurons (Tetzlaff, W. et al. Neuro Sci. 8, 3191 (1988)) which include decrease in choline acetyl transferase (Hoeover, D. R. & Hancock, J. C. Neuroscience 15, 481, 1985). The small proportion of saline-treated motoneurons in the ipsilateral nuclei (16%) which lost ChAT immunoreactivity probably reflects the surviving motoneurons that had not recovered sufficient ChAT concentrations to be immunochemically detectable. Deprenyl prevented or reversed the loss of ChAT immunoreactivity in surviving motoneurons.

The dose of deprenyl (10 mg/kg) was sufficient to block the majority of MAO-B activity and some MAO-A activity as well (Demarest, R. T., Aazzaro, A. J. in Monoamine Oxidase: Structure, Function and Altered Functions (eds. Singer, T. P., Korff, R. W. and Murphy, D. L.) 423–340, Academic Press, New York, 1979) hence the reduction in motoneuron death may be due to MAO-B or MAO-A inhibition or may be independent of both enzymes. However, it is expected that a 0.01 mg/kg deprenyl dose will produce a reduction in motoneuron death similar to that obtained with the 10 mg/kg dose. The 0.01 mg/kg dose does not produce any significant MAO-A or MAO-B inhibition indicating that the rescue with 0.01 mg/dg deprenyl is not due to MAO-A or MAO-B inhibition. (See example 2). Thus, it is more likely that the reduction in motoneuron death will be independent of MAO-B or MAO-A.

A recent study has shown that MAO-inhibitors may be more effective then deprenyl in reducing the necrosis of dorsal striatal neurons after a transient interruption of the arterial blood supply to that region (Matsui, Y. and Kamagae, Y., Neurosci. Lett. 126, 175–178, 1991). Yet deprenyl doses (0.25 mg/kg) too low to produce inhibition of MAO-A but sufficient to product 20–75% inhibition of MAO-B in mice are as effective as a 10 mg/kg dose in preventing the death of SNc neurons. MAO-B is largely concentrated in glial cells although present in some serotonergic and histaminergic neurons (Vincent, S. R. Neurosci 28, 189–199 (1989); Pintnri, J. E. et al. Brain Res. 276, 127–140, 1983). Since microglial cells show a proliferative response and astroglia respond by an increase in protein synthesis to is axotomy involving nearby motoneurons, glial cells may be involved in deprenylinduced prevention of neuronal death.

Example 5

Age Related Death of Mouse SNC neurons.

Studies were carried out to determine whether deprenyl prevents age-related death of mouse dSNc neurons using the procedures set out in Tatton W. G. et al Neurobiol. Aging 1991; 12:5,543. The results are shown in FIG. 24.

Figure 24:
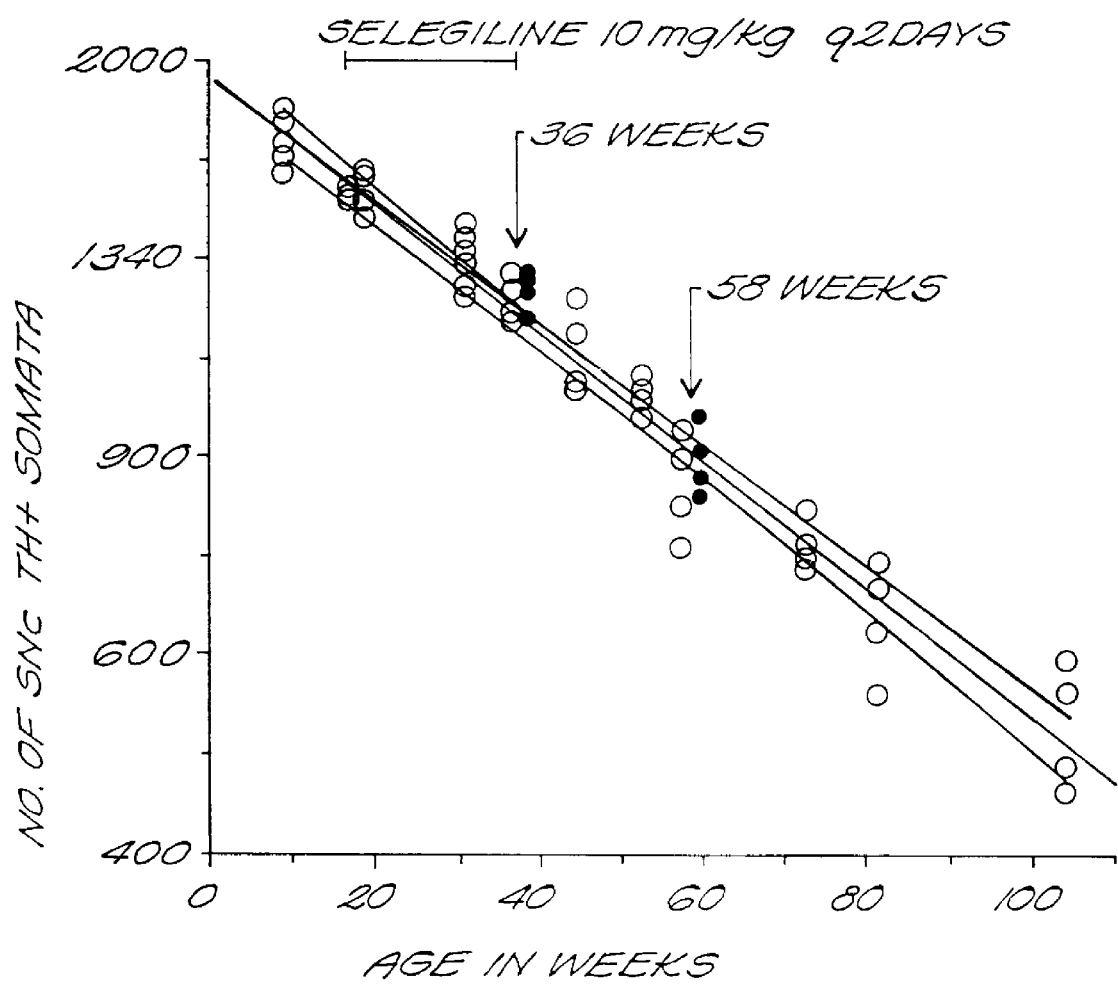
FIG. 24 shows the counts of TH+ SNc somata following treatment with deprenyl.

As shown in FIG. 24, deprenyl does not prevent age-related death of mouse dSNc neurons.

Example 6

N-(2-aminoethyl)-4-chlorobenzamidehydrocloride having the following formula

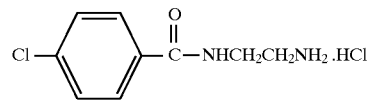

was obtained from Research Biochemicals Incorporated, Natick Mass., U.S.A. (Cat. No. R-106, No. R016-6491) and was tested to determine if it rescued immature axotomized motoneurons. A group of fourteen day old rats received a unilateral facia nerve transection and were treated with 10.5 mg/Kg N-(2-aminoethyl)-4-chlorobenzamide every other day for 21 days. The rats were sacrified at 35 days of age and CHAT+ immunochemistry was carried out as described in Example 4.

Figure 25:
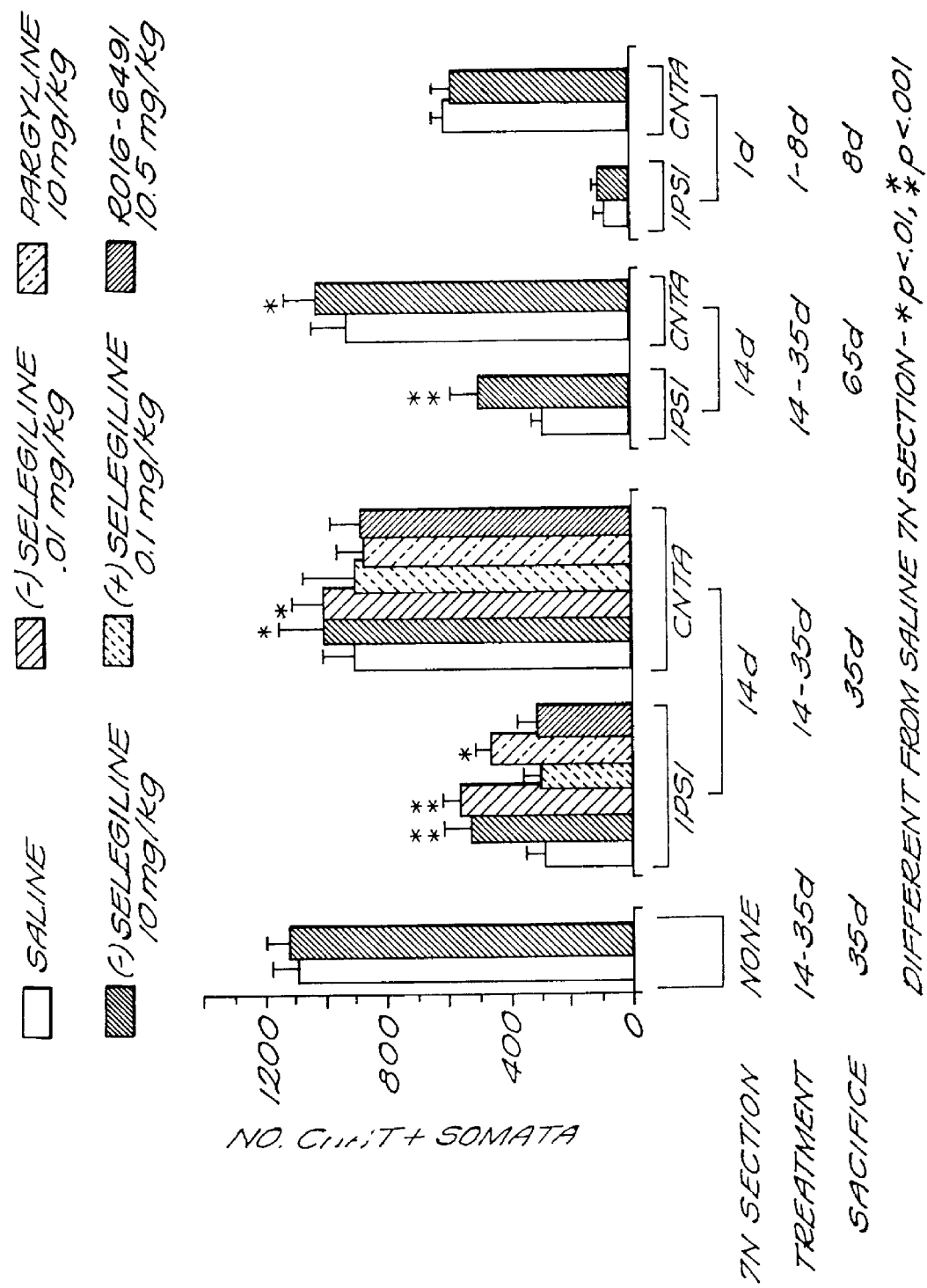
FIG. 25 shows the data shown in FIG. 23 and includes data from animals treated with N-(2-aminoethyl)-4-chlorobenzamide.

FIG. 25 contains the data shown in FIG. 23 and includes data from the animals treated with N-(2-aminoethyl)-4-chlorobenzamide.

As shown in FIG. 25 the compound did not rescue the immature axotomized motoneurons (FIG. 25). It should be noted that the compound does not have the alkynyl terminus of deprenyl and pargyline so that it may bind or associate with a different part of the flavine portion of MAO-B. The binding of the propargyl group is permanent (irreversible inhibition of MAO-B) while the N-(2-aminoethyl)-4-chlorobenzamide binding is reversible and short lived.

Example 7

The (+) isomer and (−) isomer of deprenyl were tested to determine whether the rescue of immature axotomized motoneurons was stereospecific. A group of fourteen day old rats received a unilateral facial nerve transection and were treated with 0.1 mg/kg of the (−) isomer or (+) isomer of deprenyl every other day for 21 days. The rats were sacrificed at 35 days of age and CHAT+ Immunochemistry was carried out as described in Example 4. As shown in FIG. 25, the (+) deprenyl at a dosage of 0.1 mg/kg does not rescue the motoneurons. The rescue appears to be stereospecific to the (−) isomer. Thus, even through the (+)-deprenyl has a propargyl moiety, the configuration at the chiral center of the molecule may affect binding to the molecular site that initiates the rescue.

Example 8

Studies were carried out to determine the affect of deprenyl in an animal stroke model. Rats were treated with carbon monoxide and received glucose i.v. The carotid artery was then clamped and deprenyl was administered to the animals. The clamp was then removed causing stroke in the animals. Deprenyl was also administered to a group of untreated animals one half hour after removal of the clamp. Positive neurons were determined in serial sections of the brain as described above. Deprenyl was found to reduce neuronal death and decreased the extent of damaged areas, in particular in the hippocampus.

EQUIVALENTS

Those skilled in the art will recognize or be able to ascertain, using no more than routine experimentation, many equivalents to the specific embodiments of the invention described herein. Such equivalents are intended to be encompassed by the following claims.

We claim:

1. A method for rescuing damaged nerve cells in a patient, comprising:

administering to a patient having damaged nerve cells an amount of a deprenyl compound such that rescuing of damaged nerve cells occurs in the patient;

with the proviso that the deprenyl compound in not selected from the group consisting of deprenyl, pargyline, AGN-1133, and AGN-1135, and wherein the deprenyl compound is represented by the structure:

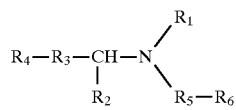

in which $R_1$ is hydrogen or alkyl;
$R_2$ is hydrogen or alkyl;
$R_3$ is a single bond or alkylene;
$R_4$ is heterocyclyl, aryl or aralkyl;
$R_5$ is alkylene; and
$R_6$ is

—C≡CH;

or a pharmaceutically acceptable salt thereof.

2. The method of claim 1, wherein $R_1$ is a group that can be removed in vivo.
3. The method of claim 1, wherein $R_1$ is hydrogen.
4. The method of claim 1, wherein $R_1$ is alkyl.
5. The method of claim 4, wherein $R_1$ is methyl.
6. The method of claim 1, wherein $R_2$ is methyl.
7. The method of claim 2, wherein $R_3$ is methylene.
8. The method of claim 1, wherein $R_4$ is aryl.
9. The method of claim 1, wherein $R_4$ is phenyl.
10. The method of claim 1, wherein $R_5$ is methylene.
11. The method of claim 1, wherein the deprenyl compound is represented by the structure:

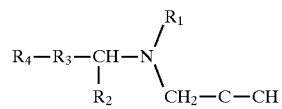

in which $R_3$ is a single bond or methylene.

12. The method of claim 1, wherein the deprenyl compound is represented by the structure:

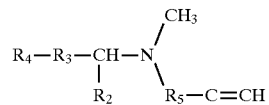

in which $R_3$ is a single bond or methylene.

13. The method of claim 1, wherein the deprenyl compound is represented by the structure:

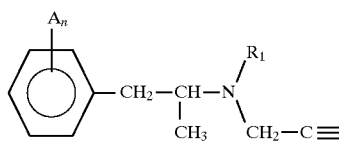

in which

A is a substituent independently selected for each occurrence from the group consisting of halogen, hydroxyl, alkyl, alkoxyl, cyano, nitro, amino, carboxyl, —CF$_3$, or azido;

n is 0 or an integer from 1 to 5;

or a pharmaceutically acceptable salt thereof.

14. The method of claim 1, wherein the deprenyl compound is (-)-desmethyldeprenyl.

15. The method of claim 1, in which the deprenyl compound administered to the patient is provided in a kit comprising a container of the deprenyl compound and instructions for administering a therapeutically effective amount of the deprenyl compound to a subject having damaged nerve cells such that rescuing of damaged nerve cells occurs in the subject.

16. The method of claim 1, in which the deprenyl compound is administered to the patient with a needleless hypodermic injection device.

17. The method of claim 1, in which the deprenyl compound is formulated in liposomes.

18. The method of claim 17, in which the liposomes comprise a targeting moiety.

19. The method of claim 1, wherein $R_4$ is heterocyclyl.

20. The method of claim 14, in which the deprenyl compound is administered to the patient with a needleless hypodermic injection device.

21. A method for rescuing damaged nerve cells in a patient, comprising;

administering to a patient having damaged nerve cells an amount of deprenyl compound such that rescuing of damaged nerve cells occurs in the patient;

wherein the deprenyl compound is represented by the structure.

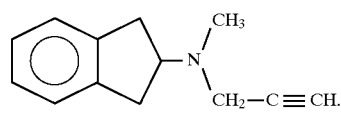

* * * * *